United States Patent
Hibi et al.

[11] Patent Number: 6,030,964
[45] Date of Patent: Feb. 29, 2000

[54] MONO- OR POLYENIC CARBOXYLIC ACID DERIVATIVES

[75] Inventors: Shigeki Hibi; Kouichi Kikuchi; Hiroyuki Yoshimura; Mitsuo Nagai; Katsuya Tagami; Shinya Abe; Ieharu Hishinuma; Junichi Nagakawa; Norimasa Miyamoto; Takayuki Hida; Aichi Ogasawara; Seiko Higashi, all of Ibaraki; Kenji Tai, Ibarabi; Takashi Yamanaka; Makoto Asada, both of Ibaraki, all of Japan

[73] Assignee: Eisai Co., Ltd., Japan

[21] Appl. No.: 09/106,112

[22] Filed: Jun. 29, 1998

Related U.S. Application Data

[62] Division of application No. 08/836,428, filed as application No. PCT/JP95/02231, Oct. 31, 1995.

[30] Foreign Application Priority Data

Oct. 31, 1994 [JP] Japan .................................. 6-276287
Jun. 30, 1995 [JP] Japan .................................. 7-166120

[51] Int. Cl.⁷ ...................... C07D 223/16; C07D 225/06; A61K 31/55
[52] U.S. Cl. .................. 514/183; 514/213; 540/476; 540/593
[58] Field of Search .................... 514/183, 213, 514/215, 217; 540/476, 479, 577, 578, 580, 586, 587, 588, 591, 593, 594, 595

[56] References Cited

U.S. PATENT DOCUMENTS

| | | | |
|---|---|---|---|
| 4,894,386 | 1/1990 | Brown | 514/414 |
| 4,977,276 | 12/1990 | Berlin | 549/58 |
| 5,039,684 | 8/1991 | Bernareggi | 514/314 |

FOREIGN PATENT DOCUMENTS

| | | |
|---|---|---|
| 2-268181 | 11/1990 | Japan . |
| 5-78315 | 3/1993 | Japan . |
| 6-9616 | 1/1994 | Japan . |
| WO 94/29275 | 12/1994 | WIPO . |

OTHER PUBLICATIONS

Silhankova, Collection Czech Chem Comm, vol. 43, pp. 1484–1487, 1978.
Stokker, Heterocycles, vol. 26(3), pp. 157–162, 1987.
Keidel, Molecular and Cellular Biology, vol. 14(1) Jan. 1994, pp. 287–289.
Ca: J. Am. Chem. Soc., vol. 115, pp. 7192–7198, 1993.
Robinson, Tetrahedron, vol. 46(2), pp. 335–340, 1990.
Makosa, Synthesis, pp. 1142–1144, 1987.
Varga, Molecular Immunology, vol. 28(6), pp. 641–654, 1991.
Sunthankar, J of Pharmaceutical Sciences, vol. 82(5), pp. 543–545, 1993.
Chemical Abstracts 124:261073, 1996.
Chemical Abstracts 121:180227, 1993.
Chemical Abstracts 118:191764, 1992.
Chemical Abstracts 115:208082, 1991.
Chemical Abstracts 112:158233, 1989.
Chemical Abstracts 102:220710, 1985.
Crettaz et al Biochem J. (1990) 272, 391–397 "Ligand specificities of recombinant retinoic acid receptors RARα and RARβ".
Sani et al Archives of Biochemistry and Biophysics vol. 238, No. 1, Nov. 15, 1990 pp. 107–113 "Isolation, Partial Purification and Characterization of Nuclear Retinoic Acid Receptors from Chick Skin".
Niculesclu–Duvaz et al Carcinogenesis vol. 6, No. 4, pp. 479–486, 1985 "QSAR application in chemical carcinogenesis. II. QSAR analyis of a class of carcinogenesis inhibitor: retinoids".

*Primary Examiner*—Mukund J. Shah
*Assistant Examiner*—Deepak Rao
*Attorney, Agent, or Firm*—Nixon & Vanderhye

[57] ABSTRACT

Compounds of the formula

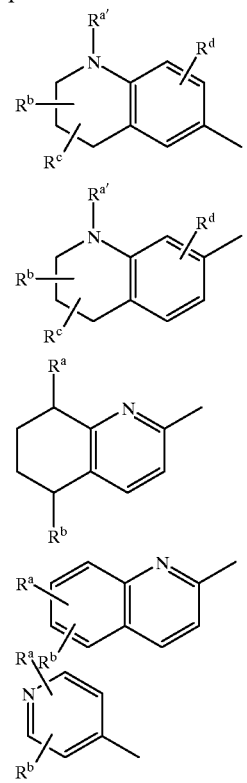

and compounds of the formula (1-V)

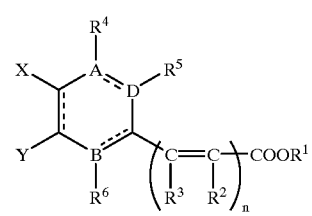

or their salts have the potent ability to bind to retinoic acid receptors thus useful in treating psoriasis and rheumatoid arthritis.

7 Claims, 1 Drawing Sheet

MONO- OR POLYENIC CARBOXYLIC ACID DERIVATIVES

This is a divisional of application Ser. No. 08/836,428, filed May 6, 1997, now pending, which is a 371 of PCT/JP95/02231 filed Oct. 31, 1995.

INDUSTRIAL FIELD OF APPLICATION

The first embodiment of the present invention relates to mono- or polyenic carboxylic acid derivatives or physiologically acceptable salts thereof or drugs containing the mono- or polyenic carboxylic acid derivatives or the physiologically acceptable salts thereof.

The second embodiment of the present invention relates to heterocyclic compounds. More particularly, it relates to novel heterocyclic compounds which are extremely effective in the prevention and treatment of diseases.

BACKGROUND OF THE INVENTION AND PRIOR ART

Retinoic acid (vitamin A acid, abbreviation: RA) is an essential substance to the growth and life support of humans and other mammals. It has been known that retinoic acid acts as a morphogenesis factor in ontogenesis and functions variously in the differentiation and proliferation of adults. For example, it has been known that the acid participates in the cornification, formation of hairs, functions of sebaceous glands, and so on with respect to the epidermis, in the metabolism of bones and cartilages with respect to the connective tissues, in the regulation of immune functions with respect to the immune system, in the differentiation of nerve cells with respect to the nervous system, in the differentiation and proliferation of blood cells with respect to the hemic system, and in the secretion of thyroid hormones, parathyroid hormones and so on and the regulation of the functions thereof in target organs, thus taking part in the mineral metabolism and the basal metabolism. These various physiological actions of retinoic acid are exhibited by directly controlling gene expression through retinoid receptor (RARs, RXRs) family present in cell nuclei. With respect to retinoic acid, there are not only deficiencies but also excesses thereof such as abnormality in cornification, depilation, metabolic disorder of bones and cartilages, and so on. Further, the abnormality of retinoid receptors has recently been found in acute promyelocytic leukemia, head and neck squamous cell carcinoma, lung cancer and so on, and the participation of retinoic acid in the sideration and evolution thereof has been reported.

In order to elucidate detailed mechanisms of these various actions of retinoids and to find the possibility for clinical application thereof, it has great significance to develop compounds antagonistic against retinoids. Although TD-550 and TD-560 (Cell Biol. Rev., 25, 209(1991)) and Ro41-5253 (Proc. Natl. Acad. Sci., U.S.A., 89, 7129 (1992)) have already been known as compounds antagonistic against retinoids, they are thought to be poor in both the ability to bind RARs and antagonism against retinoids.

Meanwhile, RARs and RXRs are known as retionid receptors, which are members of steroid/thyroid receptor superfamily present in cell nuclei. Known receptors belonging to this superfamily include estrogen receptors (ER), thyroid hormone receptors (TR), vitamin $D_3$ receptors ($D_3R$) and steroid hormone receptors. With respect to RXRs, there are α-, β- and γ-subtypes, and the ligand thereof has recently been identified with 9-cis RA. Further, it has been found that RXRs have the physiological property of forming heterodimers together with RXRs, TR, $D_3R$ or other receptors. Thus, it is being elucidated that RXRs act synergistically with their respective inherent ligands to take great part in the expression of the functions of retinoic acid, vitamin $D_3$ or thyroid hormones through such heterodimers. In order to elucidate detailed mechanisms of these various actions of RXRs and to find the possibility for clinical application thereof, it has great significance to develop compounds binding to RXRs.

In view of the above actual circumstances, the inventors of the present invention have intensively studied to find that mono- or polyenic carboxylic acid derivatives which will be described below exhibit agonism for RXRs and are useful as drugs. As the prior art, although JP-A-2-76862 and EP 0568898 disclose monoenic carboxylic acid derivatives and polyenic carboxylic acid derivatives these derivatives are different from the compounds of the present invention in both chemical structure and drug effect.

Further, the inventors of the present invention have found that heterocyclic compounds described below exhibit extremely high ability to bind RARs and antagonism against retinoids, thus accomplishing the present invention.

For example, JP-A-2-240058 discloses heterocyclic compounds which exhibit such a function of agonist and are improved in the adverse reaction due to retinoid excess. However, these compounds are different from the compounds of the present invention in both chemical structure and drug effect.

DISCLOSURE OF THE INVENTION

The first embodiment of the present invention relates to mono- or polyenic carboxylic acid derivatives represented by the formula (1-I) or physiologically acceptable salts thereof:

$$Z-(CR^3=CR^2)_n-COOR^1 \qquad (1\text{-}I)$$

[wherein $R^1$ is hydrogen or a carboxyl-protecting group; $R^2$ and $R^3$ are each independently hydrogen atom, halogen, linear lower alkyl, branched lower alkyl, linear lower alkoxy, branched lower alkoxy or aryl; n is an integer of 1 to 3; $nR^2$'s or $nR^3$'s may be the same or different from one another; and Z is a group represented by the general formula (1-II), (1-III) or (1-IV):

(1-II)

(1-III)

(1-IV)

{wherein A, B and D are each carbon, nitrogen, sulfur or oxygen, with the carbon or nitrogen atom optionally bearing a substituent; $X^1$ and $Y^1$ are each independently hydrogen, $-NR^4R^5$, $-CR^6R^7R^8$, $-OR^9$, $-SR^{10}$, $-S(\rightarrow O)R^{11}$ or $-S(\rightarrow O)_2R^{12}$ (wherein $R^4$ and $R^5$ are each independently hydrogen, linear lower alkyl, branched lower alkyl or cycloalkyl; $R^6$, $R^7$ and $R^8$ are each independently hydrogen, linear lower alkyl or branched lower alkyl; and $R^9$, $R^{10}$, $R^{11}$ and $R^{12}$ are each independently hydrogen, linear lower alkyl or branched lower alkyl, with the proviso that when A or B is a carbon atom optionally bearing a substituent, $R^4$ or $R^5$ together with the substituent of A or B may form a ring), or alternatively $X^1$ and $Y^1$ together with the carbon atoms to which they are bonded may form an optionally substituted, saturated or unsaturated ring which may contain oxygen, sulfur and/or nitrogen, and the substituents on the saturated or unsaturated ring may be united to form a saturated or unsaturated ring which may contain oxygen, sulfur and/or nitrogen;

E is a carbon or nitrogen; F and G are each independently carbon, nitrogen, sulfur or oxygen, with the carbon or nitrogen atom optionally bearing a substituent; and $X^2$ and $Y^2$ are each independently hydrogen, $-NR^{13}R^{14}$, $-CR^{15}R^{16}R^{17}$, $-OR^{18}$, $-SR^{19}$, $-S(\rightarrow O)R^{20}$ or $-S(\rightarrow O)_2R^{21}$ (wherein $R^{13}$ and $R^{14}$ are each independently hydrogen, linear lower alkyl, branched lower alkyl or cycloalkyl; $R^{15}$, $R^{16}$ and $R^{17}$ are each independently hydrogen, linear lower alkyl or branched lower alkyl; and $R^{18}$, $R^{19}$, $R^{20}$ and $R^{21}$ are each independently hydrogen, linear lower alkyl or branched lower alkyl), or alternatively $X^2$ and $Y^2$ may be united to form an optionally substituted, saturated or unsaturated ring which may contain oxygen, sulfur and/or nitrogen;

$X^3$ and $Y^3$ are each independently hydrogen, linear or branched lower alkyl, linear or branched lower alkoxy, cycloalkyl, aryl, heteroaryl, fluoroalkyl or halogeno; and the symbol ┈┈ represents a single bond or a double bond}, with the proviso that the cases wherein Z is

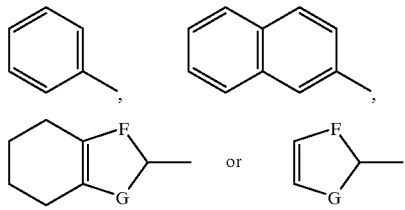

(wherein F and G are each as defined above) are excepted].

Preferable compounds of the present invention include mono- and polyenic carboxylic acid derivatives and physiologically acceptable salts thereof as described above wherein Z is a group represented by the formula:

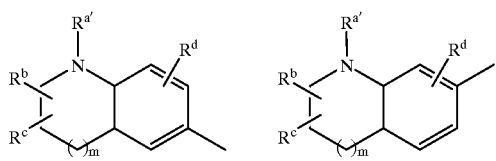

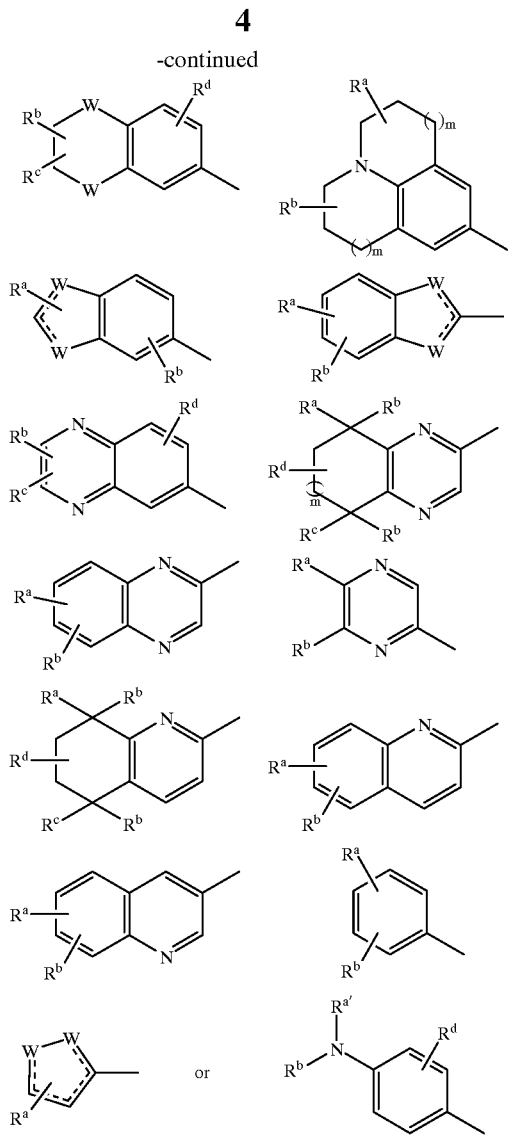

[wherein $R^a$, $R^b$, $R^c$ and $R^d$ are each independently hydrogen, linear or branched lower alkyl, linear or branched lower alkoxy, cycloalkyl, aryl, heteroaryl, fluoroalkyl or halogeno, or alternatively two of $R^a$, $R^b$, $R^c$ and $R^d$ may be united to form an optionally substituted, saturated or unsaturated ring which may contain oxygen, sulfur and/or nitrogen; $R^{a'}$ and $R^{b'}$ are each independently hydrogen, linear or branched lower alkyl, linear or branched lower alkoxy, cycloalkyl, aryl, heteroaryl or fluoroalkyl; m is a number of 0 to 3; m' is 0 or 1; and W is $>NR^e$, $>CR^eR^f$, $>SR^g$, $>S(\rightarrow O)$, $>S(\rightarrow O)_2$, O, N, $CR^e$ or S (wherein $R^e$, $R^f$ and $R^g$ are each independently hydrogen, linear or branched lower alkyl, linear or branched lower alkoxy, cycloalkyl, aryl, heteroaryl, fluoroalkyl or halogeno), with the proviso that both the W's in each group may be the same or different from each other].

Further, preferable compounds of the present invention include mono- and polyenic carboxylic acid derivatives and physiologically acceptable salts thereof as described above, wherein Z is a group represented by the formula:

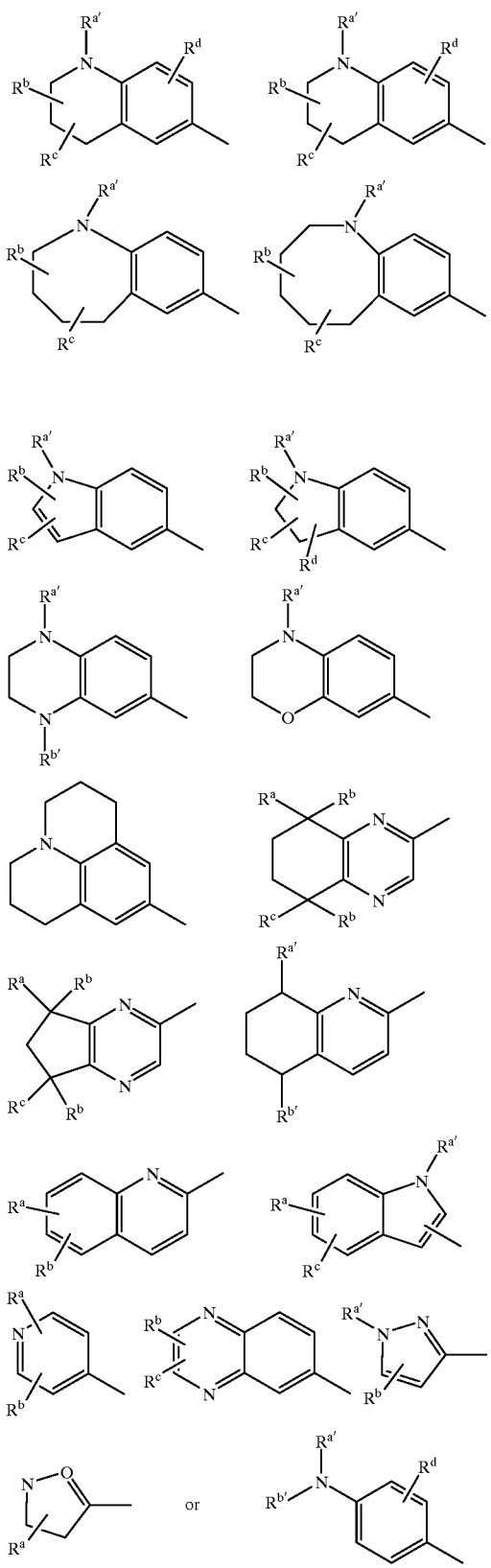

The carboxyl-protecting group as defined for $R^1$ in the present invention includes lower alkyl groups such as methyl, ethyl and propyl.

The term "linear lower alkyl" used in the definition of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^a$, $R^b$, $R^c$, $R^d$, $R^{a'}$, $R^{b'}$, $R^e$, $R^f$, $R^g$, $X^3$ and $Y^3$ refers to linear $C_1$–$C_6$ alkyl, examples of which include methyl, ethyl, propyl, butyl, amyl and pentyl. Among them, methyl, ethyl and propyl are preferable. The term "branched lower alkyl" used therein refers to isoproyl, isobutyl, sec-butyl, tert-butyl, amyl, isopentyl, neopentyl or the like, with isopropyl being preferable.

The term "linear lower alkoxy" used in the definition of $R^2$, $R^3$, $R^a$, $R^b$, $R^c$, $R^d$, $R^{a'}$, $R^{b'}$, $R^e$, $R^f$, $R^g$, $X^3$ and $Y^3$ refers to linear $C_1$–$C_6$ alkoxy, and examples thereof include methoxy, ethoxy, n-propoxy and n-butoxy. The term "branched lower alkoxy" used therein refers to isopropoxy, sec-butoxy or the like. The term "cycloalkyl" used in the definition of $R^4$, $R^5$, $R^{13}$, $R^{14}$, $R^a$, $R^b$, $R^c$, $R^d$, $R^{a'}$, $R^{b'}$, $R^e$, $R^f$, $R^g$, $X^3$ and $Y^3$ refers to $C_3$–$C_7$ cycloalkyl, and examples thereof include cyclopropyl, cyclobutyl, cyclopentyl, cyclohexyl and cycloheptyl. Further, the term "halogens" used in this description refers to fluoro, chloro or bromo.

The aryl as defined for $R^a$, $R^b$, $R^c$, $R^d$, $R^{a'}$, $R^{b'}$, $R^e$, $R^f$, $R^g$, $X^3$ and $Y^3$ includes phenyl and so on; the heteroaryl as defined therefor includes furyl and so on; and the fluoroalkyl as defined therefor includes trifluoromethyl and so on.

Further, n is an integer of 1 to 3, with the cases wherein n is 3 being most desirable.

Preferable examples of the compounds represented by the formula (1-I) include the following compounds:

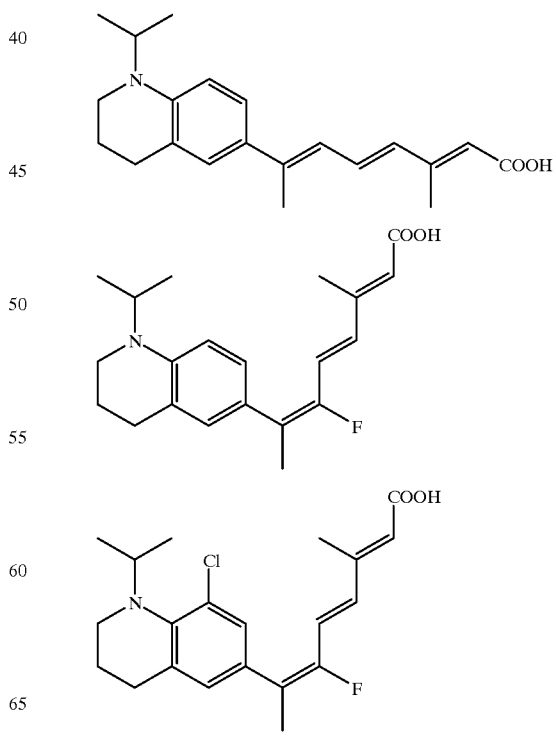

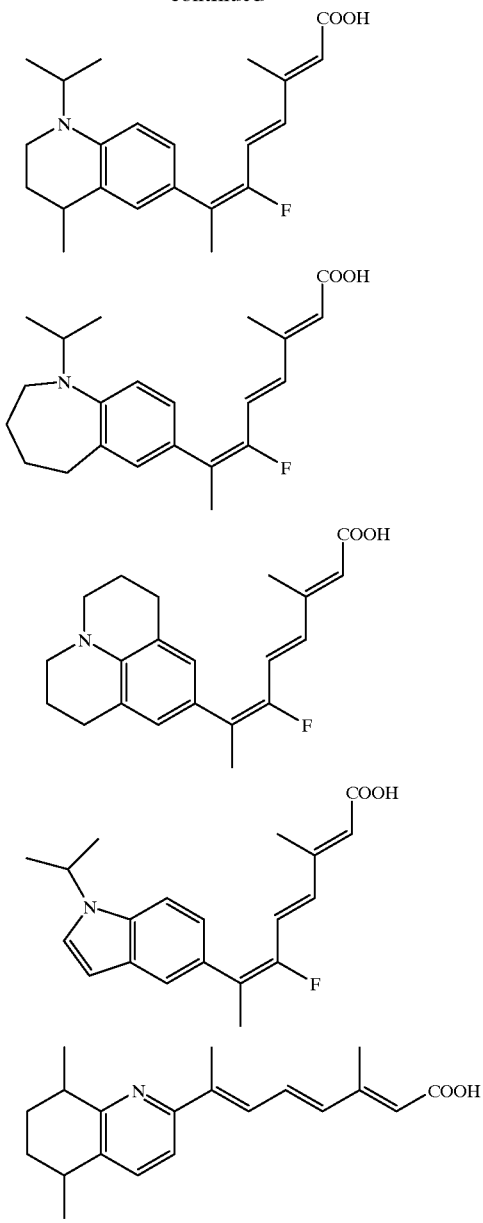

Further, the present invention relates also to mono- or polyenic carboxylic acid derivatives represented by the general formula (1-V) or physiologically acceptable salts thereof:

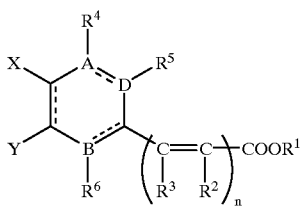

(1-V)

[wherein $R^1$ is hydrogen or a protecting group; $R^2$, $R^3$, $R^4$, $R^5$ and $R^6$ are each independently hydrogen, halogeno, linear lower alkyl, branched lower alkyl, linear lower alkoxy or branched lower alkoxy; X and Y are each independently $-NR^7R^8$, $-CR^9R^{10}R^{11}$, $-OR^{12}$, $-SR^{13}$, $-S(\to O)R^{14}$, or $-S(=O)_2R^{15}$ (wherein $R^7$ and $R^8$ are each independently hydrogen, linear lower alkyl, branched lower alkyl or cycloalkyl; $R^9$, $R^{10}$ and $R^{11}$ are each independently hydrogen, linear lower alkyl or branched lower alkyl; and $R^{12}$, $R^{13}$, $R^{14}$ and $R^{15}$ are each independently hydrogen, linear lower alkyl or branched lower alkyl, or alternatively $R^7$ or $R^8$ together with $R^4$ or $R^6$ may form a ring), or alternatively X and Y together with the carbon atoms to which they are bonded may form a ring which may contain a double bond; A, B and D are each carbon, nitrogen, sulfur or oxygen and D may be nil; n is an integer of 1 to 3; and the broken line moiety represents a single bond or a double bond].

Preferable examples of the above compounds according to claim 1 include mono- and polyenic carboxylic acid derivatives represented by the general formula (1-VI) and physiologically acceptable salts thereof:

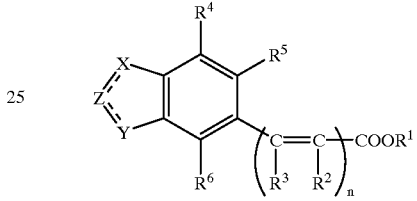

(1-VI)

[wherein X and Y are each independently $-NR^7R^8$ or $-CR^9R^{10}R^{11}$ (wherein $R^7$ and $R^8$ are each independently hydrogen, linear lower alkyl, branched lower alkyl or cycloalkyl; $R^9$, $R^{10}$ and $R^{11}$ are each independently hydrogen, linear lower alkyl or branched lower alkyl; and $R^{12}$, $R^{13}$, $R^{14}$ and $R^{15}$ are each independently hydrogen, linear lower alkyl or branched lower alkyl, or alternatively $R^7$ or $R^8$ together with $R^4$ or $R^6$ may form a ring); Z is $-(CR^{16}R^{17})_l-$, $-(CR^{18})_m=$ or $-(CR^{19}=CR^{20})_p-$ (wherein $R^{16}$, $R^{17}$, $R^{18}$, $R^{19}$ and $R^{20}$ are each independently hydrogen or lower alkyl; and l, m and p are each an integer of 1 to 4); n is an integer of 1 to 3; and the broken line moiety represents a single bond or a double bond].

The term "linear lower alkyl" used in the definition of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in the present invention refers to linear $C_1$–$C_6$ alkyl, examples of which include methyl, ethyl, propyl, butyl, amyl and pentyl. Among them, ethyl, ethyl and propyl are preferable. The term "branched lower alkyl" used therein refers to isopropyl, isobutyl, sec-butyl, tert-butyl, amyl, isopentyl or neopentyl, with isopropyl being preferable. The term "lower alkyl" used in the definition of $R^{16}$, $R^{17}$, $R^{18}$, $R^{19}$ and $R^{20}$ refers to methyl, ethyl, propyl, butyl, amyl, isopropyl, sec-butyl, tert-butyl or the like.

The term "linear lower alkoxy" used in the definition of $R^1$, $R^2$, $R^3$, $R^4$, $R^5$ and $R^6$ refers to linear $C_1$–$C_6$ alkoxy, and examples thereof include methoxy, ethoxy, n-propoxy and n-butoxy. The term "branched lower alkoxy" used therein refers to isopropoxy, sec-butoxy or the like. The term "cycloalkyl" used in the definition of $R^7$ and $R^8$ refers to $C_3$–$C_7$ cycloalkyl, and examples thereof include cyclopropyl, cyclobutyl, cyclopentyl, cyclohexyl and cycloheptyl. Further, the term "halogeno" used in this description refers to fluoro, chloro or bromo.

Specific examples of the above compounds wherein $R^7$ or $R^8$ together with $R^4$ or $R^6$ forms a ring include compounds as described above wherein X is $NR^7R^8$, Y is $CR^9R^{10}R^{11}$, $R^7$ and $R^8$ form rings, $R^{10}$ and $R^{11}$ are hydrogen, $R^8$ is n-propyl or the like, and $R^7$ and $R^4$ are united to form a ring, and such compounds are represented by, e.g.,

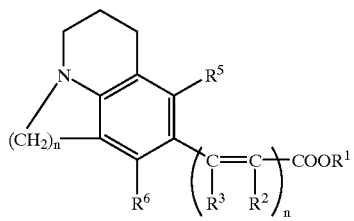

When A, B and D are each carbon, the formula (1-V) can be represented by

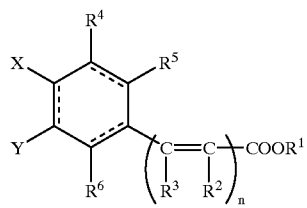

In the definition of Z in the general formula (1-VI), the cases wherein l is 1 or 2, m is 1 and p is 1 are preferable. Specific examples of the compounds according this preferable embodiment include those represented by the formulae:

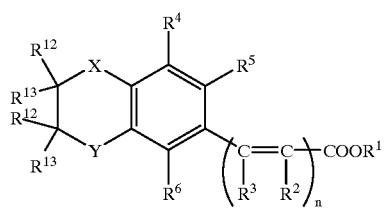

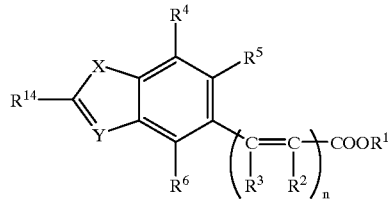

Further, it is most desirable that n is 3.

Preferable examples of the compounds represented by the general formula (1-V) include the following compounds:

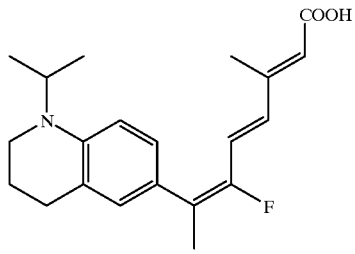

-continued

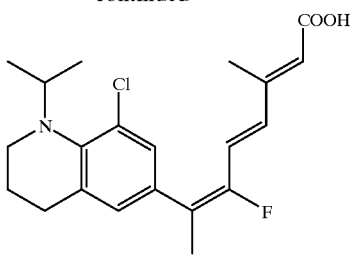

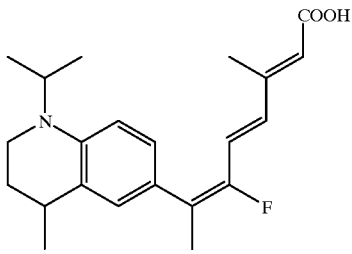

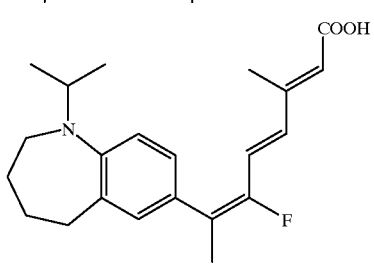

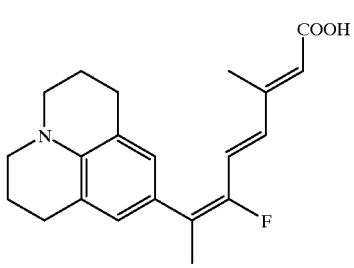

The second embodiment of the present invention relates to heterocyclic compounds represented by the following formula (2-I) or physiologically acceptable salts thereof:

(2-I)

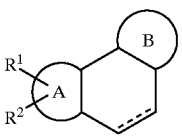

[wherein $R^1$ and $R^2$ are each independently hydrogen, lower alkyl, alkenylalkyl, alkynylalkyl, cycloalkyl, cycloalkylalkyl, lower alkoxyalkyl, aryl, heteroaryl or arylalkyl, or alternatively $R^1$ and $R^2$ may be united to form a 5- to 7-membered cycloalkyl group which is substituted with a lower alkyl group and may contain sulfur, oxygen, sulfinyl, sulfonyl or $NR^3$ (wherein $R^3$ is hydrogen or lower alkyl); the broken line moiety represents a single bond or a double bond; A represents

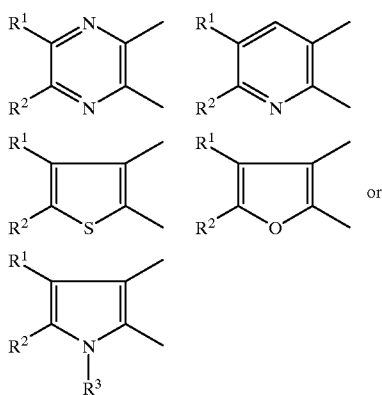

and

B represents

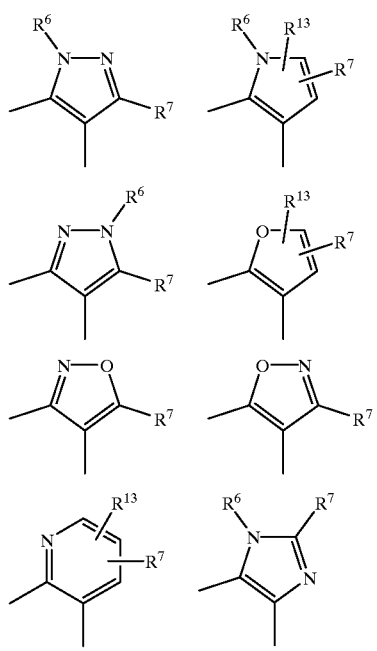

(wherein $R^6$ is hydrogen, lower alkyl, alkenylalkyl, alkynylalkyl, cycloalkyl, cycloalkylalkyl, lower alkoxyalkyl, aryl, heteroaryl, arylalkyl or heteroarylalkyl; $R^{13}$ is hydrogen, lower alkyl or lower alkoxy; $R^7$ is

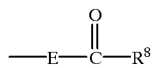

(wherein E is aryl, heteroaryl or

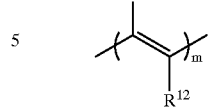

(wherein $R^{11}$ and $R^{12}$ are each hydrogen or lower alkyl; and m is an integer of 1 to 3); and $R^8$ is hydrogen, hydroxyl, lower alkoxy or —$NR^9R^{10}$ (wherein $R^9$ and $R^{10}$ are each independently hydrogen, hydroxyl, lower alkyl, lower alkoxy, hydroxyalkyl, aryl, hydroxyaryl or heteroaryl, or alternatively $R^9$ and $R^{10}$ together with the nitrogen atom to which they are bonded may form a ring which may contain nitrogen, oxygen or sulfur))].

Further, the present invention relates also to compounds represented by the general formula (2-II) or (2-III) or physiologically acceptable salts thereof:

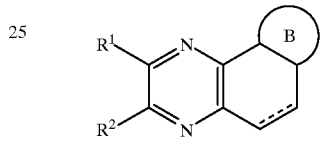

(2-II)

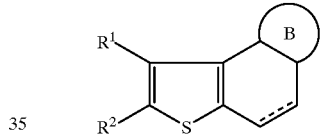

(2-III)

[wherein $R^1$ and $R^2$ are each independently hydrogen, lower alkyl, alkenylalkyl, alkynylalkyl, cycloalkyl, cycloalkylalkyl, lower alkoxyalkyl, aryl, heteroaryl or arylalkyl, or alternatively $R^1$ and $R^2$ may be united to form a 5- to 7-membered cycloalkyl group which is substituted with a lower alkyl group and may contain sulfur, oxygen, sulfinyl, sulfonyl or $NR^3$ (wherein $R^3$ is hydrogen or lower alkyl); the broken line moiety represents a single bond or a double bond; and B is a group represented by the formula:

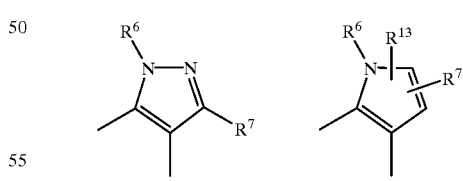

(wherein $R^6$ is hydrogen, lower alkyl, alkenylalkyl, alkynylalkyl, cycloalkyl, cycloalkylalkyl, lower alkoxyalkyl, aryl, heteroaryl, arylalkyl or heteroarylalkyl; $R^{13}$ is hydrogen, lower alkyl or lower alkoxy; and $R^7$ is

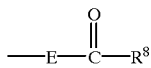

(wherein E is aryl, heteroaryl or

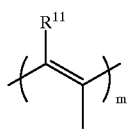

(wherein $R^{11}$ and $R^{12}$ are each hydrogen or lower alkyl; and m is an integer of 1 to 3); and $R^8$ is hydrogen, hydroxyl, lower alkoxy or —$NR^9R^{10}$ (wherein $R^9$ and $R^{10}$ are each independently hydrogen, hydroxyl, lower alkyl, lower alkoxy, hydroxyalkyl, aryl, hydroxyaryl or heteroaryl, or alternatively $R^9$ and $R^{10}$ together with the nitrogen atom to which they are bonded may form a ring which may contain nitrogen, oxygen or sulfur))].

The term "lower alkyl" used in the above definition for the compounds (2-I) to (2-III) according to the present invention refers to linear or branched $C_1$–$C_6$ alkyl, and examples thereof include methyl, ethyl, propyl, isopropyl, buty, isobutyl, sec-butyl, tert-butyl, amyl, isopentyl and neopentyl Among them, methyl, ethyl, propyl and isopropyl are preferable. The term "lower alkoxy" used in the definition of $R^8$, $R^9$, $R^{10}$ and $R^{13}$ refers to methoxy, ethoxy, n-propoxy, isopropoxy, n-butoxy or the like. The term "cycloalkyl" used in the defintion of $R^6$ refers to $C_3$–$C_7$ cycloalkyl, and examples thereof include cyclopropyl, cyclobutyl, cyclopentyl, cyclohexyl and cycloheptyl. The term "cycloalkylalkyl" used in the defintion of $R^6$ refers to one derived from the above cycloalkyl, and representative examples thereof include cyclopropylmethyl, cyclopentylmethyl, cyclohexylmethyl and cyclohexylethyl. The term "bridged cyclic hydrocarbyl" refers to adamantyl, adamantylmethyl or the like. The term "aryl" used in the definition of $R^6$, $R^9$ and $R^{10}$ refers to phenyl, naphthyl or the like, which may be substituted with lower alkyl such as methyl or ethyl, halogeno, lower alkoxy, hydroxyl or the like. The term "hydroxyaryl" used in the definition of $R^9$ and $R^{10}$ refers to a group comprising an aryl group such as phenyl or naphthyl and a hydroxyl group bonded thereto. The term "arylalkyl" used in the definition of $R^6$ refers to one derived from the above aryl group. Preferable examples thereof include benzyl and phenethyl. The above aryl group may be substituted with lower alkyl such as methyl or ethyl, halogeno, lower alkoxy, hydroxy or the like.

The term "heteroaryl" used in the definition of $R^6$ refers to a group derived from a heterocycle, and examples thereof include pyridyl, thiazolyl, pyrimidyl, furyl and thienyl.

The term "heteroarylalkyl" used in the defintion of $R^6$ refers to a group derived from the above heteroaryl, and examples thereof include pyridylmethyl and pyridylethyl.

The term "lower alkoxyalkyl" used in the definition of $R^6$ refers to a group derived from the above lower alkoxy, examples thereof including methoxyethoxy, methoxypropoxy and ethoxyethoxy.

As defined above with respect to $R^9$ and $R^{10}$, $R^9$ and $R^{10}$ together with the nitrogen atom to which they are bonded may form a ring which may contain nitrogen, oxygen or sulfur. Examples of such a ring include the following:

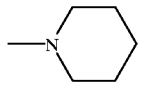 

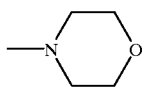 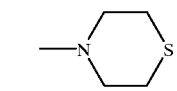

Compounds represented by the above general formula (2-I) or physiologically acceptable salts thereof, wherein B represents a substituted, 5- or 6-membered unsaturated heterocyclic structure containing one or two heteroatoms selected from the group consisting of nitrogen, oxygen and sulfur, with such a heterocyclic structure including

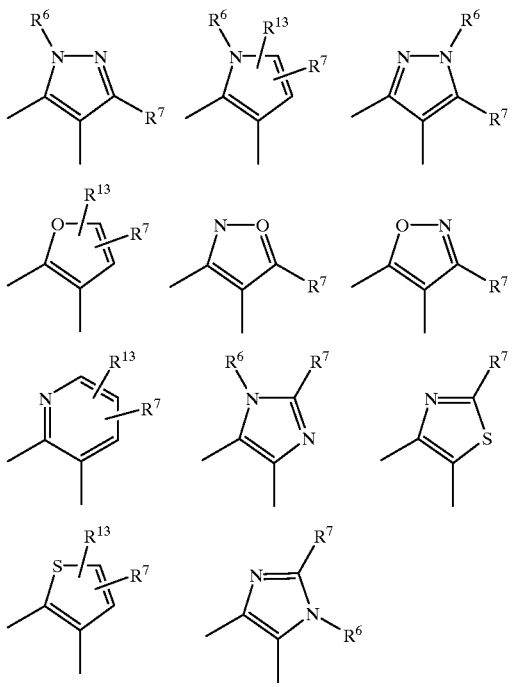

[wherein $R^{13}$ is hydrogen, lower alkyl or lower alkoxy; and $R^7$ is

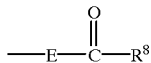

(wherein E is heteroaryl or

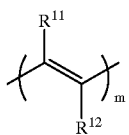

(wherein $R^{11}$ and $R^{12}$ are each hydrogen or lower alkyl; and m is an integer of 1 to 3); and $R^8$ is —$NR^9R^{10}$ (wherein $R^9$ and $R^{10}$ are each independently hydroxyaryl)].

Compounds represented by the above general formula (2-II) or (2-III) or physiologically acceptable salts thereof, wherein $R^1$ and $R^2$ are each independently hydrogen, alkenylalkyl, alkylalkyl, cycloalkyl, cycloalkylalkyl, lower alkoxyalkyl, aryl, heteroaryl or arylalkyl, with the cycloalkyl ring optionally contaning sulfur, oxygen, sulfinyl, sulfonyl or $NR^3$ (wherein $R^3$ is hydrogen or lower alkyl); and B is a group represented by the formula:

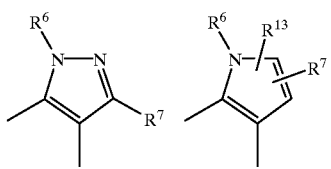 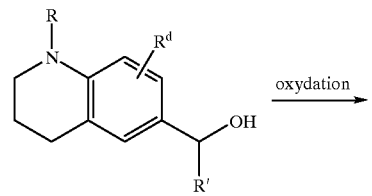

[wherein $R^{13}$ is hydrogen, lower alkyl or lower alkoxy; and $R^7$ is

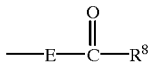

(wherein E is heteroaryl or

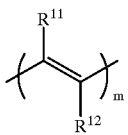

(wherein $R^{11}$ and $R^{12}$ are each independently hydrogen or lower alkyl; and m is an integer of 1 to 3))].

In the present invention, the term "physiologically acceptable salts" refers to conventional nontoxic salts. Examples thereof include inorganic acid salts such as hydrochloride, hydrobromide, sulfate and phosphate; organic acid salts such as acetate, maleate, oxalate, methanesulfonate, benzenesulfonate and toluenesulfonate; and amino acid salts such as argininate, aspartate and glutamate. Further, some of the carboxylic acid derivatives of the present invention take the form of salts with metals such as Na, K, Ca or Mg, and such salts are also included among the physiologically acceptable salts according to the present invention.

Preparation processes for preparing the compound according to the first embodiment of the present invention will now be described.

Preparation Process 1

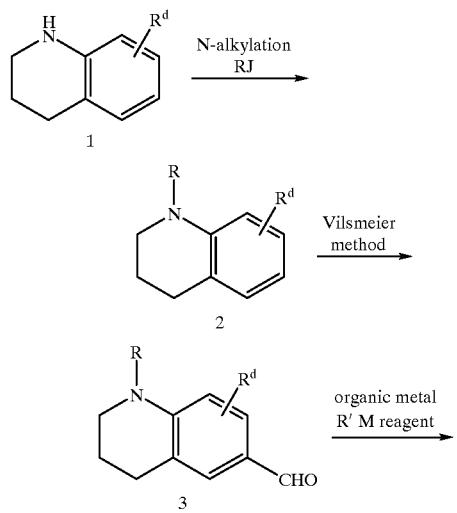

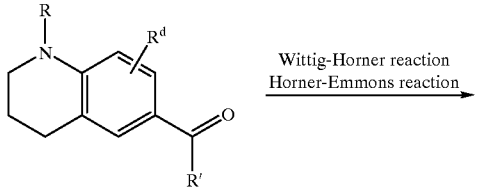
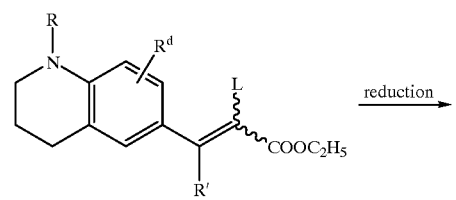
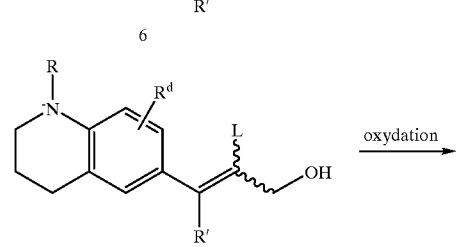
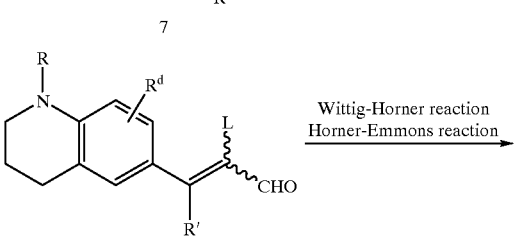
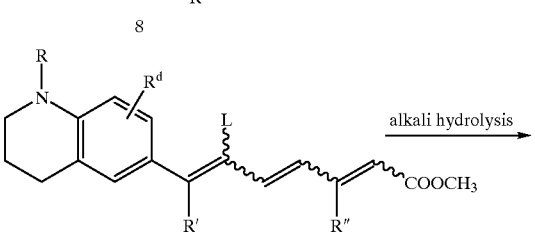
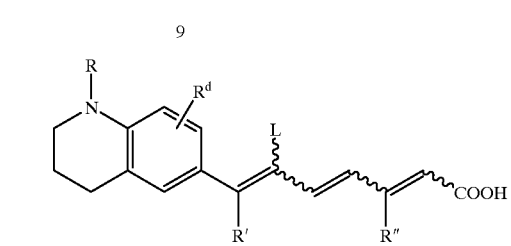

(in the above reaction scheme, $R^d$ is as defined above; R', R'' and R''' are each alkyl; J is halogeno; L is H or halogeno; and R'M is an organometallic reagent).

Preparation Process 1

(i) An N-alkylate represented by the general formula (2) is prepared by reacting the compound (1) with an alkyl halide in the presence of a base. Better results can be attained when potassium carbonate, sodium hydride or the like is used as the base. N,N-Dimethylformamide or tetrahydrofuran can be used as the solvent for this reaction. The reaction temperature may range from 0° C. to the boiling point of the solvent, preferably from 0° C. to 80° C.

(ii) An aldehyde represented by the general formula (3) is prepared from the N-alkylate (2) by the Vilsmeir process or the like.

(iii) An alcohol represented by the general formula (4) is prepared by reacting the aldehyde (3) with an organometallic reagent such as a Grignard reagent, organolithium reagent, organolithium-copper complex or the like. Ethers such as diethyl ether or tetrahydrofuran can be used as the solvent for this reaction. The reaction temperature may range from −78° C. to the boiling point of the solvent, preferably from −78° C. to 20° C.

(iv) A ketone represented by the general formula (5) is prepared by oxidizing the alcohol(4) with a suitable oxidizing agent. The use of activated manganese dioxide, PCC, PDC, Swern oxidizing agent or the like as the oxidizing agent gives good results. A solvent which is not oxidized with the oxidizing agent can be used for this reaction, such a solvent including dichloromethane and acetone. The reaction temperature may range from −78° C. to the boiling point of the solvent, preferably from −78° C. to 20° C.

(v) An acrylic acid derivative represented by the general formula (6) is prepared by subjecting the ketone (5) to the Wittig-Horner reaction or the Horner-Emmons reaction in the presence of a base. Better results can be attained; when sodium hydride, sodium alkoxide, n-butyllithium, potassium t-butoxide or lithium bistrimethylsilylamide is used as the base. The solvent usable in this reaction includes N,N-dimethylformamide, n-hexane, tetrahydrofuran and diethyl ether. The reaction temperature may range from −78° C. to the boiling point of the solvent, preferably −78° C. to 20° C.

(vi) An allyl alcohol represented by the general formula (7) is prepared by reducing the acrylic acid derivative (6) with a suitable reducing agent. Better results can be attained, when diisobutylaluminum hydride or lithium borohydride is used as the reducing agent. Tetrahydrofuran, dichloromethane or the like can be used as the-solvent for this reaction. The reaction temperature may range from −78° C. to the boiling point of the solvent, preferably from −78° C. to 20° C.

(vii) An aldehyde represented by the general formula (8) is prepared by oxidizing the allyl alcohol (7) in a similar manner to that employed in the step (iv).

(viii) A trienic carboxylic acid ester represented by the general formula (9) is prepared by subjecting the aldehyde (8) to the Wittig-Horner reaction or the Horner-Emmons reaction in a similar manner to that employed in the step (v).

(ix) A trienic carboxylic acid derivative represented by the general formula (10) is prepared by hydrolyzing the ester (9) in the presence of a base. Better results can be attained, when an aqueous solution of sodium hydroxide, potassium hydroxide or lithium hydroxide is used as the base. Alcohols such as methanol, ethanol and so on can be used as the solvent for this reaction. The reaction temperature may range from 0° C. to the boiling point of the solvent, preferably from 20° C. to the boiling point of the solvent.

Preparation Process 2

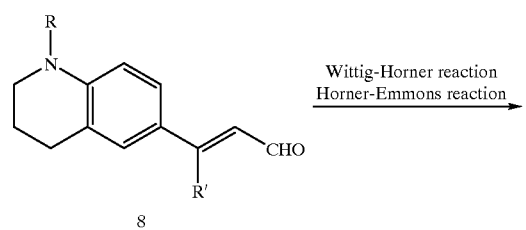

8

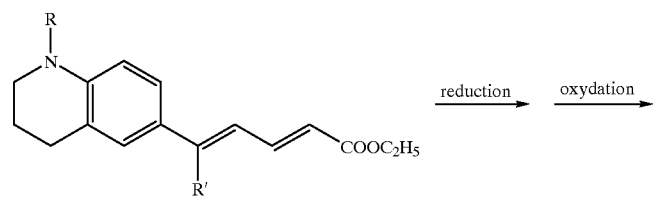

11

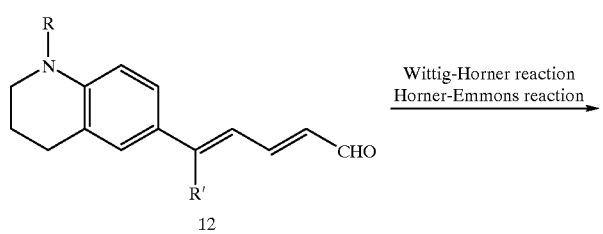

12

-continued

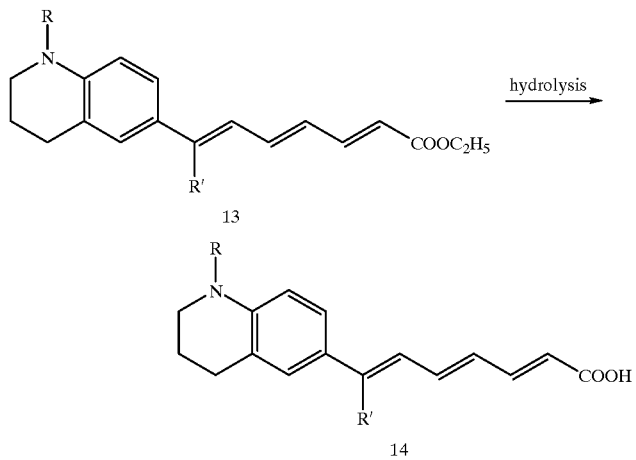

(wherein R and R' are each as defined above).

A dienic carboxylic acid ester represented by the general formula (11) is prepared by subjecting the aldehyde (8) to the Wittig-Horner reaction or the Horner-Emmons reaction in the presence of a base. Then, the obtained ester is converted into an aldehyde represented by the general formula (12) by conventional reduction and oxidation. This aldehyde is further subjected to the Witting-Horner reaction or the Horner-Emmons reaction in a similar manner to that described above to give a trienic carboxylic acid ester represented by the general formula (13). This ester is hydrolyzed by a conventional process into a trienic carboxylic acid represented by the general formula (14).

Preparation Process 3

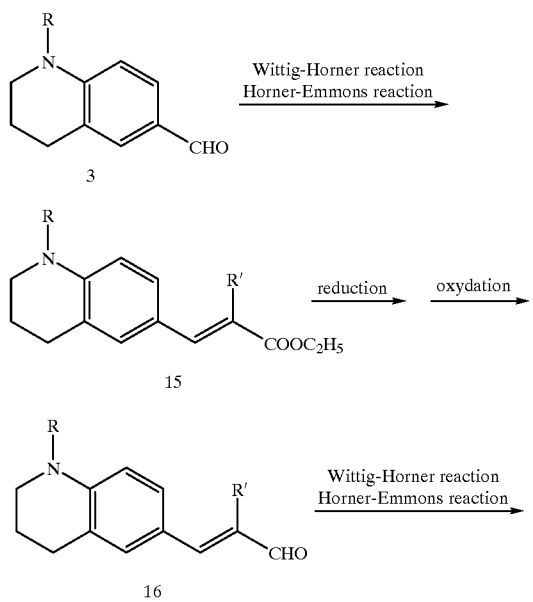

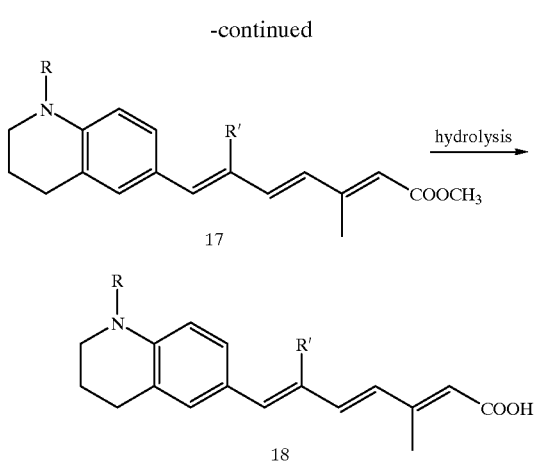

(wherein R and R' are each as defined above)

An acrylic acid derivative represented by the general formula (15) is prepared by subjecting the aldehyde (3) to the Wittig-Horner reaction or the Horner-Emmons reaction in the presence of a base. Then, the acid derivative is reduced and oxidized by conventional processes to give an aldehyde represented by the general formula (16). This aldehyde is subjected to the Wittig-Horner reaction or the Horner-Emmons reaction in a similar manner to that described above to give a trienic carboxylic acid ester represented by the general formula (17). A trienic carboxylic acid represented by the general formula (18) is obtained by hydrolyzing this ester in a conventional manner.

Representative processes for preparing the compounds according to the second embodiment of the present invention will now be described.

Preparation Process 4

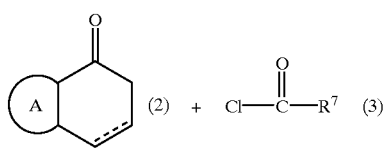

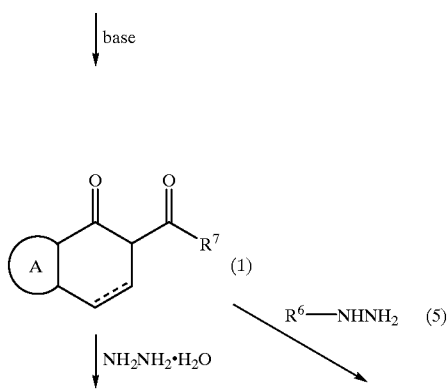

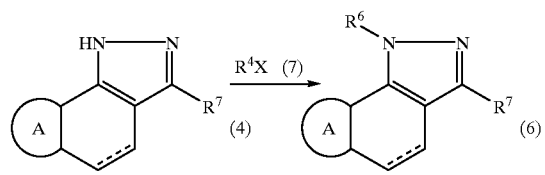

(in the reaction scheme, A, $R^6$, $R^7$ and broken line are each as defined above; and X is halogen).

A diketone represented by the general formula (1) is prepared by reacting the ketone (2) with an acid chloride (3) in the presence of a base. Better results can be attained when lithium diisopropylamide, lithium bistrimethylsilylamide or the like is used as the base. The solvent usable for this reaction includes ethers such as diethyl ether, tetrahydrofuran and dimethoxyethane. The reaction temperature may range from −78° C. to the boiling point of the solvent, preferably −78° C. to 20° C.

A pyrazole represented by the general formula (4) is prepared by reacting the diketone (1) with hydrazine hydrate, while a pyrazole represented by the general formula (6) is prepared by reacting the diketone (1) with a monosubstituted hydrazine (5) and removing undesirable isomers from the obtained product by crystallization or column chromatography.

Although this reaction can proceed without using any catalyst, it may be accelerated by the addition of an acid useful also as a dehydrating agent, with such an acid including hydrochloric acid, sulfuric acid, acetic acid and polyphosphoric acid.

The solvent for the reaction may, in principle, be any one which is unreactive with hydrazine. Examples of such a solvent include alcohols such as methanol, ethanol and isopropanol; aromatic hydrocarbons such as benzene, toluene and xylene; aprotic solvents such as dimethylformamide and dimethyl sulfoxide; and chlorinated hydrocarbons such as dichloromethane, chloroform and 1,2-dichloroethane. The reaction temperature may range from 0° C. to the boiling point of the solvent, preferably from room temperature to the boiling point of the solvent. Alternatively, a compound represented by the general formula (6) can be prepared by reacting the compound (4) with a halide represented by the general formula (7) in the presence of a base and removing simultaneously formed undesirable isomers from the obtained product by crystallization or column chromatography. Examples of the base usable in this reaction include alkali metal compounds such as potassium carbonate, sodium hydride and potassium hydride; and alkali metal alkoxides such as sodium methoxide, sodium ethoxide and potassium t-butoxide. The solvent usable for the reaction includes dimethylformamide, tetrahydrofuran and 1,2-dimethoxyethane. The reaction temperature may range from 0° C. to the boiling point of the solvent.

Preparation Process 5

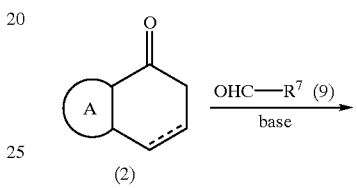

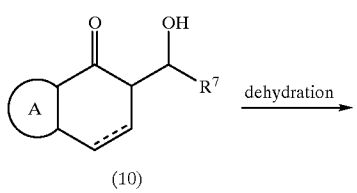

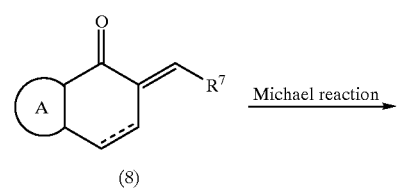

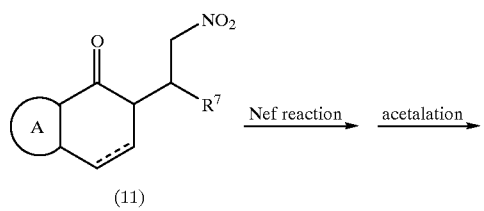

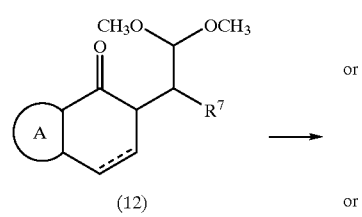

-continued

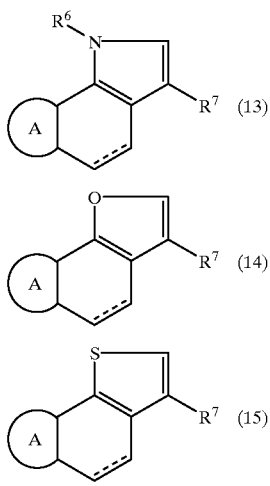

(in the above reaction scheme, $R^1$, $R^2$, $R^6$, $R^7$, A and n are each as defined above).

A compound represented by the general formula (8) is prepared by reacting a ketone represented by the general formula (2) with an aldehyde represented by the general formula (9) in the presence of a catalytic amount of a base to form an alcohol (10), and dehydrating this alcohol in the presence of an acid. The base to be used in the preparation of the alcohol (10) is preferably alkali hydroxide such as sodium hydroxide or potassium hydroxide. The solvent to be used therein includes methanol, ethanol, propanol, tetrahydrofuran and dimethylformamide. The reaction temperature may range from 0° C. to the boiling point of the solvent, preferably from 20° C. to 40° C.

The acid to be used in the above dehydration includes hydrochloric acid, sulfuric acid, p-toluene-sulfonic acid, trifluoroacetic acid, oxalic acid and phosphoric acid. The solvent to be used therein includes ethers such as diethyl ether, tetra-hydrofuran, 1,4-dioxane and 1,2-dimethoxyethane; and aromatic hydrocarbons such as benzene, toluene and xylene. The reaction temperature may range from 0° C. to the boiling point of the solvent. Some of the compounds (8) can be prepared directly from the compounds (2) without dehydration.

Then, the compound (8) can be converted into a compound (11) by reacting the compound (8) with a catalytic amount of a base in a solvent comprising nitromethane (and, if necessary, tetrahydrofuran, methanol, ethanol or the like, when the compound is difficultly soluble). The base to be used in this reaction includes N-benzyltrimethylammonium hydroxide, triethylamine and diisopropylethylamine. The reaction is conducted at a temperature ranging from 0° C. to the boiling point of the solvent, preferably from 0° C. to room temperature.

A ketal represented by the general formula (12) is prepared by converting the compound (11) into a γ-ketoaldehyde through the Nef reaction (Chem. Rev., 55, 137 (1955)) and converting this ketoaldehyde into a ketal. The conversion into a ketal can be attained by adding a mineral acid such as sulfuric acid or hydrochloric acid to methanol and adding the λ-ketoaldehyde to the obtained mixture. The reaction temperature may range from −78° C. to the boiling point of the solvent, preferably from −40° C. to room temperature.

A pyrrole (13) is prepared by reacting the dimethyl ketal (12) with a primary amine represented by the general formula $R^6$—$NH_2$. The solvent to be used in this reaction may be any one inert to the reaction. Preferable examples of such a solvent include aromatic hydrocarbons such as benzene, toluene and xylene; ethers such as tetrahydrofuran and 1,2-dimethoxy-ethane; and alcohols such as methanol and ethanol. The above reaction can proceed in such a solvent with which an acid is coexistent. The acid to be used is preferably one useful also as a dehydrating agent, and examples of such an acid include hydrochloric acid, sulfuric acid, glacial acetic acid and polyphosphoric acid.

The dimethyl ketal (12) can be converted also into a furan (14) by reating the with an acid. Sulfuric acid, polyphosphoric acid or the like is used as the acid, and the reaction is conducted at 0 to 100° C. Further, a thiophene (15) can be obtained by reacting the ketal (12) with a sulfide such as phosphorus pentasulfide or hydrogen sulfide. The solvent to be used in this reaction includes aromatic hydrocarbons such as benzene, toluene and xylene, and pyridine, while the reaction temperature may range from 0° C. to the boiling point of the solvent, preferably from 50° C. to the boiling point of the solvent.

Pharmacological Experimental Examples will now be described to illustrate the effects of the compounds according to the second embodiment of the present invention.

Experimental Example
Receptor Binding Assay Using Human Promyelocytic Leukemia Cell HL60

It is known that all-trans retinoic acid receptors (retinoic acid receptor: RAR) are is present in the nuclei of HL60 cells (Clara Nervi et al., Proc. Natl. Acad. Sci. U.S.A. 86, 5854(1989)). Therefore, the specific binding of all-trans retinoic acid for RAR was determined by the use of the nuclear extract fraction of HL60, and each test compound was examined for the ability to bind RAR by determining the inhibition against the specific binding.

The nuclear extract fraction was prepared as follows.

HL60 cells ($5 \times 10^8$) were suspended in 15 ml of solution A (sodium phosphate (pH7.4): 5 mM, monothio-glycerol: 10 mM, glycerol: 10% (v/v), phenylmethyl-sulfonyl fluoride (PMSF): 1 mM, aprotinin: 10 µg/ml, and leupeptin: 25 µg/ml). The obtained suspension was homogenized by the use of a homogenizer and centrifuged to remove the resulting supernatant. The sediment thus formed was suspended in 15 ml of solution B (Tris-HCl (pH8.5): 10 mM, monothioglycerol: 10 mM, glycerol: 10% (v/v), PMSF: 1 mM, aprotinin: 10 µg/ml, leupeptin: 25 µg/ml, and KCl: 0.8 M). The obtained suspension was allowed to stand at 4° C. for one hour, and subjected to ultracentrifugation (100,000 x g, 4° C., 1 hr). The obtained supernatant was stored as the nuclear extract fraction in a frozen state at −80° C. until the use (METHODS IN ENZYMOLOGY, 189, 248).

The receptor binding assay was conducted as follows.

180 µl of the above fraction and 10 µl of a dilution of all-trans retinoic acid or a test compound were added to each well of a 96-well plate made of polypropylene, followed by the addition of 10 µl of 10nM $^3$H-all-trans retinoic acid. The resulting plate was allowed to stand at 4° C. for 16 hours. A solution containing 3% of charcoal and 0.3% of dextran was added to the resulting reaction mixture. The mixture thus obtained was centrifuged to remove free $^3$H-all-trans retinoic acid. The radioactivity of the resulting supernatant was determined by the use of a scintillation counter. The specific binding of $^3$H-all-trans retinoic acid for RAR was determined by assuming the radioactivity found when 200 times as much all-trans retinoic acid was added to be the non-specific binding and subtracting it from the radioactivity determined above. The compounds which will be described below inhibited the binding of $^3$H-all-trans retinoic acid dependently on the concentration. The 50% inhibitory concentration of each test compound was calculated and the results are given in Table 1.

Antagonism Against All-trans Retinoic Acid in Inducing the Differentiation of HL60 Cells It is known that human promyelocytic leukemia cells HL60 differentiate into granulocyte-like cells in the presence of all-trans retinoic acid (Breitman, T., Selonick, S., and Collins, S., Proc. Natl. Acad. Sci. U.S.A. 77, 2936(1980)). In general, cells allow specific differentiation antigens to be expressed on the cell surfaces when they have achieved differentiation. When HL60 cells differentiate into granulocyte-like cells, CD11b which is a granulocyte/monocyte discriminating antigen is expressed on the cell surfaces (Fontana, J A., Reppuci, A., Durham, JP., and Mirand, D., Cancer Res. 46, 2469–2473 (1986)). The antagonism of a test compound against the differentiation into granulocyte-like cells induced by all-trans retinoic acid was studied by utilizing this phenomenon.

HL60 cells were cultured and maintained in a medium prepared by adding 10% of inactivated fetal bovine serum; 1 mM of sodium pyridinecarboxylate, 50 $\mu$M of $\beta$-mercaptoethanol, 100 IU/ml of penicillin and 100 $\mu$g/ml of streptomycin to RPMI1640 (culture medium formulated by Rosewell Park Memorial Institute).

An HL60 cell suspension ($1\times10^5$ cells/ml) was put in a 48-well plate in an amount of one ml per unit well, followed by the addition of all-trans retinoic acid in a concentration of 10 mM and a retinoid antagonist in various concentrations. The resulting mixtures were cultured in a 5% $CO_2$-air incubator for 5 days. After the completion of the culture, the cells in each well was recovered into a test tube, followed by the addition of an FITC-labeled monoclonal antibody against CD11b (which is a specific antigen against glanulocytes and monocytes). The resulting cell suspension was fixed with 0.2% paraformaldehyde. The fixed cell suspension thus obtained was examined for the content of CD11b-positive cells in the HL60 cell population of each well by flow cytometry (Miller, L J., Schwarting, R., and Springer, T A., J. Immunol. 137, 2891–2900 (1986)). The compounds which will be described below lowered the content of CD11b-positive cells induced by 10 nM all-trans retinoic acid dependently on the concentration. The 50% inhibitory concentration of each test compound was calculated and the results are given in Table 1.

TABLE 1

| Ex. No. | Receptor-binding assay using HL60 $IC_{50}$ (nM) | Antagonism against all-trans retinoic acid in inducing the differentiation of HL60 $IC_{50}$ (nM) |
|---|---|---|
| 4 | 20 | 74 |
| 5 | 5.4 | 39 |
| 8 | 17 | 470 |
| 9 | >50 | 880 |
| 13 | 12.5 | 29 |
| 14 | 13 | 130 |
| TD-550* | 50 | 2100** |
| TD-650* | >50 | 2600** |

*Cell Biol. Rev., 25, 209 (1991)
**antagonism against all-trans retinoic acid (3 nM)

It is apparent from the results of the above Experimental Examples that the compounds of the present invention have an extremely high ability to bind RARs and an antagonism against all-trans retinoic acid. Therefore, the compounds of the present invention can be expected to be efficacious against the following diseases:

various cornification anomalies, psoriasis, acne, leukoplakia, and xeroderma pigmentosum;

various alopeciae such as alopecia areata, seborrheic alopecia and cachectic alopecia;

postmenopausal osteoporosis, senile osteoporosis, idiopathic osteoporosis, diabetic osteopenia, rheumatoid osteopenia, renal osteomalacia and ectopic hyperostosis;

rheumatoid arthritis, osteoarthritis, and shoulder periarthritis;

activation of immunofunction in immunodefficiencies, infectious diseases in hypofunction or of fetus with cytomegalovirus, and opportunistic infection;

hyperthyroidism;

squamous cell carcinoma, bladder cancer, lung cancer, esophageal carcinoma, and head and neck cancer;

hyperkalemia; and pulmonary fibrosis, hepatic fibrosis, and hepatic cirrhosis.

The compounds of the present invention may be orally administered as preventive or therapeutic agents for these diseases in the form of tablet, powder, granule, capsule, syrup or the like, or may be parenterally administered in the form of suppository, injection, external preparation or drop.

Pharmaceutical preparations for oral or parenteral administration according to the present invention can be formulated by the use of conventional pharmaceutically acceptable carriers in a conventional manner.

Subcutaneous, intramuscular or intravenous injections or dropping injections according to the present invention can be formulated by conventional processes of adding a pH regulator, buffer, stabilizer or solubilizing agent to a base at need and, if necessary, freeze-drying the obtained mixture.

EXAMPLE

Figure 1:
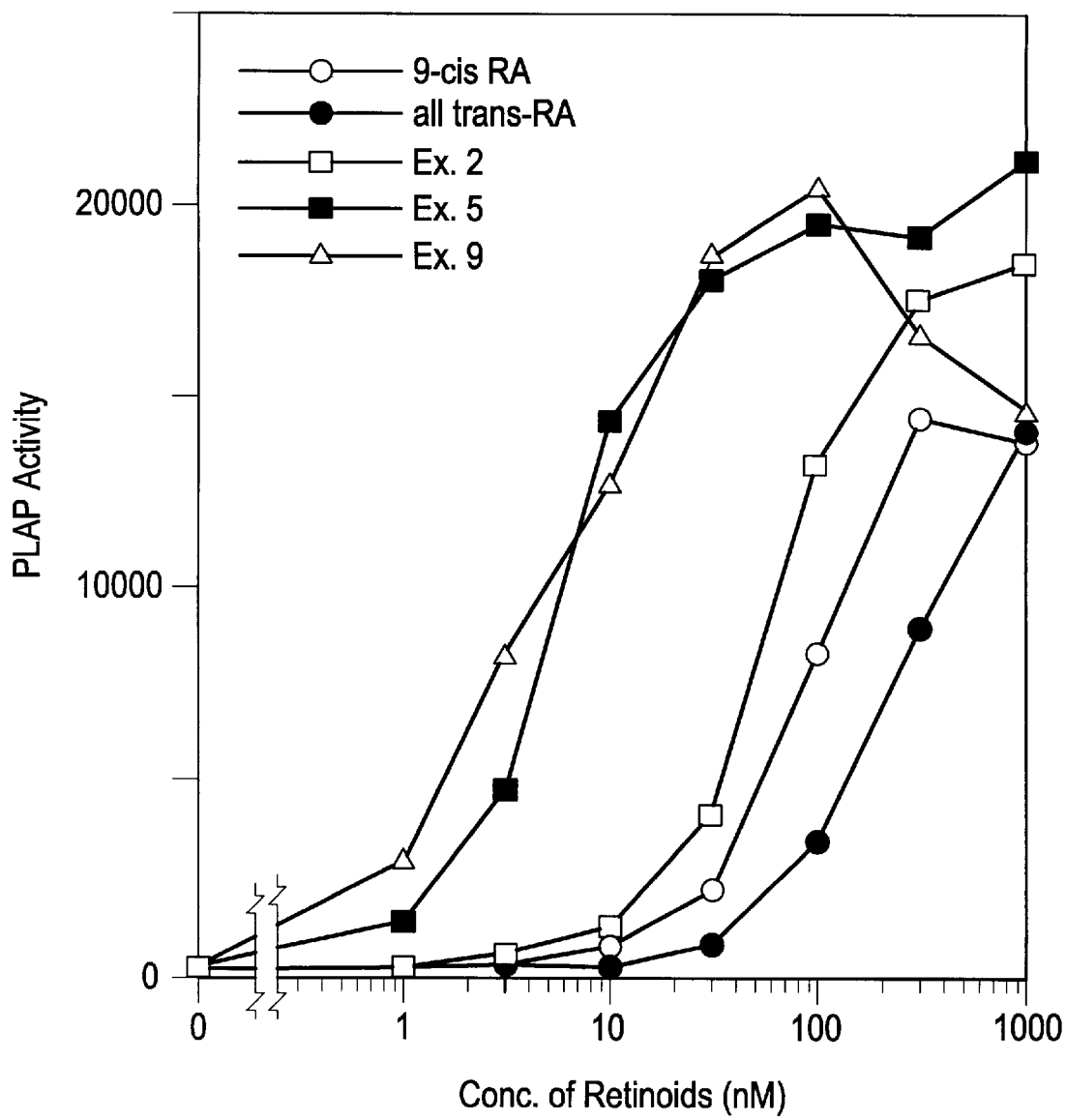
FIG. 1 shows the activities of the compounds of the present invention of accelerating transcription through retinoid X receptor $\alpha$ (RXR $\alpha$).

Examples 1 to 132 relate to the first embodiment of the present invention, and Examples 201 to 214 relate to the second embodiment thereof.

The compounds according to the first embodiment of the present invention will now be described in more detail, though the present invention is not limited by them.

In the Examples, Me and Et represent methyl and ethyl, respectively.

Example 1

Synthesis of Ethyl (E)-3-[1-(1-methylethyl)-1,2,3,4-tetrahydroquinolin-6-yl]-2-butenoate

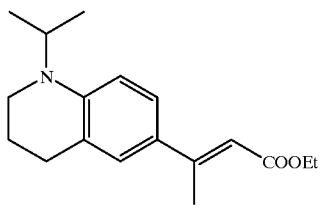

Step 1

Synthesis of 1-(1-methylethyl)-1,2,3,4-tetrahydroquinoline

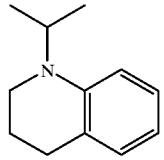

13.8 g (0.1 mmol) of 1,2,3,4-tetrahydroquinoline was dissolved in 60 ml of N,N-dimethylformamide, followed by the addition of 21.1 g (0.124 mmol) of isopropyl iodide and 20.6 g (0.208 mol) of potassium carbonate. The obtained mixture was stirred under heating at 60° C. for 5 hours. Water was added to the resulting reaction mixture, followed by the extraction with ethyl acetate. The organic phase was washed with a saturated aqueous solution of common salt, dried over anhydrous magnesium sulfate, and concentrated in a vacuum. The obtained residue was purified by silica gel column chromatography (3% ethyl acetate/n-hexane) to give 13.1 g of the title compound as a colorless oil.

$^1$H-NMR(400 MHz, CDCl$_3$) δ: 1.20(d, J=6.8 Hz, 6H), 1.92(tt, J=6.0, 6.0Hz, 2H), 2.76(t, J=6.0 Hz, 2H), 3.18(t, J=6.0 Hz, 2H), 4.13(hept., J=6.8 Hz, 1H), 6.57(dt, J=0.8, 7.2 Hz, 1H), 6.71(d, J=8.4 Hz, 1H), 6.97(dd, J=1.2, 7.6 Hz, 1H), 7.05–7.10(m, 1H).

Step 2

Synthesis of 1-(1-methylethyl)-1,2,3,4-tetrahydroquinoline-6-carbaldehyde

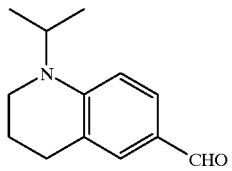

18.6 g (0.12 mol) of phosphorus oxychloride was dropped into 29.2 g (0.4 mol) of N,N-dimethylformamide under cooling with ice. The obtained mixture was stirred at room temperature for 30 minutes and cooled again on an ice bath. 17.5 g (0.1 mol) of 1-(1-methylethyl)-1,2,3,4-tetrahydroquinoline was gradually dropped into the resulting mixture. The mixture thus obtained was stirred at room temperature for one hour and poured onto ice-water. The resulting mixture was neutralized with an aqueous solution of sodium hydrogencarbonate and extracted with ethyl acetate. The organic phase was dried over anhydrous magnesium sulfate and concentrated in a vacuum. The residue was purified by silica gel column chromatography (10% ethyl acetate/n-hexane) to give 11.4 g of the title compound as a reddish-brown oil.

$^1$H-NMR(400 MHz, CDCl$_3$) δ: 1.23(d, J=6.5 Hz, 6H), 1.90(tt, J=6.0, 6.0 Hz, 2H), 2.75(t, J=6.0 Hz, 2H), 3.27(t, J=6.0 Hz, 2H), 4.20(hept., J=6.5 Hz, 1H), 6.69(d, J=9.0 Hz, 1H), 7.45(d, J=2.0 Hz, 1H), 7.55(dd, J=2.0, 9.0 Hz, 1H).

Step 3

Synthesis of 1-[1-(1-methylethyl)-1,2,3,4-tetrahydroquinolin-6-yl]ethanol

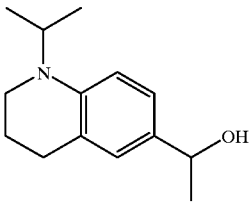

4.9 ml (15 mmol) of a 3.0M ethereal solution of methylmagnesium bromide was diluted with 15 ml of ether. An ethereal solution of 2.0 g (10 mmol) of 1-(1-methylethyl)-1,2,3,4-tetrahydroquinoline-6-carbaldehyde was dropped into the dilution prepared above at room temperature. The obtained mixture was stirred at room temperature for one hour, followed by the addition of an aqueous solution of ammonium chloride. The resulting mixture was extracted with thyl acetate. The organic phase was washed with a saturated aqueous solution of common salt, dried over anhydrous magnesium sulfate and concentrated in a vacuum to give 2.1 g of the title compound as a brown oil.

$^1$H-NMR(400 MHz, CDCl$_3$) δ: 1.19 (d, J=6.5 Hz, 6H), 1.48(d, J=6.5 Hz, 3H), 1.91 (tt, J=6.0, 6.0 Hz, 2H), 2.75(t, J=6.0 Hz, 2H), 3.17(t, J=6.0 Hz, 2H), 4.11(hept., J=6.5 Hz, 1H), 4.76(q, J=6.0 Hz, 1H), 6.67(d, J=9.0 Hz, 1H), 6.99(d, J=2.0 Hz, 1H), 7.07(dd, J=2.0, 9.0 Hz, 1H).

Step 4

Synthesis of 1-[1-(1-methylethyl)-1,2,3,4-tetrahydroquinolin-6-yl]ethanone

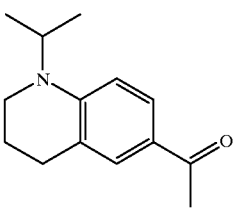

2.1 g of 1-[1-(1-methylethyl)-1,2,3,4-tetrahydroquinolin-6-yl]ethanol was dissolved in 10 ml of acetone, followed by the addition of 10 g of activated manganese dioxide. The obtained mixture was stirred at room temperature for 16 hours and filtered though Celite to remove the manganese dioxide. The filtrate was concentrated in a vacuum and the obtained residue was purified by silica gel column chromatography (10% ethyl acetate/n-hexane) to give 1.3 g of the title compound as a pale-yellow crystal.

$^1$H-NMR(400 MHz, CDCl$_3$) δ: 1.22(d, J=6.5 Hz, 6H), 1.89(tt, J=6.0, 6.0 Hz, 2H), 2.48(s, 3H), 2.75(t, J=6.0 Hz, 2H), 3.24(t, J=6.0 Hz, 2H), 4.19(hept., J=6.5 Hz, 1H), 6.63(d, J=9.0 Hz, 1H), 7.59(dd, J=2.0 Hz, 1H), 7.69(dd, J=2.0, 9.0 Hz, 1H).

Step 5

Synthesis of Ethyl (E)-3-[1-(1-methylethyl)-1,2,3,4-tetrahydroquinolin-6-yl]-2-butenoate

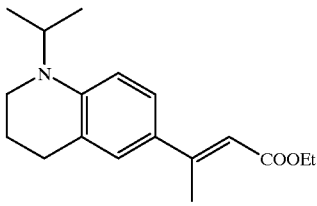

2.0 g (60%, 51 mmol) of sodium hydride was suspended in 10 ml of N,N-dimethylformamide, and 11.3 g (51 mmol) of ethyl diethylphosphonoacetate was dropped into the suspension under cooling with ice. The obtained mixture was stirred at room temperature for one hour, followed by the addition of 5.5 g (25 mmol) of 1-[1-(1-methylethyl)-1,2,3,4-tetra-hydroquinolin-6-yl]ethanone. The obtained mixture was stirred at 60° C. for 48 hours, followed by the addition of water. The mixture thus obtained was extracted with ethyl acetate. The organic phase was washed with a saturated aqueous solution of common salt, dried over anhydrous magnesium sulfate and concentrated in a vacuum. The residue was purified by silica gel column chromatography (4% ethyl acetate/n-hexane) to give 4.0 g of the title compound as a colorless oil.

$^1$H-NMR(400 MHz, CDCl$_3$) δ: 1.20 (d, J=6.5 Hz, 6H), 1.31(t, J=6.5 Hz, 3H), 1.90 (tt, J=6.0, 6.0 Hz, 6.0 Hz, 2H), 2.55(d, J=1.0 Hz, 3H), 2.74(t, J=6.0 Hz, 2H), 3.20(t, J=6.0 Hz, 2H), 4.13(hept., J=6.5 Hz, 1H), 4.19(q, J=6.5 Hz, 2H), 6.09(q, J=1.0 Hz, 1H), 6.64(d, J=9.0 Hz, 1H), 7.18(d, J=2.0 Hz, 1H), 7.29(dd, J=2.0, 9.0 Hz, 1H).

Example 2

Synthesis of (E,E,E)-7-[1-(1-methylethyl)-1,2,3,4-tetrahydroquinolin-6-yl]-3-methyl-octa-2,4,6-trienoic acid

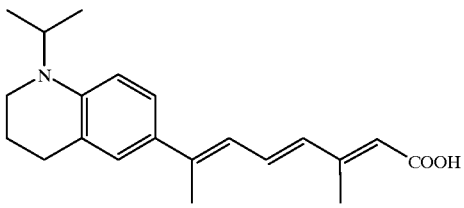

Step 1

Synthesis of (E)-3-[1-(1-methylethyl)-1,2,3,4-tetrahydroquinolin-6-yl]-2-butenol

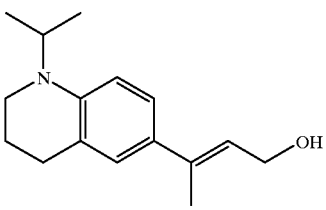

1.0 g of ethyl (E)-3-[1-(1-methylethyl)-1,2,3,4-tetrahydroquinolin-6-yl]-2-butenoate prepared in Example 1 was dissolved in 20 ml of tetrahydrofuran. The obtained solution was cooled to −70° C., followed by the gradual addition of 7.0 ml (10.5 mmol) of a 1.5M solution of diisobutylaluminum hydride in toluene. The obtained mixture was stirred for 2 hours, followed by the addition of an aqueous solution of ammonium chloride. The obtained mixture was extracted with ethyl acetate. The organic phase was washed with a saturated aqueous solution of common salt, dried over anhydrous magnesium sulfate and concentrated in a vacuum to give 650 mg of the title compound as a colorless oil.

$^1$H-NMR(400 MHz, CDCl$_3$) δ: 1.18(d, J=6.5 Hz, 6H), 1.90(tt, J=6.0, 6.0 Hz, 2H), 2.04(s, 3H), 2.74(t, J=6.0 Hz, 2H), 3.17 (t, J=6.0 Hz, 2H), 4.11(hept., J=6.5 Hz, 1H), 4.18(bd, J=5.0 Hz, 1H), 4.33(d, J=6.5 Hz, 2H), 5.89(t, J=6.5 Hz, 1H), 6.64(d, J=8.5 Hz, 1H), 7.06(d, J=2.0 Hz, 1H), 7.14(dd, J=2.0, 8.5 Hz, 1H).

Step 2

(E)-3-[1-(1-Methylethyl)-1,2,3,4-tetrahydroquinolin-6-yl]-2-butenal

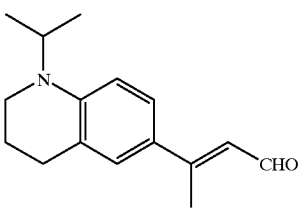

650 mg of (E)-3-[1-(1-methylethyl)-1,2,3,4-tetrahydroquinolin-6-yl]-2-butenal was dissolved in 10 ml of acetone, followed by the addition of 3.5 g of activated manganese dioxide. The obtained mixture was stirred at room temperature for 16 hours and filtered through Celite to remove the manganese dioxide. The filtrate was concentrated in a vacuum, and the obtained residue was purified by silica gel column chromatography (10% ethyl acetate/hexane) to give 400 mg of the title compound as a pale-yellow oil.

$^1$H-NMR(400 MHz, CDCl$_3$) δ: 1.22(d, J=6.5 Hz, 6H), 1.91(tt, J=6.0, 6.0 Hz, 2H), 2.50(s, 3H), 2.75(t, J=6.0 Hz, 3H), 3.23(t, J=6.0 Hz, 2H), 4.16(hept., J=6.5 Hz, 1H), 6.41(d, J=8.0 Hz, 1H), 6.67(d, J=9.0 Hz, 1H), 7.26(d, J=2.0 Hz, 1H), 7.38(dd, J=2.0, 9.0 Hz, 1H), 10.10(d, J=8.0 Hz, 1H).

Step 3

Methyl (E,E,E)-7-[1-(1-methylethyl)-1,2,3,4-tetrahydroquinolin-6-yl]-3-methyl-octa-2,4,6-trienoate

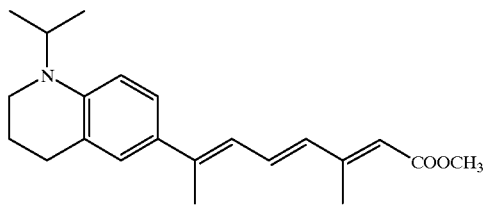

56 mg (2.46 mmol) of metallic sodium was added to methanol to prepare a methanolic solution of sodium methoxide. This solution was concentrated in a vacuum and suspended in N,N-dimethylformamide, followed by the addition of 560 mg (2.14 mmol) of triethyl 3-methyl-4-phosphonocrotonate under cooling with ice. After 30 minutes, 400 mg (1.64 mmol) of (E)-3-[1-(1-methylethyl)-1,2,3,4-tetrahydroquinolin-6-yl]-2-butenal was added to the mixture obtained above. The mixture thus obtained was stirred for one hour, followed by the addition of an aqueous solution of ammonium chloride. The obtained mixture was extracted with ethyl acetate. The organic phase was dried over anhydrous magnesium sulfate and concentrated in a vacuum. The obtained residue was purified by silica gel column chromatography (15% ethyl acetate/n-hexane) to give 330 mg of the title compound as a reddish-brown oil.

$^1$H-NMR(400 MHz, CDCl$_3$) δ: 1.20(d, J=6.8 Hz, 6H), 1.91(tt, J=6.0, 6.0 Hz, 2H), 2.20(s, 3H), 2.38(d, J=0.8 Hz, 3H), 2.75(t, J=6.0 Hz, 2H), 3.19(t, J=6.0 Hz, 2H), 3.72(s, 3H), 4.15(hept., J=6.8 Hz, 1H), 5.77(s, 1H), 6.32(d, J=15.2 Hz, 1H), 6.53(d, J=11.2 Hz, 1H), 6.65(d, J=8.8 Hz, 1H), 7.06(dd, J=11.2, 15.2 Hz, 1H), 7.15(d, J=2.4 Hz, 1H), 7.25(dd, J=2.4, 8.8 Hz, 1H).

Step 4

(E,E,E)-7-[1-(1-Methylethyl)-1,2,3,4-tetrahydroquinolin-6-yl]-3-methyl-octa-2,4,6-trienoic acid

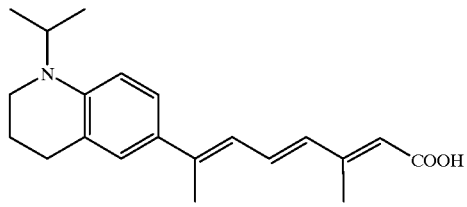

330 mg of methyl (E,E,E)-7-[1-(1-methylethyl)-1,2,3,4-tetrahydroquinolin-6-yl]-3-methylocta-2,4,6-trienoate was dissolved in 10 ml of ethanol, followed by the addition of 1.0 ml of a 5N aqueous solution of sodium hydroxide. The obtained mixture was heated at 60° C. for one hour and adjusted to pH5 by adding 6N hydrochloric acid under cooling with ice. The crystals thus precipitated were recovered by filtration and recrystallized from ethanol to give 100 mg of the title compound as orange crystals.

$^1$H-NMR(400 MHz, CDCl$_3$) δ: 1.19(d, J=6.5 Hz, 6H), 1.91(tt, J=6.0, 6.0 Hz, 2H), 2.21(s, 3H), 2.39(s, 3H), 2.75(t, J=6.0 Hz, 2H), 3.19(t, J=6.0 Hz, 2H), 4.13(hept., J=6.5 Hz, 1H), 5.79(s, 1H), 6.35(d, J=15.0 Hz, 1H), 6.55(d, J=11.0 Hz, 1H), 6.66(d, J=9.0 Hz, 1H), 7.10(dd, J=15.0, 11.0 Hz, 1H), 7.16(d, J=2.0 Hz, 1H), 7.26(dd, J=9.0, 2.0 Hz, 1H).

Example 3

Synthesis of (E,E,E)-7-[1-(1-methylethyl)-1,2,3,4-tetrahydroquinolin-6-yl]-octa-2,4,6-trienoic acid

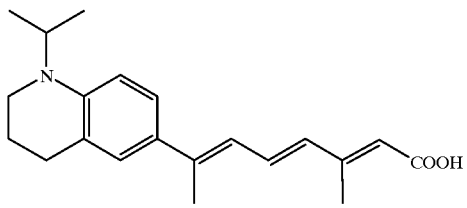

Step 1

Synthesis of Ethyl (E,E)-5-[1-(1-methylethyl)-1,2,3,4-tetrahydroquinolin-6-yl]-hexa-2,4 -dienoate

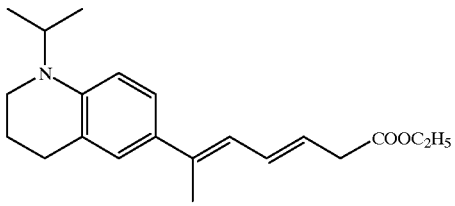

The title compound was prepared by the use of (E) -3- [1-(1-methylethyl) -1,2,3,4-tetrahydroquinolin-6-yl]-2-butenal in a similar manner to that described in Step 5 of Example 1.

$^1$H-NMR(400 MHz, CDCl$_3$) δ: 1.19(d, J=6.8 Hz, 6H), 1.31(t, J=7.2 Hz, 3H), 1.87–1.94(m, 2H), 2.24(d, J=1.2 Hz, 3H), 2.75(t, J=6.0 Hz, 2H), 3.20(t, J=6.0 Hz, 2H), 4.15(hept., J=7.2 Hz, 1H), 4.22(q, J=7.2 Hz, 2H), 5.88(d, J=14.8 Hz, 1H), 6.54(dt, J=0.8, 12.0 Hz, 1H), 6.65(d, J=9.2 Hz, 1H), 7.17(d, J=2.8 Hz, 1H), 7.27(dd, J=2.4, 8.8 Hz, 1H), 7.77(dd, J=12.0, 15.2 Hz, 1H).

Step 2

Synthesis of (E,E)-5-[1-(1-methylethyl)-1,2,3,4-tetrahydroquinolin-6-yl]-hexa-2,4-dienal

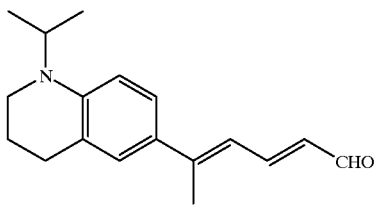

The title compound was prepared by the use of ethyl (E,E)-5-[1-(1-methyethyl)-1,2,3,4-tetrahydroquinolin-6-yl]-hexa-2,4-dienoate in a similar manner to that described in Steps 1 and 2 of Example 2.

$^1$H-NMR(400 MHz, CDCl$_3$) δ: 1.21(d, J=6.4 Hz, 7H), 1.87–1.95(m, 2H), 2.29(d, J=1.2 Hz, 3H), 2.76(t, J=6.0 Hz,

2H), 3.22(t, J=6.0 Hz, 2H), 4.13(hept., J=7.2 Hz, 1H), 6.19(dd, J=8.0, 14.8 Hz, 1H), 6.66(d, J=8.8 Hz, 1H), 6.71(bd, J=11.6 Hz, 1H), 7.22(d, J=2.4 Hz, 1H), 7.33(dd, J=2.4, 8.8 Hz, 1H), 7.59(dd, J=12.0, 14.8 Hz, 1H), 9.60(d, J=8.0 Hz, 1H).

Step 3

Synthesis of Ethyl (E,E,E)-7-[1-(1-methylethyl)-1,2,3,4-tetrahydroquinolin-6-yl]-octa-2,4,6-trienoate

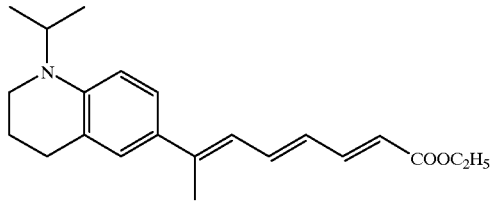

The title compound was prepared in a similar manner to that described in Step 5 of Example 1.

$^1$H-NMR(400 MHz, CDCl$_3$) δ: 1.19(d, J=6.8 Hz, 6H), 1.30(t, J=7.2 Hz, 3H), 1.91(tt, J=5.6, 6.4 Hz, 2H), 2.19(s, 3H), 2.75(t, J=6.4 Hz, 2H), 3.19(t, J=5.6 Hz, 2H), 4.13(hept., J=6.8 Hz, 1H), 4.21(q, J=7.2 Hz, 2H), 5.83(d, J=15.2 Hz, 1H), 6.36(dd, J=11.6, 14.4 Hz, 1H), 6.53(d, J=11.2 Hz, 1H), 6.65(d, J=9.2 Hz, 1H), 6.86(dd, J=11.6, 14.4 Hz, 1H), 7.15(d, J=2.4 Hz, 1H), 7.25(dd, J=2.4, 8.8 Hz, 1H), 7.42(dd, J=11.6, 14.8 Hz, 1H).

Step 4

Synthesis of (E,E,E)-7-[1-(1-methylethyl)-1,2,3,4-tetrahydroquinolin-6-yl]-octa-2,4,6-trienoic Acid

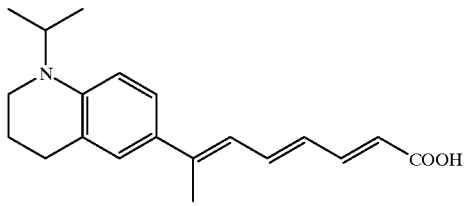

The title compound was prepared in a similar manner to that described in Step 4 of Example 2.

$^1$H-NMR(400 MHz, DMSO-d$_6$) δ: 1.11(d, J=6.8 Hz, 6H), 1.74–1.83(m, 2H), 2.10(s, 3H), 2.65(t, J=6.4 Hz, 2H), 3.12(t, J=5.6 Hz, 2H), 4.09(hept., J=6.8 Hz, 1H), 5.79(d, J=15.2 Hz, 1H), 6.41(dd, J=11.6, 14.0 Hz, 1H), 6.55(d, J=12.0 Hz, 1H), 6.64(d, J=9.2 Hz, 1H), 7.08(dd, J=12.0, 14.4 Hz, 1H), 7.12(d, J=2.0 Hz, 1H), 7.20(dd, J=2.0, 9.2 Hz, 1H), 7.25(dd, J=11.6, 15.2 Hz, 1H).

Example 4

Synthesis of (E,E,E)-7-[1-(1-methylethyl)-1,2,3,4-tetrahydroquinolin-6-yl]-3,6-dimethyl-hepta-2,4,6-trienoic Acid

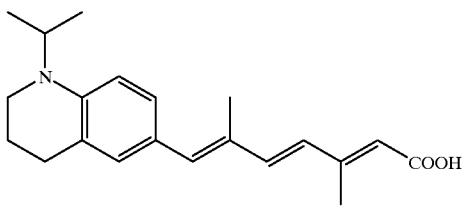

Step 1

Synthesis of ethyl (E)-3-[1-(1-methylethyl)-1,2,3,4-tetrahydroquinolin-6-yl]-2-methyl-2-acrylate

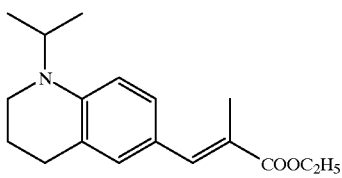

800 mg (60%, 20 mmol) of sodium hydride was suspended in 10 ml of N,N-dimethylformamide. 4.8 g (20 mmol) of triethyl phosphono-2-propionate was dropped into the suspension under cooling with ice. The obtained mixture was stirred at room temperature for one hour, followed by the addition of 2.0 g of 1-(1-methylethyl)-1,2,3,4-tetrahydroquinoline-6-carbaldehyde. The obtained mixture was stirred at room temperature for one hour, followed by the addition of water. The mixture thus obtained was extracted with ethyl acetate, and the organic phase was washed with a saturated aqueous solution of common salt, dried over anhydrous magnesium sulfate, and concentrated in a vacuum. The residue was purified by silica gel column chromatography (10% ethyl acetate/n-hexane) to give 2.0 g of the title compound as a colorless oil.

$^1$H-NMR(400 MHz, CDCl$_3$) δ: 1.19(d, J=6.8 Hz, 6H), 1.33(t, J=6.4 Hz, 3H), 1.90(tt, J=6.0, 6.0 Hz, 2H), 2.15(s, 3H), 2.74(t, J=6.0 Hz, 2H), 3.20(t, J=6.0 Hz, 2H), 4.14(hept., J=6.8 Hz, 1H), 4.23(q, J=6.4 Hz, 2H), 6.68(bd, J=8.8 Hz, 1H), 7.24(bd, J=8.8 Hz, 1H), 7.56(bs, 1H).

Step 2

Synthesis of 3-[1-(1-methylethyl)-1,2,3,4-tetrahydroquinolin-6-yl]-2-methyl-2-propenal

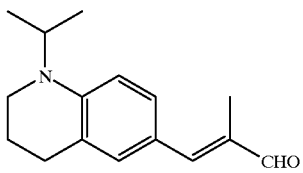

The title compound was prepared in a similar manner to that described in Steps 1 and 2 of Example 2.

$^1$H-NMR(400 MHz, CDCl$_3$) δ: 1.22(d, J=6.8 Hz, 6H), 1.91(tt, J=6.0, 6.0 Hz, 2H), 2.09(d, J=1.2 Hz, 3H), 2.76(t,

J=6.4 Hz, 2H), 3.25(t, J=6.0 Hz, 2H), 4.17(hept., J=6.8 Hz, 1H), 6.71(d, J=8.8 Hz, 1H), 7.06(s, 1H), 7.22(d, J=2.4 Hz, 1H), 7.35(dd, J=2.4, 8.8 Hz, 1H), 9.44(s, 1H).

Step 3

Synthesis of methyl (E,E,E)-7-[1-(1-methylethyl)-1,2,3,4-tetrahydroquinolin-6-yl]-3,6-dimethyl-hepta-2,4,6-trienoate

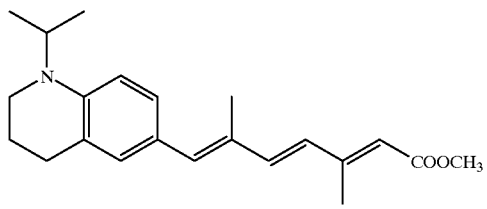

The title compound was prepared in a similar manner to that described in Step 3 of Example 2.

$^1$H-NMR(400 MHz, CDCl$_3$) δ: 1.19(d, J=6.8 Hz, 6H), 1.91(tt, J=6.0, 6.0 Hz, 2H), 2.08(s, 3H), 2.37(s, 3H), 2.74(t, J=6.0 Hz, 2H), 3.19(tt, J=6.0 Hz, 2H), 3.19(tt, J=6.0 Hz, 2H), 3.71(s, 3H), 4.15(hept., J=6.8 Hz, 1H), 5.80(s, 1H), 6.27(d, J=15.6 Hz, 1H), 6.55(s, 1H), 6.66(d, J=8.8 Hz, 1H), 6.80(d, J=15.2 Hz, 1H), 7.00(d, J=1.2 Hz, 1H), 7.12(dd, J=1.2, 8.4 Hz, 1H).

Step 4

Synthesis of (E,E,E)-7-[1-(1-methylethyl)-1,2,3,4-tetrahydroquinolin-6-yl]-3,6-dimethyl-hepta-2,4,6-trienoic acid

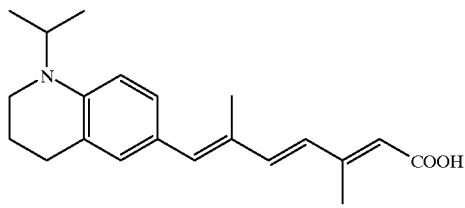

The title compound was prepared in a similar manner to that described in Step 4 of Example 2.

$^1$H-NMR(400 MHz, CDCl$_3$) δ: 1.20(d, J=6.8 Hz, 6H), 1.91(tt, J=6.0 Hz, 2H), 2.10(s, 3H), 2.39(s, 3H), 2.74(t, J=6.0 Hz, 2H), 3.20(t, J=6.0 Hz, 2H), 4.14(hept., J=6.8 Hz, 1H), 5.83(s, 1H), 6.30(d, J=15.6 Hz, 1H), 6.57(s, 1H), 6.67(d, J=8.8 Hz, 1H), 6.84(d, J=15.6 Hz, 1H), 7.01(d, J=1.2 Hz, 1H), 7.13(dd, J=1.6, 8.4 Hz, 1H).

Example 5

Synthesis of (E,E,E)-7-[1-(1-methylethyl)-1,2,3,4-tetrahydroquinolin-6-yl]-6-fluoro-3-methyl-octa-2,4,6-trienoic acid

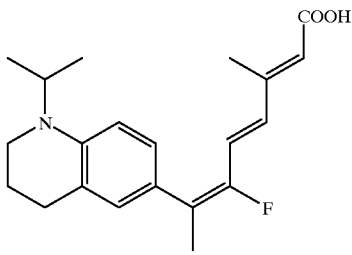

Step 1

Synthesis of ethyl (E)-3-[1-(1-methylethyl)-1,2,3,4-tetrahydroquinolin-6-yl]-2-fluoro-2-butenoate

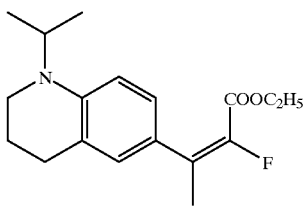

450 mg (60%, 12 mmol) of sodium hydride was suspended in 10 ml of N,N-dimethylformamide. 3.3.g (14 mmol) of ethyl 2-fluoro-diethylphosphonoacetate was dropped into the suspension under cooling with ice. The obtained mixture was stirred under cooling with ice for 30 minutes, followed by the addition of 2.0 g (9.2 mmol) of 1-[1-(1-methylethyl)-1,2,3,4-tetrahydro-quinolin-6-yl) ethanone. The obtained mixture was stirred under cooling with ice for one hour, followed by the addition of an aqueous solution of ammonium chloride. The obtained mixture was extracted with ethyl acetate, and the organic phase was washed with a saturated aqueous solution of common salt, dried over anhydrous magnesium sulfate and concentrated in a vacuum. The residue was purified by silica gel column chromatography to give 2.3 g of the title compound as a colorless oil.

$^1$H-NMR(400 MHz, CDCl$_3$) δ: 1.14(t, J=7.2 Hz, 3H), 1.18(d, J=6.8 Hz, 6H), 1.89(tt, J=6.0, 6.0 Hz, 2H), 2.12(d, J=4.8 Hz, 3H), 2.71(t, J=6.0 Hz, 2H), 3.17(t, J=6.0 Hz, 2H), 4.12(hept., J=6.8 Hz, 1H), 4.12(q, J=7.2 Hz, 2H), 6.61(d, J=8.4 Hz, 1H), 6.81(d, J=2.0 Hz, 1H), 6.92(dd, J=2.4, 8.8 Hz, 1H).

Step 2

Synthesis of (E)-3-[1-(1-methylethyl)-1,2,3,4-tetrahydroquinolin-6-yl]-2-fluoro-2-butenol

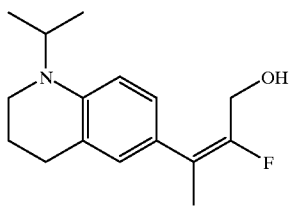

The title compound was prepared in a similar manner to that described in Step 1 of Example 2.

$^1$H-NMR(400 MHz, CDCl$_3$) δ: 1.18(d, J=6.8 Hz, 6H), 1.90(tt, J=6.0 Hz, 2H), 1.98(d, J=3.6 Hz, 3H), 2.72(t, J=6.0 Hz, 2H), 3.17(t, J=6.0 Hz, 2H), 4.09(hept., J=6.8 Hz, 1H), 4.22(dd, J=6.0, 22.4 Hz, 2H), 6.63(d, J=8.4 Hz, 1H), 6.82(d, J=2.4 Hz, 1H), 6.91(dd, J=2.4, 8.4 Hz, 1H).

Step 3

Synthesis of (E)-3-[1-(1-methylethyl)-1,2,3,4-tetrahydroquinolin-6-yl]-2-fluoro-2-butenal

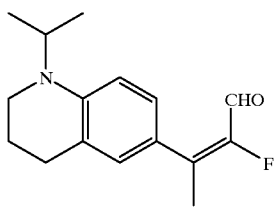

The title compound was prepared in a similar manner to that described in Step 2 of Example 2.

$^1$H-NMR(400 MHz, CDCl$_3$) δ: 1.21(d, J=6.8 Hz, 6H), 1.91(tt, J=6.0, 6.0 Hz, 2H), 2.25(d, J=3.6 Hz, 3H), 2.73(t, J=6.0 Hz, 2H), 3.22(t, J=6.0 Hz, 2H), 4.12(hept., J=6.8 Hz, 1H), 6.66(d, J=8.8 Hz, 1H), 6.92(d, J=2.4 Hz, 1H), 7.02(dd, J=2.4, 8.4 Hz, 1H), 9.35(d, J=19.6 Hz, 1H).

Step 4

Synthesis of methyl (E,E,E)-7-[1-(1-methylethyl)-1,2,3,4-tetrahydroquinolin-6-yl]-6-fluoro-3-methyl-octa-2,4,6-trienoate

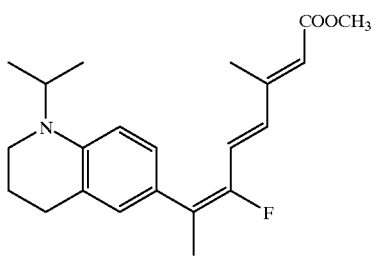

The title compound was prepared in a similar manner to that described in Step 3 of Example 2.

$^1$H-NMR(400 MHz, CDCl$_3$) δ: 1.21(d, J=6.8 Hz, 6H), 1.92(tt, J=6.0, 6.0 Hz, 2H), 2.12(d, J=3.6 Hz, 3H), 2.21(d, J=0.8 Hz, 3H), 2.74(t, J=6.0 Hz, 2H), 3.20(t, J=6.0 Hz, 2H), 3.70(s, 3H), 4.13(hept., J=6.8 Hz, 1H), 5.84(s, 1H), 6.50(d, J=15.6 Hz, 1H), 6.66(d, J=8.4 Hz, 1H), 6.68(dd, J=15.6, 26.4 Hz, 1H), 6.87(d, J=2.4 Hz, 1H), 6.95(dd, J=2.4, 8.4 Hz, 1H).

Step 5

Synthesis of (E,E,E)-7-[1-(1-methylethyl)-1,2,3,4-tetrahydroquinolin-6-yl]-6-fluoro-3-methyl-octa-2,4,6-trienoic acid

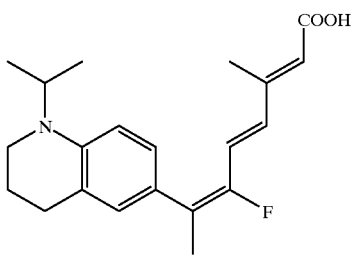

The title compound was prepared in a similar manner to that described in Step 4 of Example 2.

$^1$H-NMR(400 MHz, CDCl$_3$) δ: 1.21(d, J=6.4 Hz, 6H), 1.92(tt, J=6.0, 6.0 Hz, 2H), 2.12(d, J=3.2 Hz, 3H), 2.21(s, 3H), 2.74(t, J=6.0 Hz, 2H), 3.20((t, J=6.0 Hz, 2H), 5.86(s, 1H), 6.52(d, J=15.6 Hz, 1H), 6.66(d, J=8.4 Hz, 1H), 6.71(dd, J=15.6, 26.4 Hz, 1H), 6.87(d, J=2.0 Hz, 1H), 6.95(dd, J=2.4, 8.8 Hz, 1H).

Example 6

Synthesis of (E,E,Z)-7-[1-(1-methylethyl)-1,2,3,4-tetrahydroquinolin-6-yl]-6-fluoro-3-methyl-octa-2,4,6-trienoic acid

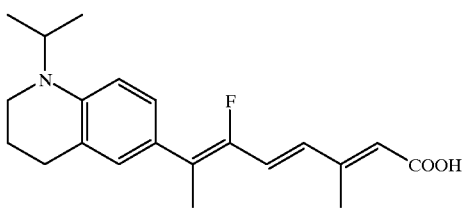

Step 1

Synthesis of Ethyl (Z)-3-[1-(1-methylethyl)-1,2,3,4-tetrahydroquinolin-6-yl]-2-fluoro-2-butenoate

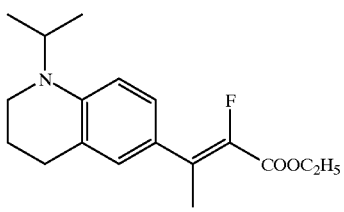

The title compound was prepared in a similar manner to that described in Step 1 of Example 5 through separation and purification by silica gel column chromatography.

$^1$H-NMR(400 MHz, CDCl$_3$) δ: 1.20(d, J=6.4 Hz, 6H), 1.37(t, J=7.2 Hz, 3H), 1.91(tt, J=6.0, 6.0 Hz, 2H), 2.43(d,

J=3.2 Hz, 3H), 2.73(t, J=6.0 Hz, 2H), 3.20(t, J=6.0 Hz, 2H), 4.13(hept., J=6.4 Hz, 1H), 4.31(q, J=7.2 Hz, 2H), 6.66(d, J=8.8 Hz, 1H), 7.13(d, J=2.0 Hz, 1H), 7.23(dd, J=2.0, 8.8 Hz, 1H).

Step 2

Synthesis of (Z)-3-[1-(1-methylethyl)-1,2,3,4-tetrahydroquinolin-6-yl]-2-fluoro-2-butenal

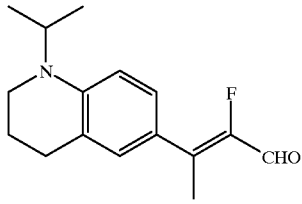

The title compound was prepared in a similar manner to that described in Steps 1 and 2 of Example 2.

$^1$H-NMR(400 MHz, CDCl$_3$) δ: 1.21(d, J=6.8 Hz, 6H), 1.91(tt, J=6.0, 6.0 Hz, 2H), 2.42(d, J=3.2 Hz, 3H), 2.75(t, J=6.0 Hz, 2H), 3.23(t, J=6.0 Hz, 2H), 4.17(hept., J=6.8 Hz, 1H), 6.68(d, J=9.2 Hz, 1H), 7.32(d, J=3.2 Hz, 1H), 7.44(dd, J=3.2, 9.2 Hz, 1H), 9.89(d, J=16.8 Hz, 1H).

Step 3

Methyl (E,E,Z)-7-[1-(1-methylethyl)-1,2,3,4-tetrahydroquinolin-6-yl)-6-fluoro-3-methyl-octa-2,4,6-trienoate

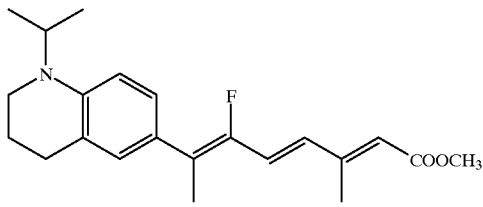

The title compound was prepared in a similar manner to that described in Step 3 of Example 2.

$^1$H-NMR(400 MHz, CDCl$_3$) δ: 1.19(d, J=6.4 Hz, 6H), 1.92(tt, J=6.0, 6.0 Hz, 2H), 2.13(d, J=2.8 Hz, 3H), 2.37(d, J=0.8 Hz, 3H), 2.74(t, J=6.0 Hz, 2H), 3.19(t, J=6.0 Hz, 2H), 3.72(s, 3H), 4.14(hept., J=6.4 Hz, 1H), 5.87(s, 1H), 6.56(d, J=15.2 Hz, 1H), 6.66(d, J=9.2 Hz, 1H), 6.83(dd, J=15.2, 26.4 Hz, 1H), 7.16(d, J=1.2 Hz, 1H), 7.26(dd, J=1.2, 9.2 Hz, 1H).

Step 4

Synthesis of (E,E,Z)-7-[1-(1-methylethyl)-1,2,3,4-tetrahydroquinolin-6-yl]-6-fluoro-3-methyl-octa-2,4,6-trienoic acid

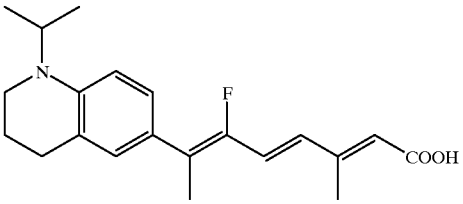

The title compound was prepared in a similar manner to that described in Step 4 of Example 2.

$^1$H-NMR(400 MHz, CDCl$_3$) δ: 1.19(d, J=6.4 Hz, 6H), 1.92(tt, J=6.0, 6.0 Hz, 2H), 2.13(d, J=2.8 Hz, 3H), 2.37(bs, 3H), 2.74(t, J=6.0 Hz, 2H), 3.19(t, J=6.0 Hz, 2H), 4.12(hept., J=6.4 Hz, 1H), 5.84(bs, 1H), 6.58(dd, J=15.2 Hz, 1H), 6.66(d, J=8.4 Hz, 1H), 6.83(dd, J=15.2, 26.4 Hz, 1H), 7.16(bs, 1H), 7.25–7.26(m, 1H).

The following compounds were prepared in a similar manner to that described above.

Example 7

Ethyl (E)-3-[1-(1-methylethyl)-4-methyl-1,2,3,4-tetra-hydroquinolin-6-yl]-2-fluoro-2-butenoate $^1$H-NMR(400 MHz, CDCl$_3$) δ: 1.13(t, J=7.2 Hz, 3H), 1.18(d, J=6.4 Hz, 3H), 1.20(d, J=6.4 Hz, 3H), 1.24(d, J=6.8 Hz, 3H), 1.60–1.70(m, 1H), 1.86"1.96(m, H), 2.13(d, J=4.8 Hz, 3H), 2.78–2.88(m, 1H), 3.14–3.23(m, 2H), 4.05"4.18 (m, 3H), 6.63(d, J=8.4 Hz, 1H), 6.89(d, J=2.4 Hz, 1H), 6.93(dd, J=2.4, 8.8 Hz, 1H).

Example 8

Methyl (E,E,E)-7-[1-(1-methylethyl)-4-methyl-1,2,3,4-tetrahydroquinolin-6-yl]-6-fluoro-3-methyl-octa-2,4,6-trienoate $^1$H-NMR(400 MHz, CDCl$_3$) δ: 1.21(d, J=6.0 Hz, 3H), 1.22(d, J=6.0 Hz, 3H), 1.26(d, J=7.2 Hz, 3H), 1.62–1.72(m, 1H), 1.89–1.97(m, 1H), 2.13(d, J=4.0 Hz, 3H), 2.21(d, J=0.8 Hz, 3H), 2.81–2.90(m, 1H), 3.13–3.25(m, 2H), 3.70(s, 3H), 4.14(hept., J=6.4 Hz, 1H), 5.84(s, 1H), 6.50(d, J=16.0 Hz, 1H), 6.68(d, J=8.4 Hz, 1H), 6.69(dd, J=15.6, 26.0 Hz, 1H), 6.94(d, J=2.4 Hz, 1H), 6.98(dd, J=2.4, 8.4 Hz, 1H).

Example 9

(E,E,E)-7-[1-(1-Methylethyl)-4-methyl-1,2,3,4-tetra-hydroquinolin-6-yl]-6-fluoro-3-methyl-octa-2,4,6-trienoic acid $^1$H-NMR(400 MHz, CDCl$_3$) δ: 1.21(d, J=5.6 Hz, 3H), 1.22(d, J=6.4 Hz, 3H), 1.27(d, J=6.8 Hz, 3H), 1.62–1.71(m, 1H), 1.90–1.98(m, 1H), 2.14(d, J=3.6 Hz, 3H), 2.22(s, 3H), 2.81–2.90(m, 1H), 3.17–3.23(m, 2H), 4.14(hept., J=6.8 Hz, 1H), 5.87(bs, 1H), 6.53(d, J=15.6 Hz, 1H), 6.68(d, J=8.8 Hz, 1H), 6.73(dd, J=16.0, 26.8Hz, 1H), 6.95(d, J=2.4 Hz, 1H), 6.98(dd, J=2.4, 8.8Hz, 1H).

Example 10

Ethyl (E)-3-[1-(1-methylethyl)-4-methyl-1,2,3,4-tetra-hydroquinolin-6-yl]-2-butenoate $^1$H-NMR(400 MHz, CDCl$_3$) δ: 1.20(d, J=6.4 Hz, 3H), 1.21(d, J=6.8 Hz, 3H), 1.27(d, J=6.8 Hz, 3H), 1.31(t, J=7.2

Hz, 3H), 1.63–1.71(m, 1H), 1.87–1.95(m, 1H), 2.56(d, J=1.2 Hz, 3H), 2.81–2.91(m, 1H), 3.16–3.24(m, 2H), 4.15(hept., J=6.4 Hz, 1H), 4.19(q, J=7.2 Hz, 2H), 6.10(d, J=0.8 Hz, 1H), 6.66(d, J=9.6 Hz, 1H), 7.26–7.30(m, 2H).

Example 11

Methyl (E,E,E)-7-[1-(1-methylethyl)-4-methyl-1,2,3,4-tetrahydroquinolin-6-yl]-3-methyl-octa-2,4,6-trienoate $^1$H-NMR(400 MHz, CDCl$_3$) δ: 1.19(d, J=6.4 Hz, 3H), 1.21(d, J=6.4 Hz, 3H), 1.28(d, J=7.2 Hz, 3H), 1.61–1.72(m, 1H), 1.88–1.98(m, 1H), 2.21(d, J=0.8 Hz, 3H), 2.38(d, J=0.8 Hz, 3H), 2.83–2.92(m, 1H), 3.18–3.22(m, 2H), 3.71(s, 3H), 4.13(hept., J=6.4 Hz, 1H), 5.77(s, 1H), 6.33(d, J=14.8 Hz, 1H), 6.53(bd, J=11.2 Hz, 1H), 6.67(d, J=8.4 Hz, 1H), 7.06(dd, J=11.2, 14.8 Hz, 1H), 7.23–7.27(m, 2H).

Example 12

(E,E,E)-7-[1-(1-Methylethyl)-4-methyl-1,2,3,4-tetrahydroquinolin-6-yl]-3-methyl-octa-2,4,6-trienoic acid $^1$H-NMR(400 MHz, CDCl$_3$) δ: 1.19(d, J=7.2 Hz, 3H), 1.21(d, J=7.2 Hz, 3H), 1.29(d, J=6.8 Hz, 3H), 1.62–1.72(m, 1H), 1.87–1.99(m, 1H), 2.22(bs, 3H), 2.39(bs, 3H), 2.82–2.93(m, 1H), 3.13–3.25(m, 2H), 4.14(hept., J=7.2 Hz, 1H), 5.79(s, 1H), 6.35(d, J=14.8 Hz, 1H), 6.55(d, J=11.2 Hz, 1H), 6.67(d, J=8.4 Hz, 1H), 7.11(dd, J=11.2, 14.8 Hz, 1H), 7.21–7.28(m, 2H).

Example 13

Ethyl (E)-3-[1-(1-methylethyl)-3-methyl-1,2,3,4-tetra-hydroquinolin-6-yl]-2-fluoro-2-butenoate $^1$H-NMR(400 MHz, CDCl$_3$) δ: 1.03(d, J=6.4 Hz, 3H), 1.14(t, J=7.2 Hz, 3H), 1.16(d, J=6.4 Hz, 3H), 1.18(d, J=6.4 Hz, 3H), 1.90–2.02(m, 1H), 2.12(d, J=4.8 Hz, 3H), 2.39(dd, J=10.0, 15.2 Hz, 1H), 2.66–2.75(m, 2H), 3.20(ddd, J=2.0, 4.0, 10.0 Hz, 1H), 4.09–4.15(m, 3H), 6.61(d, J=8.8 Hz, 1H), 6.80(d, J=2.4 Hz, 1H), 6.92(dd, J=2.4, 8.8 Hz, 1H).

Example 14

Methyl (E,E,E)-7-[1-(1-methylethyl)-3-methyl-1,2,3,4-tetrahydroquinolin-6-yl]-6-fluoro-3-methyl-octa-2,4,6-trienoate $^1$H-NMR(400 MHz, CDCl$_3$) δ: 1.05(d, J=6.8 Hz, 3H), 1.19(d, J=6.4 Hz, 3H), 1.21(d, J=6.8 Hz, 3H), 1.96–2.02(m, 1H), 2.11(d, J=4.0 Hz, 3H), 2.20(s, 3H), 2.41(dd, J=10.4, 15.6 Hz, 1H), 2.69–2.78(m, 2H), 3.23(ddd, J=2.0, 4.0, 10.0 Hz, 1H), 3.70(s, 3H), 4.12(hept., J=6.8 Hz, 1H), 5.84(s, 1H), 6.49(d, J=15.6 Hz, 1H), 6.65(d, J=9.2 Hz, 1H), 6.67(dd, J=15.2, 26.8 Hz, 1H), 6.85(d, J=2.0 Hz, 1H), 6.95(dd, J=2.0, 8.8 Hz, 1H).

Example 15

(E,E,E)-7-[1-(1-Methylethyl)-3-methyl-1,2,3,4-tetra-hydroquinolin-6-yl]-6-fluoro-3-methyl-octa-2,4,6-trienoic acid $^1$H-NMR(400 MHz, CDCl$_3$) δ: 1.05(d, J=6.4 Hz, 3H), 1.19(d, J=6.8 Hz, 3H), 1.21(d, J=6.4 Hz, 3H), 1.94–2.04(m, 1H), 2.12(d, J=3.6 Hz, 3H), 2.21(s, 3H), 2.41(dd, J=10.8, 15.6 Hz, 1H), 2.69–2.76(m, 2H), 3.23(ddd, J=2.0, 4.0, 10.0 Hz, 1H), 5.86(s, 1H), 6.52(d, J=15.6 Hz, 1H), 6.65(d, J=8.4 Hz, 1H), 6.71(dd, J=15.2, 26.4 Hz, 1H), 6.86(d, J=2.0 Hz, 1H), 6.95(dd, J=2.0, 8.4 Hz, 1H).

Example 16

Ethyl (E)-3-[1-(1-methylethyl)-3-methyl-1,2,3,4-tetra-hydroquinolin-6-yl]-2-butenoate $^1$H-NMR(400 MHz, CDCl$_3$) δ: 1.04(d, J=6.4 Hz, 3H), 1.18(d, J=6.4 Hz, 3H), 1.20(d, J=6.4 Hz, 3H), 1.31(t, J=7.2 Hz, 3H), 1.90–2.02(m, 1H), 2.41(dd, J=10.0, 15.6 Hz, 1H), 2.70–2.80(m, 2H), 3.22(ddd, J=2.0, 4.0, 10.0 Hz, 1H), 4.14(hept., J=6.4 Hz, 1H), 4.18(q, J=7.2 Hz, 2H), 6.09(d, J=1.2 Hz, 1H), 6.63(d, J=8.8 Hz, 1H), 7.18(d, J=2.4 Hz, 1H), 7.28(dd, J=2.4, 8.8 Hz, 1H).

Example 17

Methyl (E,E,E)-7-[1-(1-methylethyl)-3-methyl-1,2,3,4-tetrahydroquinolin-6-yl]-3-methyl-octa-2,4,6-trienoate $^1$H-NMR(400 MHz, CDCl$_3$) δ: 1.05(d, J=6.4 Hz, 3H), 1.17(d, J=6.4 Hz, 3H), 1.20(d, J=6.8 Hz, 3H), 1.92–2.02(m, 1H), 2.20(d, J=0.8 Hz, 3H), 2.38(d, J=1.2 Hz, 3H), 2.42(dd, J=10.4, 15.6 Hz, 1H), 2.69–2.80(m, 2H), 3.22(ddd, J=2.0, 4.0, 10.0 Hz, 1H), 3.71(s, 3H), 4.13(hept., J=6.4 Hz, 1H), 5.77(s, 1H), 6.32(d, J=14.8 Hz, 1H), 6.53(d, J=11.2 Hz, 1H), 6.64(d, J=9.2 Hz, 1H), 7.06(dd, J=11.2, 14.8 Hz, 1H), 7.14(d, J=2.0 Hz, 1H), 7.25(dd, J=2.0, 8.8 Hz, 1H).

Example 18

(E,E,E)-7-[1-(1-Methylethyl)-3-methyl-1,2,3,4-tatra-hydroquinolin-6-yl]-3-methyl-octa-2,4,6-trienoic acid $^1$H-NMR(400 MHz, CDCl$_3$) δ: 1.05(d, J=6.4 Hz, 3H), 1.18(d, J=6.8 Hz, 3H), 1.20(d, J=6.8 Hz, 3H), 1.90–2.03(m, 1H), 2.21(bs, 3H), 2.39(bs, 3H), 2.42(dd, J=10.4, 15.6 Hz, 1H), 2.68–2.82(m, 2H), 3.18–3.26(m, 1H), 4.14(hept., J=6.4 Hz, 1H), 5.79(bs, 1H), 6.34(d, J=15.2 Hz, 1H), 6.55(d, J=12.0 Hz, 1H), 6.65(d, J=9.2 Hz, 1H), 7.10(dd, J=11.2, 14.8 Hz, 1H), 7.15(d, J=1.2 Hz, 1H), 7.24–7.28(m, 1H).

Example 19

Ethyl (E)-3-[1-(1-methylethyl)-2-methyl-1,2,3,4-tetra-hydroquinolin-6-yl]-2-fluoro-2-butenoate $^1$H-NMR(400 MHz, CDCl$_3$) δ: 1.08(d, J=6.4 Hz, 3H), 1.12(t, J=7.2 Hz, 3H), 1.19(d, J=6.8 Hz, 3H), 1.27(d, J=6.8 Hz, 3H), 1.65–1.75(m, 2H), 2.13(d, J=4.4 Hz, 3H), 2.63(dd, J=4.4, 16.8 Hz, 1H), 2.86(ddd, J=6.0, 13.6, 16.4 Hz, 1H), 3.68–3.77(m, 1H), 4.06–4.15(m, 3H), 6.66(d, J=8.4 Hz, 1H), 6.86(d, J=2.4 Hz, 1H), 6.92(dd, J=2.4, 8.4 Hz, 1H).

Example 20

Methyl (E,E,E)-7-[1-(1-methylethyl)-2-methyl-1,2,3,4-tetrahydroquinolin-6-yl]-6-fluoro-3-methyl-octa-2,4,6-trienoate $^1$H-NMR(400 MHz, CDCl$_3$) δ: 1.12(d, J=6.4 Hz, 3H), 1.22(d, J=6.4 Hz, 3H), 1.29(d, J=6.8 Hz, 3H), 1.64–1.80(m, 2H), 2.13(d, J=3.6 Hz, 3H), 2.22(s, 3H), 2.61–2.69(m, 1H), 2.84–2.94(m, 1H), 3.70(s, 3H), 3.70–3.78(m, 1H), 4.11(hept., J=6.4 Hz, 1H), 5.84(s, 1H), 6.50(d, J=15.6 Hz, 1H), 6.69(d, J=8.8 Hz, 1H), 6.70(dd, J=15.6, 26.4 Hz, 1H), 6.92(d, J=2.4 Hz, 1H), 6.96(dd, J=2.4, 8.8 Hz, 1H).

Example 21

(E,E,E)-7-[1-(1-Methylethyl)-2-methyl-1,2,3,4-tetra-hydroquinolin-6-yl]-6-fluoro-3-methyl-octa-2,4,6-trienoic acid ¹H-NMR(400 MHz, CDCl₃) δ: 1.12(d, J=6.4 Hz, 3H), 1.22(d, J=6.4 Hz, 3H), 1.29(d, J=6.8 Hz, 3H), 1.60–1.80(m, 2H), 2.13(d, J=4.0 Hz, 3H), 2.22(s, 3H), 2.65(dd, J=4.4, 16.8 Hz, 1H), 2.89(ddd, J=6.0, 13.6, 16.4 Hz, 1H), 3.70–3.80(m, 1H), 4.11(hept., J=6.4 Hz, 1H), 5.86(s, 1H), 6.53(d, J=16.8 Hz, 1H), 6.70(d, J=8.4 Hz, 1H), 6.74(dd, J=16.0, 26.4 Hz, 1H), 6.92(d, J=2.0 Hz, 1H), 6.96(dd, J=2.0, 8.4 Hz, 1H).

Example 22

Ethyl (E)-3-(1-methyl-1,2,3,4-tetrahydroquinolin-6-yl)-2-butenoate

¹H-NMR(400 MHz, CDCl₃) δ: 1.31(t, J=6.5 Hz, 3H), 1.98(tt, J=6.0, 6.0 Hz, 2H), 2.55(d, J=1.0 Hz, 3H), 2.77(t, J=6.0 Hz, 2H), 2.93(s, 3H), 3.28(t, J=6.0 Hz, 2H), 4.19(q, J=6.5 Hz, 2H), 6.10(q, J=1.0 Hz, 1H), 6.53(d, J=9.0 Hz, 1H), 7.18(d, J=2.0 Hz, 1H), 7.30(dd, J=9.02, 2.0 Hz, 1H).

Example 23

Methyl (E,E,E)-7-(1-methyl-1,2,3,4-tetrahydroquinolin-6-yl)-3-methyl-octa-2,4,6-trienoate ¹H-NMR(400 MHz, CDCl₃) δ: 1.93–2.02(m, 2H), 2.21(s, 3H), 2.38(bs, 3H), 2.78(t, J=6.0 Hz, 2H), 2.92(s, 3H), 3.26(t, J=6.0 Hz, 2H), 3.71(s, 3H), 5.77(s, 1H), 6.33(d, J=14.8 Hz, 1H), 6.51–6.56(m, 2H), 7.05(dd, J=11.6, 15.2 Hz, 1H), 7.16(d, J=2.4 Hz, 1H), 7.24–7.27(m, 1H).

Example 24

(E,E,E)-7-(1-Methyl-1,2,3,4-tetrahydroquinolin-6-yl)-3-methyl-octa-2,4,6-trienoic acid ¹H-NMR(400 MHz, CDCl₃) δ: 1.99(tt, J=6.0, 6.0 Hz, 2H), 2.21(s, 3H), 2.39(s, 3H), 2.78(t, J=6.0 Hz, 2H), 2.92(s, 3H), 3.26(t, J=6.0 Hz, 2H), 5.80(s, 1H), 6.35(d, J=15.0 Hz, 1H), 6.55(d, J=12.5 Hz, 1H), 6.55(d, J=8.5 Hz, 1H), 7.10(dd, J=15.0, 12.5 Hz, 1H), 7.15(d, J=2.0 Hz, 1H), 7.26(dd, J=2.0, 8.5 Hz, 1H).

Example 25

Ethyl (E)-3-(1-cyclohexyl-1,2,3,4-tetrahydroquinolin-6-yl) -2-butenoate

¹H-NMR(400 MHz, CDCl₃) δ: 1.10–1.53(m, 8H), 1.66–1.92(m, 7H), 2.55(d, J=0.8 Hz, 3H), 2.73(t, J=6.0 Hz, 2H), 3.24(t, J=6.0 Hz, 2H), 3.55–3.65(m, 1H), 4.10–4.20(m, 2H), 6.08(q, J=1.2 Hz, 1H), 6.60(d, J=9.2 Hz, 1H), 7.17(d, J=2.4 Hz, 1H), 7.27(dd, J=2.4, 8.4 Hz, 1H).

Example 26

Methyl (E,E,E)-7-(1-cyclohexyl-1,2,3,4-tetrahydroquinolin-6-yl) -3-methyl-octa-2,4,6-trienoate ¹H-NMR(400 MHz, CDCl₃) δ: 1.10–1.56(m, 5H), 1.66–1.92(m, 7H), 2.20(d, J=0.8 Hz, 3H), 2.38(d, J=0.8 Hz, 3H), 2.74(t, J=6.0 Hz, 2H), 3.23(t, J=5.6 Hz, 2H), 3.55–3.65 (m, 1H), 3.71(s, 3H), 5.77(s, 1H), 6.32(d, J=15.2 Hz, 1H), 6.53(bd, J=11.2 Hz, 1H), 6.61(d, J=9.2H, 1H), 7.06(dd, J=10.8, 14.8 Hz, 1H), 7.14(d, J=2.4 Hz, 1H), 7.23(dd, J=2.4, 8.4 Hz, 1H).

Example 27

(E,E,E)-7-(1-Cyclohexyl-1,2,3,4-tetrahydroquinolin-6-yl)-3-methyl-octa-2,4,6-trienoic acid ¹H-NMR(400 MHz, CDCl₃) δ: 1.10–1.54(m, 5H), 1.66–1.94(m, 7H), 2.21(s, 3H), 2.39(s, 3H), 2.74(t, J=6.0 Hz, 2H), 3.23(t, J=6.0 Hz, 2H), 3.55–3.65(m, 1H), 5.79(s, 1H), 6.34(d, J=14.8 Hz, 1H), 6.54(d, J=11.6 Hz, 1H), 6.61(d, J=9.2 Hz, 1H), 7.10(dd, J=11.2, 14.4 Hz, 1H), 7.14(d, J=2.0 Hz, 1H), 7.23–7.26(m, 1H).

Example 28

Ethyl (E)-3-[1-(1-methylethyl) -8-chloro-1,2,3,4-tetra-hydroquinolin-6-yl]-2-fluoro-2-butenoate ¹H-NMR(400 MHz, CDCl₃) δ: 1.06(t, J=6.8 Hz, 3H), 1.16(d, J=6.8 Hz, 6H), 1.84(tt, J=6.0, 6.0 Hz, 2H), 2.10(d, J=4.4 Hz, 3H), 2.68(t, J=6.0 Hz, 2H), 3.14(t, J=6.0 Hz, 2H), 4.08(q, J=6.8 Hz, 2H), 4.12(hept., J=6.8 Hz, 1H), 6.70–6.72 (m, 1H), 6.99(d, J=2.0 Hz, 1H).

Example 29

Methyl (E,E,E)-7-[1-(1-methylethyl)-8-chloro-1,2,3,4-tetrahydroquinolin-6-yl]-6-fluoro-3-methyl-octa-2,4,6-trienoate ¹H-NMR(400 MHz, CDCl₃) δ: 1.19(d, J=6.8 Hz, 6H), 1.86(tt, J=6.0, 6.0 Hz, 2H), 2.09(d, J=4.0 Hz, 3H), 2.19(s, 3H), 2.70(t, J=6.0 Hz, 1H), 3.16(t, J=6.0 Hz, 2H), 3.71(s, 3H), 4.16(hept., J=6.8 Hz, 1H), 5.86(s, 1H), 6.52(s, 1H), 6.56(dd, J=14.8, 27.6 Hz, 1H), 6.77–6.79(m, 1H), 7.06(d, J=2.4 Hz, 1H)

Example 30

(E,E,E)-7-[1-(1-Methylethyl)-8-chloro-1,2,3,4-tetra-hydroquinolin-6-yl]-6-fluoro-3-methyl-octa-2,4,6-trienoic acid ¹H-NMR(400 MHz, CDCl₃) δ: 1.19(d, J=6.8 Hz, 6H), 1.83–1.90(m, 2H), 2.10(d, J=3.6 Hz, 3H), 2.19(s, 3H), 2.70(t, J=6.8 Hz, 2H), 3.16(t, J=6.0 Hz, 2H), 4.16(hept., J=6.8 Hz, 1H), 5.88(s, 1H), 6.55(s, 1H), 6.59(dd, J=15.6, 32.4 Hz, 1H), 6.77–6.79(m, 1H), 7.06(d, J=2.4 Hz, 1H).

Example 31

Ethyl (E)-3-[1-(1-methylethyl)-1,2,3,4-tetrahydro-quinolin-6-yl]-2-pentenoate

¹H-NMR(400 MHz, CDCl₃) δ: 1.13(t, J=7.6 Hz, 3H), 1.20(d, J=6.4 Hz, 6H), 1.30(t, J=6.8 Hz, 3H), 1.90(tt, J=6.0, 6.0 Hz, 2H), 2.74(t, J=6.0 Hz, 2H), 3.08(q, J=7.6 Hz, 2H), 3.20(t, J=6.0 Hz, 2H), 4.15(hept., J=6.4 Hz, 1H), 4.18(q, J=7.2 Hz, 2H), 6.00(s, 1H), 6.64(d, J=9.2 Hz, 1H), 7.17(d, J=2.4 Hz, 1H), 7.27(dd, J=2.8, 9.2 Hz, 1H).

Example 32

Methyl (E,E,E)-7-[1-(1-(methylethyl)-1,2,3,4 -tetra-hydroquinolin-6-yl]-3-methyl-nona-2,4,6-trienoate ¹H-NMR(400 MHz, CDCl₃) δ: 1.11(t, J=7.6 Hz, 3H), 1.19(d, J=6.4 Hz, 6H), 1.91(tt, J=6.0, 6.0 Hz, 2H), 2.38(d, J=0.8 Hz, 3H), 2.68(q, J=7.6 Hz, 2H), 2.75(t, J=6.0 Hz, 2H), 3.19(t, J=6.0 Hz, 2H), 3.71(s, 3H), 4.14(hept., J=6.4 Hz, 1H), 5.76(s, 1H), 6.32(d, J=15.2 Hz, 1H), 6.42(d, J=11.2 Hz, 1H), 6.65(d, J=8.8 Hz, 1H), 7.03(dd, J=11.2, 15.2 Hz, 1H), 7.12(d, J=2.4 Hz, 1H), 7.21(dd, J=2.4, 8.6 Hz, 1H).

Example 33

(E,E,E)-7-[1-(1-Methylethyl)-1,2,3,4-tetrahydroquinolin-6-yl]-3-methyl-nona-2,4,6-trienoic acid $^1$H-NMR(400 MHz, CDCl$_3$) δ: 1.10(t, J=7.6 Hz, 3H), 1.18(d, J=6.4 Hz, 6H), 1.90(tt, J=6.0, 6.0 Hz, 2H), 2.38(bs, 3H), 2.68(q, J=7.6 Hz, 2H), 2.73(t, J=6.0 Hz, 2H), 3.18(t, J=6.0 Hz, 2H), 4.12(hept., J=6.4 Hz, 1H), 5.80(bs, 1H), 6.34(bd, J=16.0 Hz, 1H), 6.43(d, J=12.6 Hz, 1H), 6.64(d, J=8.8 Hz, 1H), 6.92–7.08(m, 1H), 7.12(bs, 1H), 7.21(dd, J=2.4, 8.8 Hz, 1H).

Example 34

Ethyl (E)-3-[1-(1-methylethyl)-8-chloro-1,2,3,4-tetra-hydroquinolin-6-yl]-2-fluoro-2-pentenoate $^1$H-NMR(400 MHz, CDCl$_3$) δ: 1.00 (t, J=7.6 Hz, 3H), 1.11(t, J=7.2 Hz, 3H), 1.17(d, J=6.8 Hz, 6H), 1.89(tt, J=6.0, 6.0 Hz, 2H), 2.51(dq, J=3.5, 7.6 Hz, 2H), 2.71(t, J=6.0 Hz, 2H), 3.15(t, J=6.0 Hz, 2H), 4.09(q, J=7.2 Hz, 2H), 4.10 (hept., J=6.8 Hz, 1H), 6.61(d, J=8.4 Hz, 1H), 6.75(d, J=2.0 Hz, 1H), 6.85(dd, J=2.0, 8.4 Hz, 1H).

Example 35

Methyl (E,E,E)-7-[1-(1-methylethyl)-8-chloro-1,2,3,4-tetrahydroquinolin-6-yl]-6-fluoro-3-methyl-nona-2,4,6-trienoate $^1$H-NMR(400 MHz, CDCl$_3$) δ: 0.99(t, J=7.6 Hz, 3H), 1.19(d, J=6.8 Hz, 6H), 1.83–1.90(m, 2H), 2.17(s, 3H), 2.52(dq, J=3.2, 7.6 Hz, 2H), 2.70(t, J=6.8 Hz, 2H), 3.16(t, J=6.0 Hz, 2H), 3.70(s, 3H), 4.15(hept., J=6.8 Hz, 1H), 5.85(s, 1H), 6.47(dd, J=15.8, 44.0 Hz, 1H), 6.50(d, J=2.4 Hz, 1H), 6.74(d, J=2.0 Hz, 1H), 7.03(d, J=2.0 Hz, 1H).

Example 36

(E,E,E)-7-[1-(1-Methylethyl)-8-chloro-1,2,3,4-tetra-hydroquinolin-6-yl]-6-fluoro-3-methyl-nona-2,4,6-trienoic acid $^1$H-NMR(400 MHz, CDCl$_3$) δ: 0.99(t, J=7.6 Hz, 3H), 1.19(d, J=6.8 Hz, 6H), 1.80– 1.92(m, 2H), 2.17(s, 3H), 2.48–2.56(m, 2H), 2.70(t, J=6.0 Hz, 2H), 3.16(t, J=6.0 Hz, 2H), 4.16(hept., J=6.8 Hz, 1H), 5.87(s, 1H), 6.51(dd, J=16.0, 38.0 Hz, 1H), 6.53(s, 1H), 6.75(d, J=2.0 Hz, 1H), 7.03(d, J=2.0Hz, 1H).

Example 37

Ethyl (E)-3-[1-(1-methylethyl)-8-methoxy-1,2,3,4-tetra-hydroquinolin-6-yl]-2-fluoro-2-butenoate $^1$H-NMR(400 MHz, CDCl$_3$) δ: 1.05(t, J=7.2 Hz, 3H), 1.12(d, J=6.8 Hz, 6H), 1.82(tt, J=6.0, 6.0 Hz, 2H), 2.12(d, J=4.4 Hz, 3H), 2.67(t, J=6.0 Hz, 2H), 3.14(t, J=6.0 Hz, 2H), 3.79(s, 3H), 4.06(q, J=7.2 Hz, 2H), 4.13(hept., J=6.4 Hz, 1H), 6.47(d, J=1.6 Hz, 1H), 6.49(d, J=2.0 Hz, 1H).

Example 38

Methyl (E,E,E)-7-[1-(1-methylethyl)-8-methoxy-1,2,3,4-tetrahydroquinolin-6-yl]-6-fluoro-3-methyl-octa-2,4,6-trienoate $^1$H-NMR(400 MHz, CDCl$_3$) δ: 1.15(d, J=6.8 Hz, 6H), 1.84(tt, J=6.0, 6.0 Hz, 2H), 2.13(d, J=3.6 Hz, 3H), 2.17(s, 3H), 2.69(t, J=6.0 Hz, 2H), 3.16(t, J=6.0 Hz, 2H), 3.70(s, 3H), 3.80(s, 3H), 4.18(hept., J=6.8 Hz, 1H), 5.84(s, 1H), 6.50(d, J=15.6 Hz, 1H), 6.54(bs, 2H), 6.64(dd, J=15.6, 26.4 Hz, 1H)

Example 39

(E,E,E)-7-[1-(1-Methylethyl)-8-methoxy-1,2,3,4-tetra-hydroquinolin-6-yl]-6-fluoro-3-methyl-octa-2,4,6-trienoic acid $^1$H-NMR(400 MHz, CDCl$_3$) δ: 1.15(d, J=6.8 Hz, 6H), 1.80–1.88(m, 2H), 2.14(d, J=3.2 Hz, 3H), 2.17(s, 3H), 2.70(t, J=6.0 Hz, 2H), 3.16(t, J=6.0 Hz, 2H), 3.81(s, 3H), 4.18(hept., J=6.8 Hz, 1H), 6.53(d, J=15.6 Hz, 1H), 6.54(bs, 2H), 6.68(dd, J=15.6, 26.4 Hz, 1H).

Example 40

Ethyl (E)-3-[1-(1-methylethyl)-2,3,4,5-tetrahydro-1H-benzazepin-7-yl]-2-fluoro-2-butenoate $^1$H-NMR(400 MHz, CDCl$_3$) δ: 1.09(t, J=7.2 Hz, 3H), 1.22(d, J=6.8 Hz, 6H), 1.60–1.70(m, 4H), 2.12(d, J=4.8 Hz, 3H), 2.70–2.78(m, 2H), 2.92–2.99(m, 2H), 4.09(hept., J=6.8 Hz, 1H), 4.10(q, J=7.2 Hz, 2H), 6.80–6.98(m, 3H).

Example 41

Ethyl (E,E,E)-7-[1-(1-methylethyl)-2,3,4,5-tetrahydro-1H-benzazepin-7-yl]-6-fluoro-3-methyl-octa-2,4,6-trienoate $^1$H-NMR(400 MHz, CDCl$_3$) δ: 1.24(d, J=6.4 Hz, 6H), 1.60–1.73(m, 4H), 2.13(d, J=3.6 Hz, 3H), 2.19(bs, 3H), 2.73–2.76(m, 2H), 2.94–3.04(m, 2H), 3.70(s, 3H), 3.78 (hept., J=6.4 Hz, 1H), 5.85(s, 1H), 6.51(d, J=15.6 Hz, 1H), 6.64(dd, J=15.6, 26.0 Hz, 1H), 6.89(d, J=8.0 Hz, 1H), 6.98–7.01(m, 2H).

Example 42

(E,E,E)-7-[1-(1-Methylethyl)-2,3,4,5-tetrahydro-1H-benzazepin-7-yl]-6-fluoro-3-methyl-octa-2,4,6-trienoic acid $^1$H-NMR(400 MHz, CDCl$_3$) δ: 1.24(d, J=6.4 Hz, 6H), 1.60–1.76(m, 4H), 2.14(d, J=3.2 Hz, 3H), 2.20(bs, 3H), 2.70–2.80(m, 2H), 2.93–3.03(m, 2H), 3.78(hept., J=6.4 Hz, 1H), 5.87(s, 1H), 6.53(d, J=16.0 Hz, 1H), 6.67(dd, J=15.6, 26.4 Hz, 1H), 6.90(d, J=8.0 Hz, 1H), 6.98–7.01(m, 2H).

Example 43

Ethyl (Z)-3-[1-(1-methylethyl)-2,3,4,5-tetrahydro-1H-benzazepin-7-yl]-2-fluoro-2-butenoate $^1$H-NMR(400 MHz, CDCl$_3$) δ: 1.23(d, J=6.4 Hz, 6H), 1.37(t, J=7.2 Hz, 3H), 1.60–1.70(m, 4H), 2.43(d, J=3.6 Hz, 3H), 2.72–2.80(m, 2H), 2.96–3.03(m, 2H), 3.79(hept., J=6.4 Hz, 1H), 4.32(q, J=7.2 Hz, 2H), 6.88(d, J=8.8 Hz, 1H), 7.19–7.23(m, 2H).

Example 44

Methyl (E,E,Z)-7-[1-(1-methylethyl)-2,3,4,5-tetrahydro-1H-benzazepin-7-yl]-6-fluoro-3-methyl-octa-2,4,6-trienoate $^1$H-NMR(400 MHz, CDCl$_3$) δ: 1.23(d, J=6.8 Hz, 6H), 1.62–1.73(m, 4H), 2.14(d, J=2.4 Hz, 3H), 2.37(s, 3H), 2.72–2.80(m, 2H), 2.93–3.05(m, 2H), 3.73(s, 3H), 3.78 (hept., J=6.8 Hz, 1H), 5.88(s, 1H), 6.59(d, J=15.2 Hz, 1H), 6.82(dd, J=15.2, 26.0 Hz, 1H), 6.89(d, J=8.4 Hz, 1H), 7.23–7.27(m, 2H).

Example 45

(E,E,Z) -7-[1-(1-Methylethyl)-2,3,4,5-tetrahydro-1H-benzazepin-7-yl]-6-fluoro-3-methyl-octa-2,4,6-trienoic acid $^1$H-NMR(400 MHz, CDCl$_3$) δ: 1.23(d, J=6.4 Hz, 6H), 1.62–1.75(m, 4H), 2.15(d, J=2.4 Hz, 3H), 2.38(s, 3H), 2.72–2.80(m, 2H), 2.95–3.05(m, 2H), 3.79(hept., J=6.4 Hz, 1H), 5.92(s, 1H), 6.62(d, J=15.2 Hz, 1H), 6.86(dd, J=15.2, 26.0 Hz, 1H), 6.89(d, J=8.4 Hz, 1H), 7.24–7.29(m, 2H).

Example 46

Ethyl (E)-3-[1-(1-methylethyl)-1,2,3,4,5,6-hexahydrobenzazocin-8-yl]-2-fluoro-2-butenoate $^1$H-NMR(400 MHz, CDCl$_3$) δ: 1.03(t, J=7.2 Hz, 3H), 1.07(d, J=6.0 Hz, 6H), 1.11–1.17(m, 2H), 1.55–1.68(m, 4H), 2.14(d, J=4.4 Hz, 3H), 2.75–2.83(m, 4H), 3.28(hept., J=6.0 Hz), 4.04(q, J=6.8 Hz, 2H), 6.97(d, J=2.0 Hz,. 1H), 6.99(dd, J=2.4, 8.0 Hz, 1H), 7.14(d, J=8.0 Hz, 1H).

Example 47

Methyl (E,E,E)-7-[1-(1-methylethyl)-1,2,3,4,5,6-hexahydrobenzazocin-8-yl]-6-fluoro-3-methyl-octa-2,4,6-trienoate $^1$H-NMR(400 MHz, CDCl$_3$) δ: 1.08(d, J=6.4 Hz, 6H), 1.10–1.19(m, 2H), 1.57–1.67(m, 4H), 2.14(s, 3H), 2.15(d, J=4.0 Hz, 3H), 2.77–2.82(m, 4H), 3.29(hept., J=6.4 Hz, 1H), 3.70(s, 3H), 5.85(s, 1H), 6.51(s, 1H), 6.54(d, J=11.6 Hz, 1H), 7.04(d, J=2.0 Hz, 1H), 7.06(dd, J=2.0, 8.0 Hz, 1H), 7.18(d, J=8.4 Hz, 1H).

Example 48

(E,E,E)-7-[1-(1-Methylethyl)-1,2,3,4,5,6-hexahydrobenzazocin-8-yl]-6-fluoro-3-methyl-octa-2,4,6-trienoic Acid $^1$H-NMR(400 MHz, CDCl$_3$) δ: 1.09(d, J=6.4 Hz, 6H), 1.09–1.19(m, 2H), 1.56–1.68(m, 4H), 2.15(s, 3H), 2.16(d, J=3.6 Hz,3H), 2.76–2.87(m, 4H), 3.30(hept., J=6.4 Hz, 1H), 5.87(s, 1H), 6.54(s, 1H), 6.57(d, J=15.6 Hz, 1H), 7.04(d, J=2.0 Hz, 1H), 7.07(dd, J=2.0, 8.0 Hz, 1H), 7.18(d, J=8.0 Hz, 1H).

Example 49

Ethyl (E)-3-[1-(1-methylethyl)-1,2,3,4-tetrahydro-quinolin-7-yl]-2-butenoate $^1$H-NMR(400 MHz, CDCl$_3$) δ: 1.20(d, J=6.4 Hz, 6H), 1.32(t, J=7.2 Hz, 3H), 1.90(tt, J=6.0, 6.0 Hz, 2H), 2.55(d, J=1.6 Hz, 3H), 2.74(t, J=6.0 Hz, 2H), 3.17(t, J=6.0 Hz, 2H), 4.15(hept., J=6.4 Hz, 1H), 4.21(q, J=7.2 Hz, 2H), 6.09(q, J=1.2 Hz, 1H), 6.66(dd, J=1.6, 7.6 Hz, 1H),. 6.74(d, J=1.2 Hz, 1H), 6.94(d, J=7.6 Hz, 1H).

Example 50

Methyl (E,E,E)-7-[1-(1-methylethyl)-1,2,3,4-tetra-hydroquinolin-7-yl]-3-methyl-octa-2,4,6-trienoate $^1$H-NMR(400 MHz, CDCl$_3$) δ: 1.20(d, J=6.4 Hz, 6H), 1.91(tt, J=6.0, 6.0 Hz, 2H), 2.23(d, J=1.6 Hz, 3H) 2.39(d, J=1.2 Hz, 3H), 2.73(t, J=6.0 Hz, 2H), 3.17(t, J=6.0 Hz, 2H), 3.72(s, 3H), 4.17(hept., J=6.8 Hz, 1H), 5.80(s, 1H), 6.36(d, J=15.2 Hz, 1H), 6.52(bd, J=11.2 Hz, 1H), 6.67(dd, J=2.0, 7.6 Hz, 1H), 6.76(d, J=1.2 Hz, 1H), 7.04(dd, J=11.2, 14.8 Hz, 1H).

Example 51

(E,E,E) -7-[1-(1-Methylethyl)-1,2,3,4-tetrahydro-quinolin-7-yl]-3-methyl-octa-2,4,6-trienoic acid $^1$H-NMR(400 MHz, CDCl$_3$) δ: 1.21(d, J=6.4 Hz, 6H), 1.90(tt, J=6.0, 6.0 Hz, 2H), 2.24(s, 3H), 2.39(s, 3H), 2.73(t, J=6.0 Hz, 2H), 3.17(t, J=6.0 Hz, 2H), 4.17(hept., J=6.4 Hz, 1H), 5.82(s, 1H), 6.39(d, J=15.2 Hz, 1H), 6.53(d, J=12.0 Hz, 1H), 6.67(dd, J=1.6, 7.6 Hz, 1H), 6.76(s, 1H), 6.93(d, J=7.8 Hz, 1H), 7.08(dd, J=11.6, 15.6 Hz, 1H)

Example 52

Ethyl (E)-3-[1-(1-methylethyl)-1,2,3,4-tetrahydro-quinolin-7-yl]-2-fluoro-2-butenoate $^1$H-NMR(400 MHz, CDCl$_3$) δ: 1.08(t, J=7.2 Hz, 3H), 1.16(d, J=6.8 Hz, 6H), 1.89(tt, J=6.0, 6.0 Hz, 2H), 2.12(d, J=4.4 Hz, 3H), 2.72(t, J=6.0 Hz, 2H), 3.14(t, J=6.0 Hz, 2H), 4.04(hept., J=6.8 Hz, 1H), 4.08(q, J=7.2 Hz, 2H), 6.35(dd, J=2.0, 7.2 Hz, 1H), 6.45(bs, 1H), 6.90(d, J=7.6 Hz, 1H).

Example 53

Methyl (E,E,E)-7-[1-(1-methylethyl)-1,2,3,4-tetra-hydroquinolin-7-yl]-6-fluoro-3-methyl-octa-2,4,6-trienoate $^1$H-NMR(400 MHz, CDCl$_3$) δ: 1.18(d, J=6.8 Hz, 6H), 1.91(tt, J=6.0, 6.0 Hz, 2H), 2.13(d, J=3.6 Hz, 3H), 2.18(d, J=0.8 Hz, 3H), 2.74(t, J=6.0 Hz, 2H), 3.18(t, J=6.0 Hz, 2H), 3.70(s, 3H), 4.06(hept., J=6.8 Hz, 1H), 5.85(s, 1H), 6.43(dd, J=1.6, 7.6 Hz, 1H), 6.52(d, J=15.6 Hz, 1H), 6.52(bs, 1H), 6.67(dd, J=16.0, 26.4 Hz, 1H), 6.93(d, J=7.6 Hz, 1H).

Example 54

(E,E,E)-7-[1-(1-Methylethyl)-1,2,3,4-tetrahydro-quinolin-7-yl]-6-fluoro-3-methyl-octa-2,4,6-trienoic acid $^1$H-NMR(400 MHz, CDCl$_3$) δ: 1.18(d, J=6.8 Hz, 6H), 1.86–1.95(m, 2H), 2.14(d, J=3.6 Hz, 3H), 2.18(bs, 3H), 2.75(t, J=6.0 Hz, 2H), 3.18(t, J=6.0 Hz, 2H), 4.06(hept., J=6.8 Hz, 1H), 5.87(bs, 1H), 6.43(bd, J=7.2 Hz, 1H), 6.52–6.56(m, 2H), 6.70(dd, J=15.6, 26.0 Hz, 1H), 6.93(d, J=7.6 Hz, 1H).

Example 55

Ethyl (E)-3-(2,3,6,7-tetrahydro-1H,5H-benzo[I,J]quinolizin-9-yl)-2-butenoate $^1$H-NMR(400 MHz, CDCl$_3$) δ: 1.30(t, J=6.8 Hz, 3H), 1.97(tt, J=6.4, 5.6 Hz, 4H), 2.53(d, J=1.2 Hz, 3H), 2.75(t, J=6.4 Hz, 4H), 3.19(t, J=5.6 Hz, 4H), 4.18(q, J=7.2 Hz, 2H), 6.07 (q, J=1.2 Hz, 1H), 7.02(s, 2H)

Example 56

Methyl (E,E,E)-7-(2,3,6,7-tetrahydro-1H,5H-benzo[I,J]quinolizin-9-yl)-3-methyl-octa-2,4,6-trienoate $^1$H-NMR(400 MHz, CDCl$_3$) δ: 1.97(tt, J=6.4, 5.6 Hz, 4H), 2.18(s, 3H), 2.38(s, 3H), 2.76(t, J=6.4 Hz), 3.17(t, J=6.4

Hz, 4H), 3.71(s, 3H), 5.76(s, 1H), 6.32(d, J=14.8 Hz, 1H), 6.51(d, J=10.8 Hz, 1H), 6.98(s, 2H), 7.05(dd, J=11.2, 15.2 Hz, 1H).

Example 57

(E,E,E)-7-(2,3,6,7-Tetrahydro-1H,5H-benzo[I,J]quino-lizin-9-yl)-3-methyl-octa-2,4,6-trienoic acid $^1$H-NMR(400 MHz, CDCl$_3$) δ: 1.97(tt, J=6.4, 5.6 Hz, 4H), 2.19(s, 3H), 2.38(s, 3H), 2.76(t, J=6.4 Hz, 4H), 3.17(t, J=5.6 Hz, 4H), 5.79(s, 1H), 6.34(d, J=14.8 Hz, 1H), 6.52(d, J=11.2 Hz, 1H), 6.99(s, 2H), 7.09(dd, J=11.6, 15.2 Hz, 1H).

Example 58

Ethyl (E)-3-(2,3,6,7-tetrahydro-1H,5H-benzo[I,J]quino-lizin-9-yl]-2-fluoro-2-butenoate $^1$H-NMR(400 MHz, CDCl$_3$) δ: 1.15(t, J=7.2 Hz, 3H), 1.93–2.05(m, 4H), 2.10(d, J=4.8 Hz, 3H), 2.72(t, J=6.0 Hz, 4H), 3.14(t, J=6.0 Hz, 4H), 4.12(q, J=7.2 Hz, 2H), 6.64(s, 2H).

Example 59

Methyl (E,E,E)-7-(2,3,6,7-tetrahydro-1H,5H-benzo[I,J]quinolizin-9-yl)-6-fluoro-3-methyl-octa-2,4,6-trienoate $^1$H-NMR(400 MHz, CDCl$_3$) δ: 1.98(tt, J=6.0, 6.0 Hz, 4H), 2.09(d, J=3.6 Hz, 3H), 2.20(d, J=0.8 Hz, 3H), 2.75(t, J=6.4 Hz, 4H), 3.17(t, J=6.0 Hz, 4H), 3.70(s, 3H), 5.84(s, 1H), 6.48(d, J=16.0 Hz, 1H), 6.67(dd, J=16.0, 26.4 Hz, 1H), 6.69(s, 2H).

Example 60

(E,E,E)-7-(2,3,6,7-Tetrahydro-1H,5H-benzo[I,J]quino-lizin-9-yl)-6-fluoro-3-methyl-octa-2,4,6-trienoic acid $^1$H-NMR(400 MHz, CDCl$_3$) δ: 1.98(tt, J=6.0, 6.0 Hz, 4H), 2.16(d, J=3.6 Hz, 3H), 2.21(s, 3H), 2.75(t, J=6.4 Hz, 4H), 3.18(t, J=6.0 Hz, 4H), 5.86(s, 1H), 6.51(d, J=16.0 Hz, 1H), 6.71(dd, J=16.0, 26.4 Hz, 1H), 6.69(s, 2H).

Example 61

Ethyl (E)-3-[1,4-di(1-methylethyl)-1,2,3,4-tetrahydro-quinoxalin-6-yl]-2-butenoate $^1$H-NMR(400 MHz, CDCl$_3$) δ: 1.19(d, J=6.5 Hz, 6H), 1.20(d, J=6.5 Hz, 6H), 1.31(t, J=6.5 Hz, 3H), 2.56(bs, 3H), 3.00–3.40(m, 4H), 4.00–4.30(m, 2H), 4.19(q, J=6.5 Hz, 2H), 5.98–6.15(m, 1H), 6.53–6.68(m, 1H), 6.75–7.00(m, 2H).

Example 62

Methyl (E,E,E)-7-[1,4-di(1-methylethyl)-1,2,3,4-tetra-hydroquinoxalin-6-yl]-3-methyl-octa-2,4,6-trienoate $^1$H-NMR(400 MHz, CDCl$_3$) δ: 1.19(d, J=6.5 Hz, 6H), 1.20(d, J=6.5 Hz, 6H), 2.22(s, 3H), 2.38(s, 3H), 3.15–3.21(m, 2H), 3.22–3.28(m, 2H), 3.71(s, 3H), 5.77(s, 1H), 6.32(d, J=15.0 Hz, 1H), 6.51(d, J=11.0 Hz, 1H), 6.60(d, J=8.0 Hz, 1H), 6.80(s, 1H), 6.83(d, J=8.5 Hz, 1H), 7.06(dd, J=11.0, 15.0 Hz, 1H).

Example 63

(E,E,E)-7-[1,4-Di(1-methylethyl)-1,2,3,4-tetrahydro-quinoxalin-6-yl]-3-methyl-octa-2,4,6-trienoic acid $^1$H-NMR(400 MHz, CDCl$_3$) δ: 1.15(d, J=6.5 Hz, 6H), 1.19(d, J=6.5 Hz, 6H), 2.18(bs, 3H), 2.33(bs, 3H), 3.10–3.35 (m, 4H), 3.95–4.23(m, 2H), 5.81(bs, 1H), 6.32(d, J=15.0 Hz, 1H), 6.49(d, J=11.0 Hz, 1H), 6.58(d, J=8.0 Hz, 1H), 6.75–6.85(m, 2H), 6.90–7.13(m, 1H).

Example 64

Ethyl (E)-3-[1,4-di(1-methylethyl)-1,2,3,4-tetra-hydroquinoxalin-6-yl]-2-fluoro-2-butenoate $^1$H-NMR(400 MHz, CDCl$_3$) δ: 1.12(t, J=7.2 Hz, 3H), 1.16(d, J=6.8 Hz, 3H), 1.17(d, J=6.8 Hz, 3H), 2.12(d, J=4.4 Hz, 3H), 3.16–3.24(m, 4H), 4.00–4.13(m, 4H), 6.45(d, J=1.6 Hz, 1H), 6.49(dd, J=1.6, 10.0 Hz, 1H), 6.57(d, J=8.4 Hz, 1H).

Example 65

Methyl (E,E,E)-7-[1,4-di(1-methylethyl)-1,2,3,4-tetra-hydroquinoxalin-6-yl]-6-fluoro-3-methyl-octa-2,4,6-trienoate $^1$H-NMR(400 MHz, CDCl$_3$) δ: 1.18(d, J=6.4 Hz, 3H), 1.20(d, J=6.4 Hz, 3H), 2.13(bs, 3H), 2.19(s, 3H), 3.14–3.28 (m, 4H), 3.70(s, 3H), 3.98–4.12(m, 2H), 5.84(s, 1H), 6.48–6.78(m, 5H).

Example 66

(E,E,E)-7-[1,4-Di(1-methylethyl)-1,2,3,4-tetrahydro-quinoxalin-6-yl]-6-fluoro-3-methyl-octa-2,4,6-trienoic acid $^1$H-NMR(400 MHz, CDCl$_3$) δ: 1.18(d, J=6.4 Hz, 3H), 1.20(d, J=6.4 Hz, 3H), 2.14(d, J=3.6 Hz, 3H), 2.20(bs, 3H), 3.18–3.29(m, 4H), 3.97–4.12(m, 2H), 5.86(s, 1H), 6.50–6.63(m, 4H), 6.76(dd, J=15.6, 26.0 Hz, 1H).

Example 67

Ethyl (E)-3-[4-(1-methylethyl)-3,4-dihydro-2H-1,4-benzoxazin-7-yl]-2-fluoro-2-butenoate $^1$H-NMR(400 MHz, CDCl$_3$) δ: 1.13(t, J=7.2 Hz, 3H), 1.17(d, J=6.4 Hz, 6H), 2.10(d, J=4.8 Hz, 3H), 3.24(t, J=4.8 Hz, 2H), 4.11(q, J=7.2 Hz, 2H), 4.22(t, J=4.4 Hz, 2H), 6.65–6.69(m, 3H).

Example 68

Methyl (E,E,E)-7-[4-(1-methylethyl)-3,4-dihydro-2H-1,4-benzoxazin-7-yl]-6-fluoro-3-methyl-octa-2,4,6-trienoate $^1$H-NMR(400 MHz, CDCl$_3$) δ: 1.20(d, J=6.8 Hz, 6H), 2.10(d, J=3.6 Hz, 3H), 2.20(s, 3H), 3.26(t, J=4.8 Hz, 2H), 3.70(s, 3H), 4.11(hept., J=6.8 Hz, 1H), 4.24(t, J=4.8 Hz, 2H), 5.84(s, 1H), 6.50(d, J=15.2 Hz, 1H), 6.59–6.72(m, 4H).

Example 69

(E,E,E)-7-[1-(4-Methylethyl)-3,4-dihydro-2H-1,4-benzoxazin-7-yl]-6-fluoro-3-methyl-octa-2,4,6-trienoic acid $^1$H-NMR(400 MHz, CDCl$_3$) δ: 1.21(d, J=6.8 Hz, 6H), 2.11(d, J=3.6 Hz, 3H), 2.21(s, 3H), 3.27(t, J=4.8 Hz, 2H), 4.11(hept., J=6.8 Hz, 1H), 4.24(t, J=4.8 Hz, 2H), 5.86(s, 1H), 6.53(d, J=15.6 Hz, 1H), 6.63–6.74(m, 4H).

Example 70

Ethyl (E)-3-[1-(1-methylethyl)indol-5-yl]-2-butenoate $^1$H-NMR(400 MHz, CDCl$_3$) δ: 1.33(t, J=7.0 Hz, 3H), 1.54(d, J=6.5 Hz, 6H), 2.67(d, J=1.0 Hz, 3H), 4.22(q, J=7.0

Hz, 2H), 4.68(hept., J=6.5 Hz, 1H), 6.20(q, J=1.0 Hz, 1H), 6.54(d, J=3.0 Hz, 1H), 7.25(d, J=3.0 Hz, 1H), 7.34–7.40(m, 2H), 7.80(d, J=1.15Hz, 1H).

Example 71

(E,E,E)-7-[1-(1-Methylethyl)-indol-5-yl]-3-methyl-octa-2,4,6-trienoic acid $^1$H-NMR(400 MHz, CDCl$_3$) δ: 1.53(d, J=6.5 Hz, 6H), 2.34(s, 3H), 2.41(s, 3H), 4.66(hept., J=6.5 Hz, 1H), 5.84(s, 1H), 6.40(d, J=15.0 Hz, 1H), 6.52(d, J=2.5 Hz, 1H), 6.64(d, J=11.0 Hz, 1H), 7.12(dd, J=15.0, 11.0 Hz, 1H), 7.22(d, J=3.0 Hz, 1H), 7.33–7.41(m, 2H), 7.75(bs, 1H).

Example 72

Ethyl (E)-3-[1-(1-methylethyl)-indol-5-yl]-2-fluoro-2-butenoate $^1$H-NMR(400 MHz, CDCl$_3$) δ: 1.00(t, J=7.2 Hz, 3H), 1.53(d, J=6.4 Hz, 6H), 2.21(d, J=4.4 Hz, 3H), 4.05(q, J=6.8 Hz, 2H), 4.67(hept., J=6.4 Hz, 1H), 6.49(d, J=3.2 Hz, 1H), 7.03(dd, J=2.0, 8.8 Hz, 1H), 7.22(d, J=3.2 Hz, 1H), 7.34(d, J=8.8 Hz, 1H), 7.44(d, J=2.0 Hz, 1H).

Example 73

Methyl (E,E,E)-7-[1-(1-methylethyl)-indol-5-yl]-6-fluoro-3-methyl-octa-2,4,6-trienoate $^1$H-NMR(400 MHz, CDCl$_3$) δ: 1.56(d, J=6.8 Hz, 6H), 2.13(d, J=0.8 Hz, 3H), 2.21(d, J=3.6 Hz, 3H), 3.69(s, 3H), 4.69(hept., J=6.8 Hz, 1H), 5.84(s, 1H), 6.52(d, J=3.2 Hz, 1H), 6.54(d, J=16.0 Hz, 1H), 6.60(dd, J=16.0, 26.4 Hz, 1H), 7.09(dd, J=1.6, 8.8 Hz, 1H), 7.26(d, J=3.2 Hz, 1H), 7.37(d, J=8.8 Hz, 1H), 7.50(d, J=1.6 Hz, 1H).

Example 74

(E,E,E)-7-[1-(1-Methylethyl)-indol-5-yl]-6-fluoro-3-methyl-octa-2,4,6-trienoic acid $^1$H-NMR(400 MHz, CDCl$_3$) δ: 1.56(d, J=6.8 Hz, 6H), 2.13(bs, 3H), 2.22(d, J=2.8 Hz, 3H), 4.69(hept., J=6.8 Hz, 1H), 5.87(s, 1H), 6.52–6.69(m, 3H), 7.09(bd, J=9.2 Hz, 1H), 7.26(bs, 1H), 7.37(bd, J=11.2 Hz, 1H), 7.50(bs, 1H).

Example 75

Ethyl (E)-3-(3-methyl-4-dimethylamino-phenyl)-2-butenoate $^1$H-NMR(400 MHz, CDCl$_3$) δ: 1.31(t, J=7.1 Hz, 3H), 2.34(s, 3H), 2.56(t, J=1.2 Hz, 3H), 2.73(s, 6H), 4.20(q, J=7.1 Hz, 2H), 6.11(q, J=1.2 Hz, 1H), 6.98(d, J=8.4 Hz, 1H), 7.29–7.32(m, 2H).

Example 76

Methyl (E,E,E)-7-(3-methyl-4-dimethylaminophenyl)-3-methyl-octa-2,4,6-trienoate $^1$H-NMR(400 MHz, CDCl$_3$) δ: 2.23(s, 3H), 2.34(s, 3H), 2.38(s, 3H), 2.72(s, 6H), 3.72(s, 3H), 5.80(s, 1H), 6.36(d, J=15.0 Hz, 1H), 6.55(d, J=11.0 Hz, 1H), 6.98(d, J=8.4 Hz, 1H), 7.03(dd, J=11.0, 15.0 Hz, 1H), 7.26–7.34(m, 2H).

Example 77

(E,E,E)-7-(3-Methyl-4-dimethylamino-phenyl)-3-methyl-octa-2,4,6-trienoic acid $^1$H-NMR(400 MHz, CDCl$_3$) δ: 2.24(s, 3H), 2.34(s, 3H), 2.39(s, 3H), 2.72(s, 6H), 5.83(s, 1H), 6.39(d, J=15.0 Hz, 1H), 6.57(d, J=11.0 Hz, 1H), 6.99(d, J=8.0 Hz, 1H), 7.08(dd, J=11.0, 15.0 Hz, 1H), 7.24–7.34(m, 3H).

Example 78

Ethyl (E)-3-(3-(1-methylethyl)-4-dimethylaminophenyl)-2-fluoro-2-butenoate $^1$H-NMR(400 MHz, CDCl$_3$) δ: 0.98(t, J=7.2 Hz, 3H), 1.20(d, J=7.2 Hz, 6H), 2.13(d, J=4.8 Hz, 3H), 2.67(s, 6H), 3.50(hept., J=7.2 Hz, 1H), 4.02(q, J=7.2 Hz, 2H), 6.95(dd, J=2.0 Hz, 8.0 Hz, 1H), 7.03(d, J=2.0 Hz, 1H), 7.05(d, J=8.0 Hz, 1H).

Example 79

Methyl (E,E,E)-7-[3-(1-methylethyl)-4-dimethylamino-phenyl]-6-fluoro-3-methyl-octa-2,4,6-trienoate $^1$H-NMR(400 MHz, CDCl$_3$) δ: 1.22(d, J=6.8 Hz, 6H), 2.15(d, J=4.0 Hz, 3H), 2.17(s, 3H), 2.70(s, 6H), 3.52(hept., J=6.8 Hz, 1H), 3.70(s, 3H), 5.86(s, 1H), 6.54(s, 1H), 6.58(dd, J=14.9, 33.4 Hz, 1H), 7.04(dd, J=2.4, 8.4 Hz, 1H), 7.06(d, J=8.4 Hz, 1H), 7.11(d, J=2.4 Hz, 1H).

Example 80

(E,E,E)-7-[3-(1-Methylethyl)-4-dimethylaminophenyl]-6-fluoro-3-methyl-octa-2,4,6-trienoic acid $^1$H-NMR(400 MHz, CDCl$_3$) δ: 1.22(d, J=6.8 Hz, 6H), 2.16(d, J=3.6z, 3H), 2.18(s, 3H), 2.71(s, 6H), 3.53(hept., J=6.4 Hz, 1H), 5.88(s, 1H), 6.58(s, 1H), 6.61(dd, J=15.6, 41.6 Hz, 1H), 7.05(dd, J=2.4, 8.8 Hz, 1H), 7.09(d, J=8.8 Hz, 1H), 7.11(d, J=2.4 Hz, 1H).

The structures of the compounds prepared in Examples 7 to 80 are shown in Tables 2 to 9.

TABLE 2

| Ex. 7 | (structure: N-isopropyl tetrahydroquinoline with methyl, linked to C(CH$_3$)=C(F)COOC$_2$H$_5$) |
|---|---|
| Ex. 8 | (structure: N-isopropyl tetrahydroquinoline with methyl, linked to trienoate with F, COOCH$_3$) |

TABLE 2-continued
Ex. 9
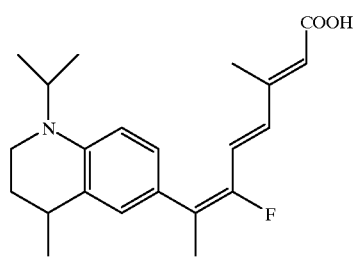
Ex. 10
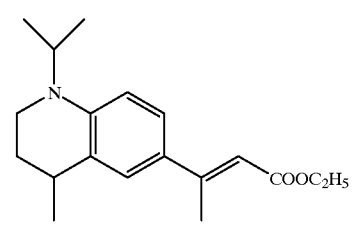
Ex. 11
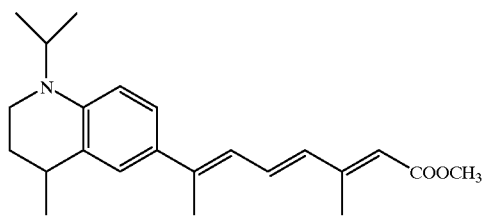
Ex. 12
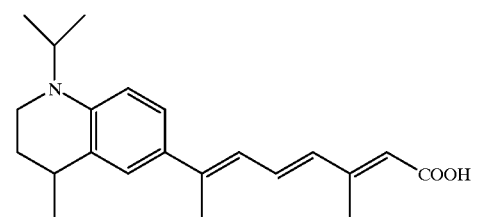
TABLE 2-continued
Ex. 13
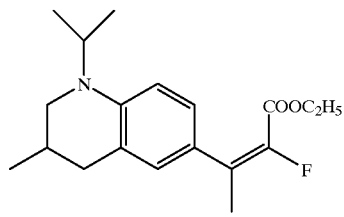
Ex. 14
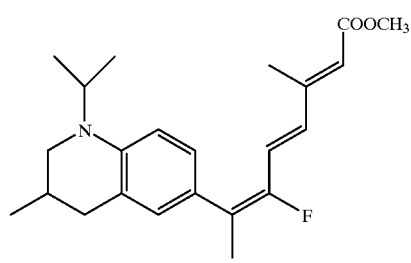
Ex. 15
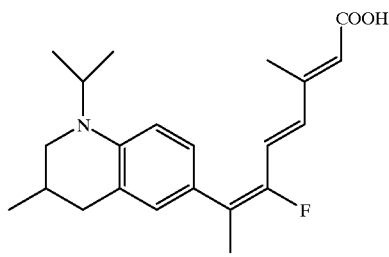
Ex. 16
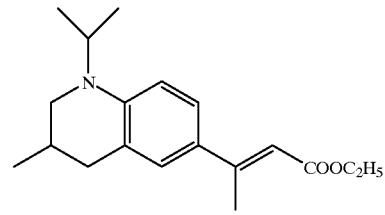
TABLE 3
Ex. 17
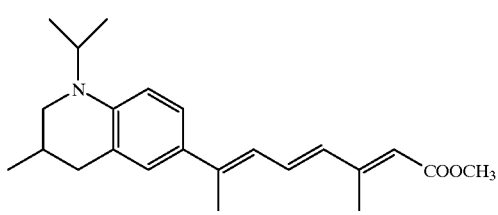

TABLE 3-continued
Ex. 18 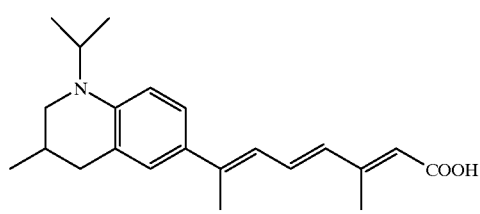
Ex. 19 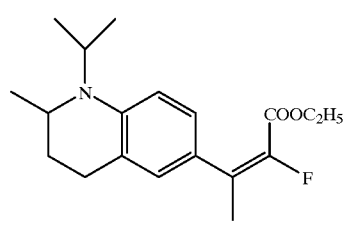
Ex. 20 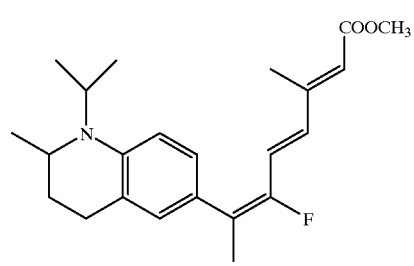
Ex. 21 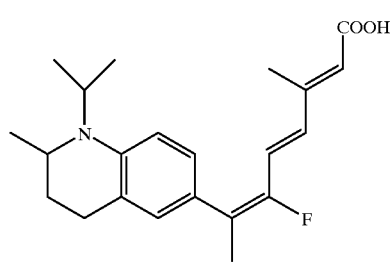
Ex. 22 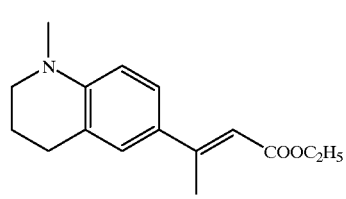
Ex. 23 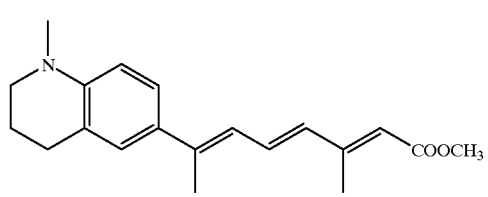
Ex. 24 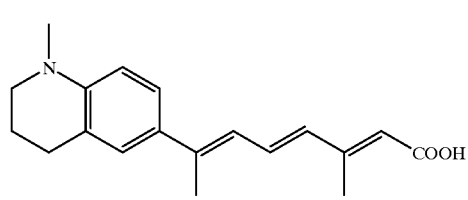

TABLE 3-continued
Ex. 25 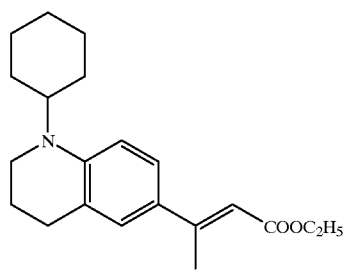
Ex. 26 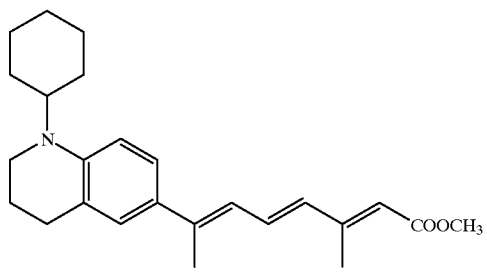
TABLE 4
Ex. 27 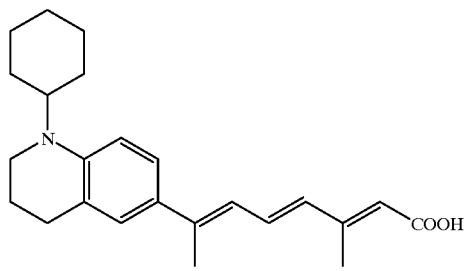
Ex. 28 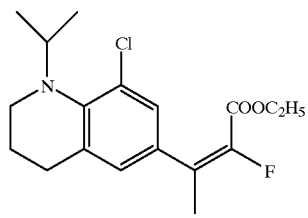
Ex. 29 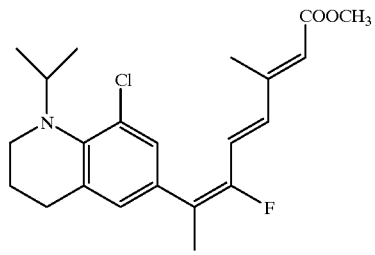
TABLE 4-continued
Ex. 30 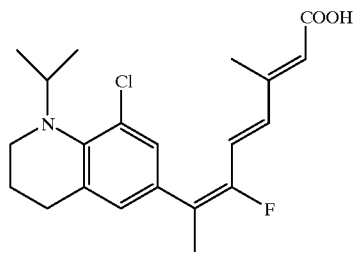
Ex. 31 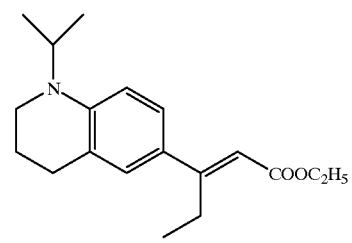
Ex. 32 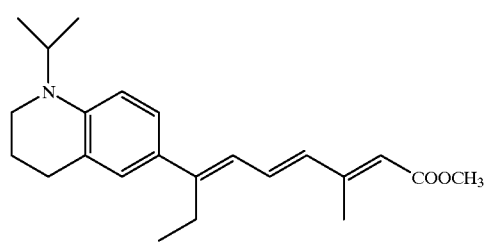

TABLE 4-continued
Ex. 33 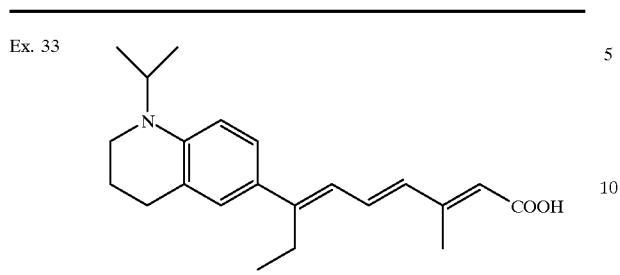
Ex. 34 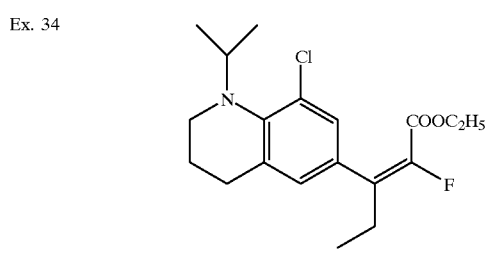
TABLE 4-continued
Ex. 35 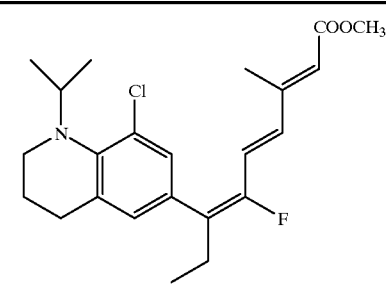
Ex. 36 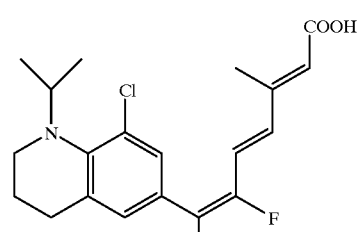
TABLE 5
Ex. 37 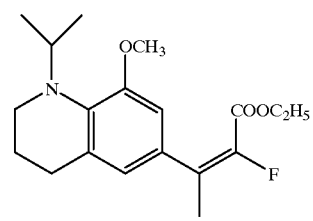
Ex. 38 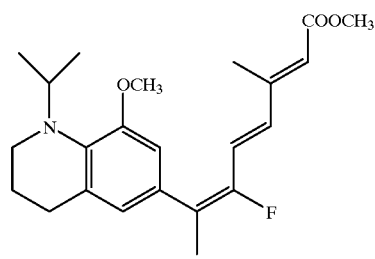
Ex. 39 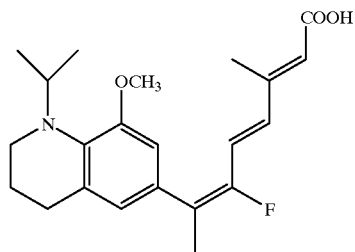

TABLE 5-continued
Ex. 40 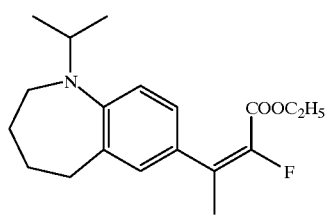
Ex. 41 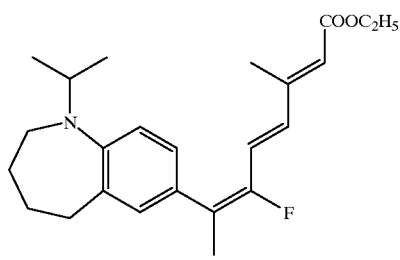
Ex. 42 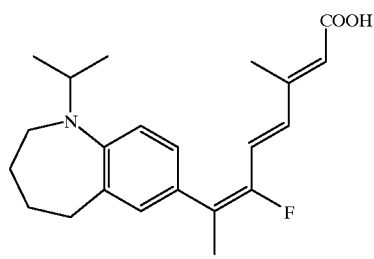
Ex. 43 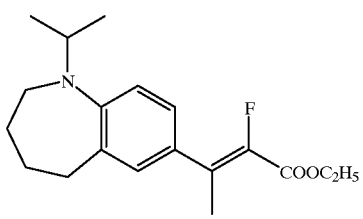
Ex. 44 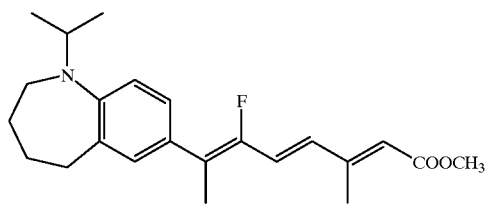
Ex. 45 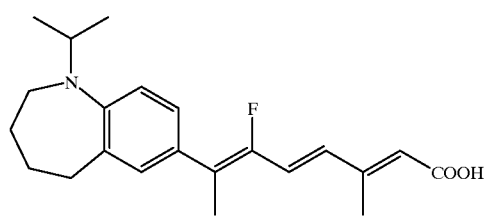

TABLE 5-continued

Ex. 46: [chemical structure]

TABLE 6

Ex. 47: [chemical structure]

Ex. 48: [chemical structure]

Ex. 49: [chemical structure]

Ex. 50: [chemical structure]

Ex. 51: [chemical structure]

TABLE 6-continued

Ex. 52: [chemical structure]

Ex. 53: [chemical structure]

Ex. 54: [chemical structure]

Ex. 55: [chemical structure]

Ex. 56: [chemical structure]

TABLE 7
Ex. 57
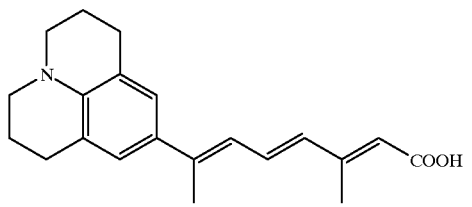
Ex. 58
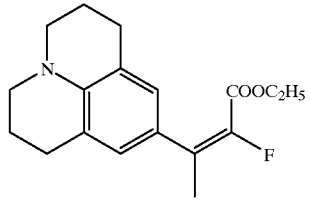
Ex. 59
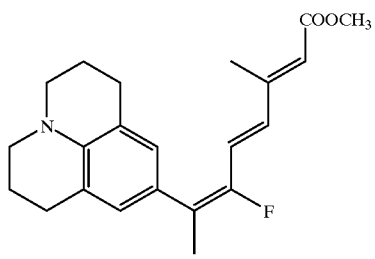
Ex. 60
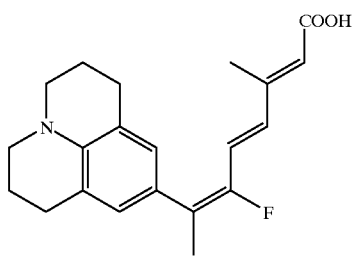
Ex. 61
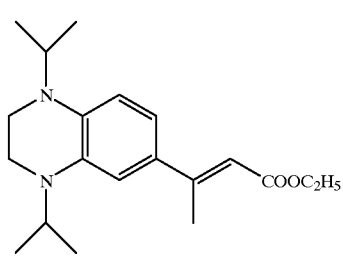
Ex. 62
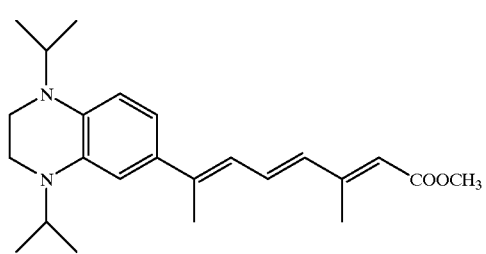
TABLE 7-continued
Ex. 63
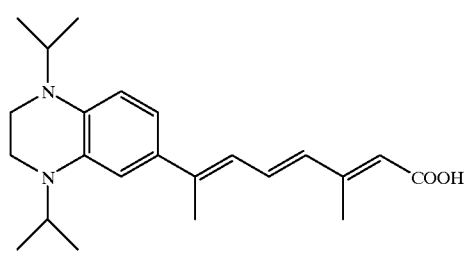
Ex. 64
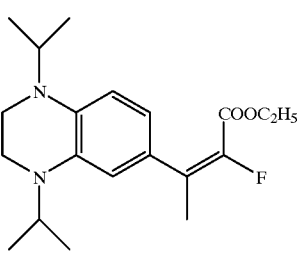
Ex. 65
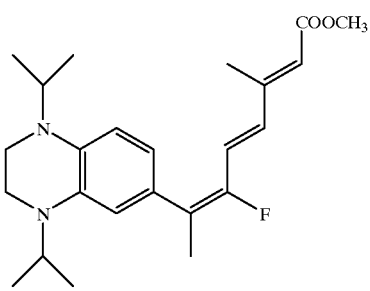
Ex. 66
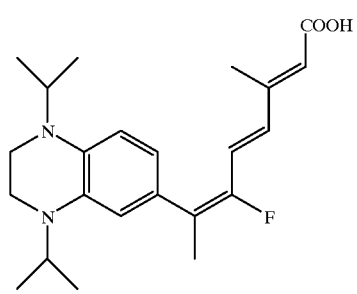
TABLE 8
Ex. 67
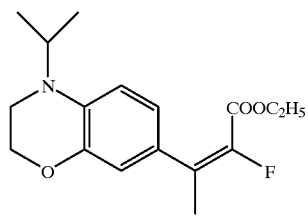

TABLE 8-continued
Ex. 68 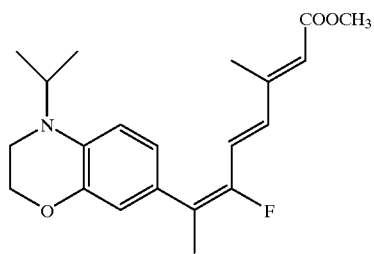
Ex. 69 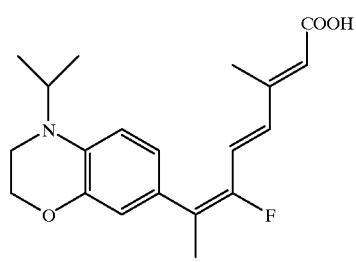
Ex. 70 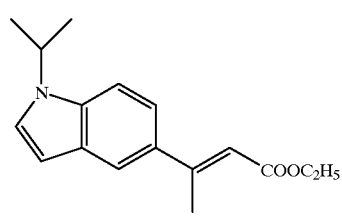
Ex. 71 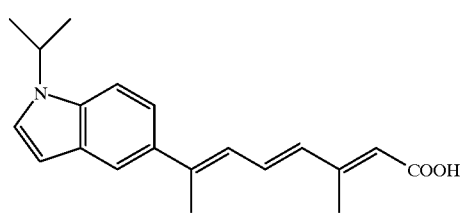
Ex. 72 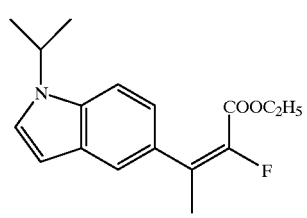
Ex. 73 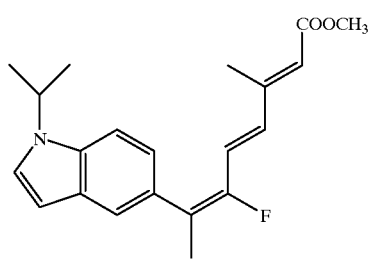
TABLE 8-continued
Ex. 74 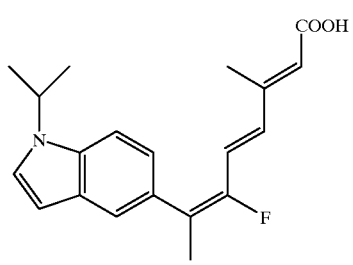
Ex. 75 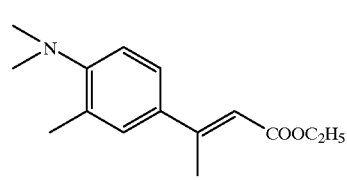
Ex. 76 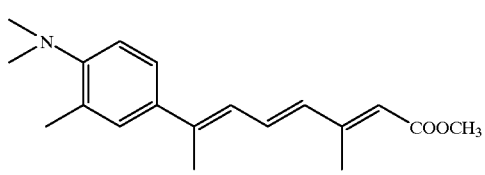
TABLE 9
Ex. 77 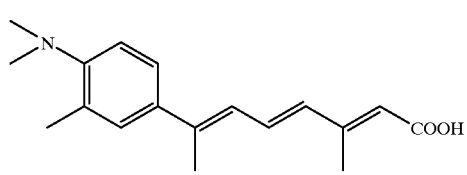
Ex. 78 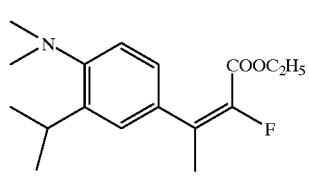
Ex. 79 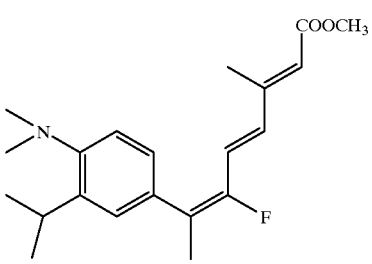

TABLE 9-continued

Ex. 80

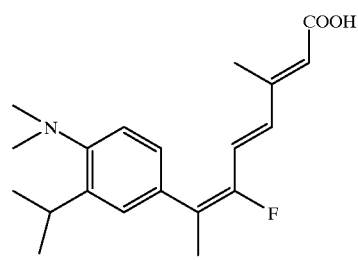

Example 81

(E,E,E)-6-Fluoro-7-[2-(5,6,7,8-tetrahydro-5,5,8,8-tetramethylquinoxalinyl)]-3-methyl-octa-2,4,6-trienoic acid

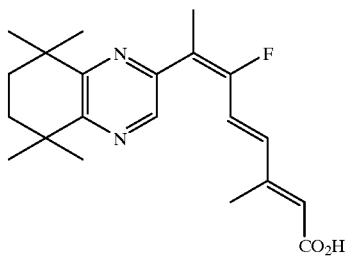

Step 1

Ethyl (E)-2-fluoro-3-[2-(5,6,7,8-tetrahydro-5,5,8,8-tetramethylquinoxalinyl)]-2-butenoate

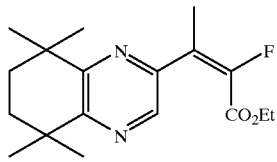

186 mg of sodium hydride was suspended in 10 ml of N,N-dimethylformamide. A solution of 0.94 ml of ethyl 2-fluoro-diethylphosphonoacetate in 5 ml of N,N-dimethylformamide was dropped into the obtained suspension in a nitrogen stream at 0° C., followed by the stirring for 30 minutes. A solution of 540 mg of 2-acetyl-5,6,7,8-tetrahydro-5,5,8,8-tetramethyl- quinoxaline in 10 ml of N,N-dimethylformamide was dropped into the mixture prepared above. The mixture thus obtained was stirred for one hour, followed by the addition of a saturated aqueous solution of ammonium chloride. The resulting mixture was extracted with ethyl acetate. The organic phase was washed with water and a saturated aqueous solution of common salt successively, dried over anhydrous magnesium sulfate and concentrated in a vacuum. The obtained residue was subjected to silica gel column chromatography (developer: 2% ethyl acetate/n-hexane) to give 290 mg of the title compound as a colorless oil.

$^1$H-NMR(400 MHz, CDCl$_3$) δ:
1.01(t, J=7.2 Hz, 3H), 1.30(s, 6H), 1.33(s, 6H), 1.80(s, 4H), 2.19(d, J=4.2 Hz, 3H), 4.07(q, J=7.2 Hz, 2H), 8.24(s, 1H).

Step 2

(E)-2-Fluoro-3-[2-(5,6,7,8-tetrahydro-5,5,8,8-tetramethylquinoxalinyl)]-2-butenal

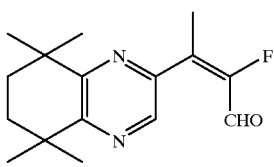

290 mg of ethyl (E)-2-fluoro-3-[2-(5,6,7,8-tetrahydro-5,5,8,8-tetramethylquinoxalinyl)]-2-butenoate was dissolved in 15 ml of tetrahydrofuran. 2.9 ml of diisobutylaluminum hydride (1.5 M toluene solution) was dropped into the solution prepared above in a nitrogen stream at −78° C. The mixture thus obtained was stirred for 2 hours. The reaction was stopped by the addition of a saturated aqueous solution of ammonium chloride, followed by the extraction with ethyl acetate. The organic phase was washed with water and a saturated aqueous solution of common salt successively, dried over anhydrous magnesium sulfate and concentrated in a vacuum to give 270 mg of a colorless oil. Then, a solution of 1.4 ml of dimethyl sulfoxide in 4 ml of dichloromethane was dropped into a solution of 0.85 ml of oxalyl chloride in 40 ml of dichloromethane in a nitrogen stream at −60° C., followed by the stirring for 5 minutes. A solution of 270 mg of the colorless oil prepared above in 10 ml of dichloromethane was dropped into the obtained mixture. The mixture thus obtained was stirred for 15 minutes, followed by the dropwise addition of 6.5 ml of triethylamine. The obtained mixture was stirred for 5 minutes, and the temperature of the mixture was raised to room temperature. The resulting mixture was stirred for 15 minutes, followed by the addition of water. The obtained mixture was extracted with dichloromethane. The organic phase was washed with water and a saturated aqueous solution of common salt successively, dried over anhydrous magnesium sulfate and concentrated in a vacuum. The obtained residue was subjected to silica gel column chromatography (developer: 5% ethyl acetate/n-hexane) to give 230 mg of the title compound as a yellow solid.

$^1$H-NMR(400 MHz, CDCl$_3$) δ:
1.32(s, 6H), 1.35(s, 6H), 1.83(s, 4H), 2.36(d, J=4.0 Hz, 3H), 8.47(s, 1H), 9.70(d, J=19.0 Hz, 1H).

Step 3

(E,E,E)-6-Fluoro-7-[2-(5,6,7,8-tetrahydro-5,5,8,8-tetramethylquinoxalinyl)]-3-methyl-octa-2,4,6-trienoic acid

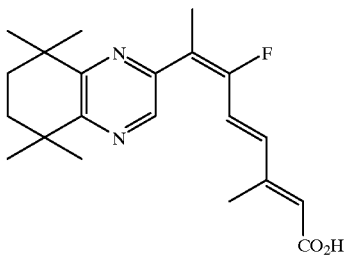

65 mg of metallic sodium was added to methanol to prepare a methanolic solution of sodium methoxide. This solution was concentrated in a vacuum and suspended in 10 ml of N,N-dimethylformamide. 0.89 g of triethyl 3-methyl-4-phosphonocrotonate and a solution of 230 mg of (E)-2-fluoro-3-[2-(5,6,7,8-tetrahydro-5,5,8,8-tetramethylquinoxalinyl)]-2-butenal in 10 ml of N,N-dimethylformamide were added to the obtained suspension successively in a nitrogen stream at 0° C. The obtained mixture was stirred for 30 minutes, followed by the addition of a saturated aqueous solution of ammonium chloride. The obtained mixture was extracted with ethyl acetate. The organic phase was washed with water and a saturated aqueous solution of common salt successively, dried over anhydrous magnesium sulfate and concentrated in a vacuum. The obtained residue was subjected to silica gel column chromatography (developer: 5% ethyl acetate/n-hexane) to give 220 mg of a pale-yellow solid. This solid was hydrolyzed in a similar manner to that described in Step 4 of Example 2 to give 60 mg of the title compound as a light-brown solid.

$^1$H-NMR(400 MHz, DMSO-d$_6$) δ:
1.27(s, 6H), 1.29(s, 6H), 1.76(s, 4H), 2.16(s, 3H), 2.20(bs, 3H), 6.00(s, 1H), 6.76(d, J=15.2 Hz, 1H), 7.26(dd, J=15.2, 30.5 Hz, 1H), 8.58(s, 1H).

Example 82

(E,E,Z)-6-Fluoro-7-[2-(5,6,7,8-tetrahydro-5,5,8,8-tetramethylcuinoxalinyl)]-3-methyl-octa-2,4,6-trienoic acid

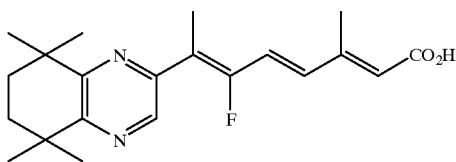

Step 1

Ethyl (Z)-2-fluoro-3-[2-(5,6,7,8-tetrahydro-5,5,8,8-tetramethylquinoxalinyl)]-2-butenoate

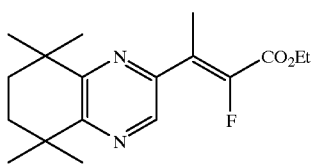

165 mg of the title compound was obtained as a colorless oil in a similar manner to that described in Step 1 of Example 81 through silica gel column chromatography.

$^1$H-NMR(400 MHz, CDCl$_3$) δ:
1.31(s, 6H), 1.34(s, 6H), 1.39(t, J=7.2 Hz, 3H), 1.80(s, 4H), 2.50(d, J=3.6 Hz, 3H), 4.36(q, J=7.2 Hz, 2H), 8.65(d, J=3.6 Hz, 1H).

Step 2

(E,E,Z)-6-Fluoro-7-[2-(5,6,7,8-tetrahydro-5,5,8,8-tetramethylquinoxalinyl)]-3-methyl-octa-2,4,6-trienoic acid

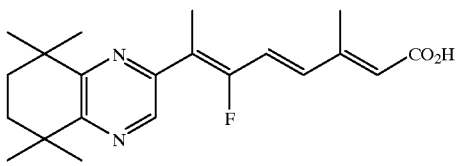

The title compound was obtained as a pale-yellow solid in a similar manner to that described in Steps 2 and 3 of Example 81.

$^1$H-NMR(400 MHz, CDCl$_3$) δ:
1.32(s, 6H), 1.34(s, 6H), 1.80(s, 4H), 2.25(d, J=2.2 Hz, 3H), 2.40(s, 3H), 5.99(s, 1H), 6.76(d, J=15.6 Hz, 1H), 6.90(dd, J=15.6, 26.4 Hz, 1H), 8.79(d, J=2.7 Hz, 1H).

Example 83

(E,E,Z)-7-[2-(5,6,7,8-Tetrahydro-5,5,8,8-tetramethylquinoxalinyl)]-3-methyl-octa-2,4,6-trienoic acid

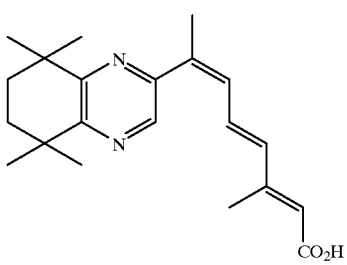

Step 1

Ethyl (Z)-3-[2-(5,6,7,8-tetrahydro-5,5,8,8-tetramethylquinoxalinyl)]-2-butenoate

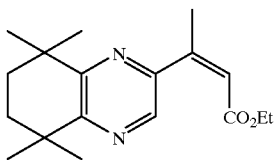

48 mg of sodium hydride was suspended in 10 ml of N,N-dimethylformamide, and 0.36 ml of ethyl diethylphosphonoacetate was dropped into the suspension in a nitrogen stream at 0° C. The obtained mixture was stirred for 30 minutes, followed by the dropwise addition of a solution of 140 mg of 2-acetyl-5,6,7,8-tetrahydro-5,5,8,8-tetramethylquinoxaline in 10 ml of N,N-dimethylformamide. The obtained mixture was heated to 60° C. and stirred for 48 hours, followed by the addition of a saturated acueous solution of ammonium chloride. The obtained mixture was extracted with ethyl acetate. The organic phase was washed with water and a saturated aqueous solution of common salt successively, dried over anhydrous magnesium sulfate and concentrated in a vacuum. The obtained residue was subjected to silica gel column chromatography (developer: 2% ethyl acetate/n-hexane) to give 120 mg of the title compound as a colorless oil.

¹H-NMR(400 MHz, CDCl₃) δ:
  1.32(s, GH), 1.33(s, 6H), 1.34(t, J=7.1 Hz, 3H), 1.80(s, 4H), 2.61(d, J=1.3 Hz, 3H), 4.24(q, J=7.1 Hz, 2H), 6.75(q, J=1.3 Hz, 1H), 8.58(s, 1H).

Step 2

(E,E,Z)-7-[2-(5,6,7,8-Tetrahydro-5,5,8,8-tetramethylquinoxalinyl)]-3-methyl-octa-2,4,6-trienoic acid

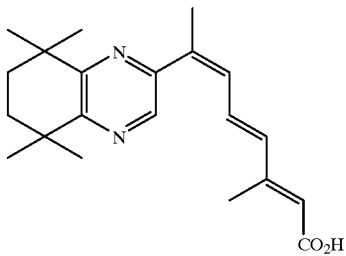

The title compound was obtained in a similar manner to that described in Steps 2 and 3 of Example 81.
¹H-NMR(400 MHz, CDCl₃) δ:
  1.29(s, 6H), 1.32(s, 6H), 1.78(s, 4H), 2.32(s, 3H), 2.40(s, 3H), 5.89(s, 1H), 6.54(d, J=15.0 Hz, 1H), 7.12(dd, J=12.1, 15.0 Hz, 1H), 7.23(d, J=12.1 Hz, 1H), 8.55(s, 1H).

Example 84

(E,E)-5-[3-(7,8,9,10-Tetrahydro-7,7,10,10-tetramethylphenazinyl)]-3-methyl-2,4-pentadienoic acid

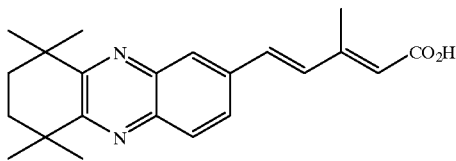

Step 1

7,8,9,10-Tetrahydro-7,7,10,10-tetramethyl-phenazine-3-carbaldehyde

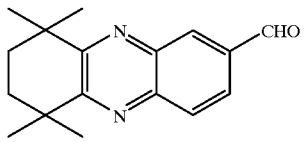

1.17 g of methyl 7,8,9,10-tetrahydro-7,7,10,10-tetramethyl-3-phenazinecarboxylate was dissolved in 50 ml of tetrahydrofuran. 10.5 ml of diisobutylaluminum hydride (1.5M toluene solution) was dropped into the solution in a nitrogen stream at −78° C., followed by the stirring for 30 minutes. A saturated aqueous solution of ammonium chloride was added to the reaction mixture to stop the reaction, followed by the extraction with ethyl acetate. The organic phase was washed with water and a saturated aqueous solution of common salt successively, dried over anhydrous magnesium sulfate and concentrated in a vacuum to give a colorless oil. This oil was dissolved in 10 ml of dichloromethane, followed by the addition of 5.0 g of manganese dioxide. The obtained mixture was stirred overnight and filtered through Celite. The filtrate was concentrated in a vacuum to give 0.83 g of the title compound as a pale-yellow solid.
¹H-NMR(400 MHz, CDCl) δ:
  1.45(s, 12H), 1.93(s, 4H), 8.07(d, J=8.8 Hz, 1H), 8.13(dd, J=1.8, 8.6 Hz, 1H), 8.48(d, J=1.8 Hz, 1H), 10.22(s, 1H).

Step 2

(E,E)-5-[3-(7,8,9,10-Tetrahydro-7,7,10,10-tetramethylphenazinyl)]-3-methyl-2,4-pentadienoic acid

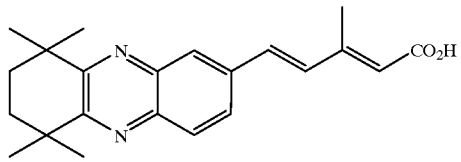

The title compound was prepared in a similar manner to that described in Step 3 of Example 81.
¹-H-NMR(400 MHz, DMSO-d₆) δ:
  1.36(s, 6H), 1.37(s, 6H), 1.86(s, 4H), 2.34(s, 3H), 6.04(s, 1H), 7.23(d, J=16.0 Hz, 1H), 7.33(d, J=16.0 Hz, 1H), 7.92(d, J=8.8 Hz, 1H), 8.02(dd, J=1.3, 8.8 Hz, 1H), 8.12(d, J=1.3 Hz, 1H).

Example 85

Ethyl (E)-3-[6-(2,3-diisopropylquinoxalinyl)]-2-butenoate

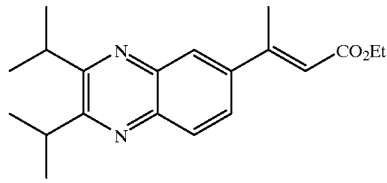

Step 1

2,3-Diisopropylquinoxaline-6-ethanone

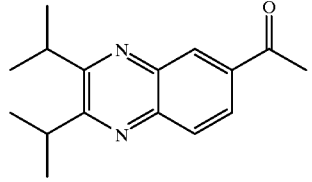

The title compound was prepared by the use of 2,3-diisopropyl-6-quinoxalinal in a similar manner to that described in Steps 3 and 4 of Example 1.

¹H-N (400 MHz, CDCl₃) δ:
  1.36–1.42(m, 12H), 2.77(s, 3H), 3.48–3.60(m, 2H), 8.04 (d, J=8.8 Hz, 1H), 8.23(dd, J=2.2, 8.8 Hz, 1H), 8.58(d, J=2.2 Hz, 1H).

Step 2

Ethyl (E)-3-[6-(2,3-diisopropylquinoxalinyl)]-2-butenoate

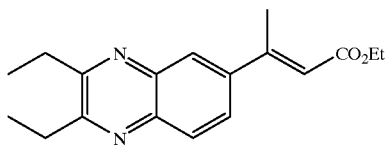

The title compound was prepared in a similar manner to that described in Step 1 of Example 83.

$^1$H-NMR(400 MHz, CDCl$_3$) δ:

1.34(t, J=7.1 Hz, 3H), 1.38(d, J=6.6 Hz, 6H), 1.39(d, J=6.8 Hz, 6H), 2.70(d, J=1.3 Hz, 3H), 3.54 (hept., J=6.8 Hz, 2H), 4.24 (q, J=7.1 Hz, 2H), 6.33(d, J=1.3 Hz, 1H), 7.77(dd, J=2.2, 8.8 Hz, 1H), 7.97(d, J=8.8 Hz, 1H), 8.12(d, J=2.2 Hz, 1H).

Example 86

(E,E,E)-7-[6-(2,3-Diisopropylquinoxalinyl)]-3-methyl-octa-2,4,6-trienoic acid

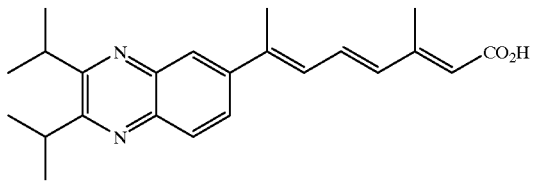

Step 1

(E)-3-[6-(2,3-Diisopropylquinoxalinyl)]-2-butenal

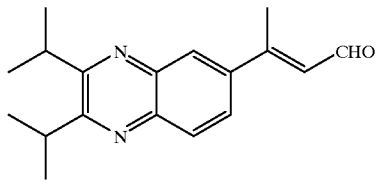

The title compound was prepared by the use of ethyl (E)-3-[6-(2,3-diisopropylquinoxalinyl)]-2-butenoate in a similar manner to that described in Step 1 of Example 84.

$^1$H-NMR(400 MHz, CDCl$_3$) δ:

1.39(d, J=6.6 Hz, 6H), 1.40(d, J=6.8 Hz, 6H), 2.70(d, J=1.3 Hz, 3H), 3.50–3.60(m, 2H), 6.57(dd, J=1.3, 7.6 Hz, 1H), 7.82(dd, J=2.0, 8.8 Hz, 1H), 1.01(d, J=8.8 Hz, 1H), 8.20(d, J=2.0 Hz, 1H), 10.25(d, J=7.6 Hz, 1H).

Step 2

(E,E,E)-7-[6-(2,3-Diisopropylquinoxalinyl)]-3-methyl-octa-2,4,6-trienoic acid

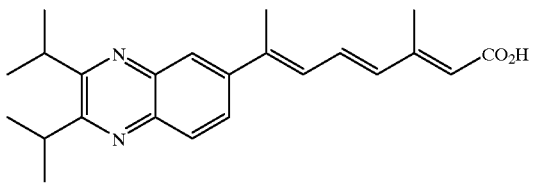

The title compound was prepared in a similar manner to that described in Step 3 of Example 81.

$^1$H-NMR(400 MHz, CDCl$_3$) δ:

1.39(d, J=6.6 Hz, 6H), 1.40(d, J=6.8 Hz, 6H), 2.40(s, 3H), 2.42(s, 3H), 3.48–3.59(m, 2H), 5.89(s, 1H), 6.49(d, J=14.7 Hz, 1H), 6.83(d, J=10.5 Hz, 1H), 7.14(dd, J=10.5, 14.7 Hz, 1H), 7.85(dd, J=2.2, 8.8 Hz, 1H), 7.95(d, J=8.8 Hz, 1H), 8.07(d, J=2.2 Hz, 1H).

The following compounds were prepared in a similar manner to that described above.

Example 87

(E,E,Z)-7-[2-(5,5,7,7-Tetramethylcyclopenta[b]pyrazinyl)]-3-methyl-octa-2,4,6-trienoic acid

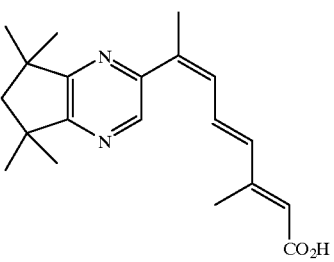

$^1$H-N (400 MHz, DMSO-d$_6$) δ:

1.28(s, 6H), 1.29(s, 6H), 1.96(s, 2H), 2.28(s, 3H), 2.30(s, 3H), 5.87(s, 1E), 6.65(d, J=14.8 Hz, 1H), 7.11(dd, J=10.8, 14.8 Hz, 1H), 7.31(d, J=10.8 Hz, 1H), 8.65(s, 1H).

Example 88

(E,E)-5-[3-(7,8,9,10-Tetrahydrophenazinyl)]-3-methyl-2,4-pentadienoic acid

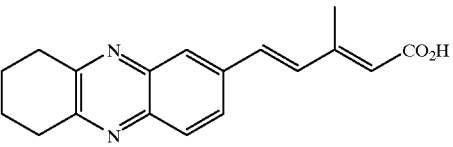

$^1$H-NNR(400 MHz, DMSO-d$_6$) δ:

1.92–1.98(m, 4H), 2.35(s, 3H), 3.02–3.07(m, 4H), 6.03(s, 1H), 7.23(d, J=15.5 Hz, 1H), 7.29(d, J=15.5 Hz, 1H), 7.89(d, J=8.6 Hz, 1H), 8.02(dd, J=1.9, 8.6 Hz, 1H), 8.07(d, J=1.9Hz, 1H).

Example 89

(E,E)-5-[6-(2,3-Diethylquinoxalinyl)]-3-methyl-2,4-pentadienoic acid

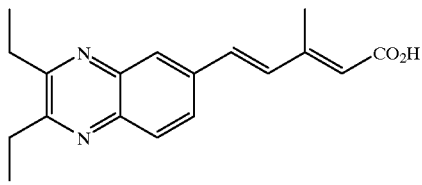

$^1$H-NMR(400 MHz, DMSO-$d_6$) δ:
1.32(t, J=7.3 Hz, 3H), 1.33(t, J=7.3 Hz, 3H), 2.35(s, 3H), 3.00 (q, J=7.3 Hz, 2H), 3.01(q, J=7.3 Hz, 2H), 6.04(s, 1H), 7.23(d, J=16.3 Hz, 1H), 7.30(d, J=16.1 Hz, 1H), 7.94(d, J=8.6 Hz, 1H), 8.01(dd, J=1.6, 8.6 Hz, 1H), 8.13(d, J=1.3 Hz, 1H), 12.19(bs, 1H)

Example 90

(E,E)-5-[6-(2,3-Diisopropylquinoxalinyl)]-3-methyl-2,4-pentadienoic acid

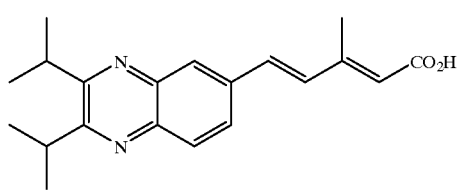

$^1$H-NMR(4 MHz, DMSO-$d_6$) δ:
1.37(d, J=6.8 Hz, 12H), 2.46(s, 3H), 3.48–3.60(m, 2H), 6.01(s, 1H), 7.03(d, J=16.1 Hz, 1H), 7.16(d, J=16.1 Hz, 1H), 7.80(dd, J=2.0, 8.4 Hz, 1H), 7.97(d, J=8.8 Hz, 1H), 8.05(d, J=1.8 Hz, 1H).

Example 91

(E,E)-5-[6-[2,3-Di(3-pentyl)quinoxalinyl]]-3-methyl-2,4-pentadienoic acid

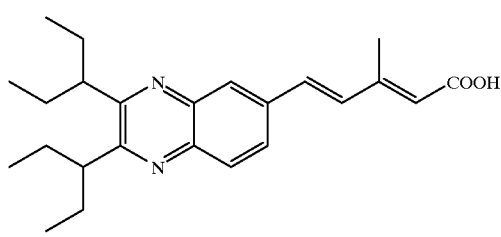

$^1$H-NMR(400 MHz, DMSO-$d_6$) δ:
0.78(t, J=7.3 Hz, 12H), 1.64–1.76(m, 4H), 1.80–1.89(m, 4H), 2.34(s, 3H), 3.13–3.22(m, 2H), 6.05(s, 1H), 7.25 (d, J=16.0 Hz, 1H), 7.33(d, J=16.0 Hz, 1H), 7.94(d, J=8.8 Hz, 1H), 8.01(dd, J=1.6, 8.8 Hz, 1H), 8.14(d, J=1.6 Hz, 1H).

Example 92

(E,E)-5-[6-(2,3-Dicyclopropylquinoxalinyl)]-3-methyl-2,4-pentadienoic acid

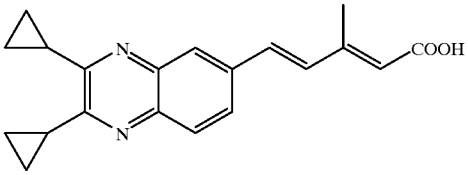

$^1$H-NMR(400 MHz, DMSO-$d_6$) δ:
1.06–1.18(m, 4H), 2.32(s, 3H), 2.68–2.76(m, 2H), 6.01(s, 1H), 7.18(d, J=16.2 Hz, 1H), 7.26(d, J=16.2 Hz, 1H), 7.79(d, J=8.6 Hz, 1H), 7.89–7.93(m, 1H), 7.99(bs, 1H).

Example 93

(E,E)-5-[6-(2,3-Dicyclobutylquinoxalinyl)]-3-methyl-2,4-pentadienoic acid

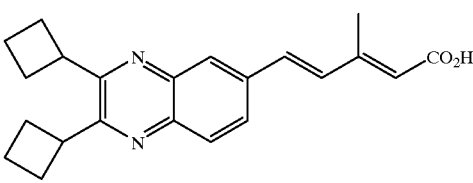

$^1$H-NMR(400 MHz, DMSO-$d_6$) δ:
1.80–1.90(m, 2H), 2.00–2.15(m, 2H), 2.27–2.50(m, 8H), 3.86–3.96(m, 2H), 6.05(s, 1H), 7.24(d, J=16.4 Hz, 1H), 7.33(d, J=16.0 Hz, 1H), 7.97(d, J=8.8 Hz, 1H), 8.02(dd, J=1.2, 8.8 Hz, 1H), 8.18(s, 1H).

Example 94

(E,E)-5-[6-(2,3-Dicyclopentylquinoxalinyl)]-3-methyl-2,4-pentadienoic acid

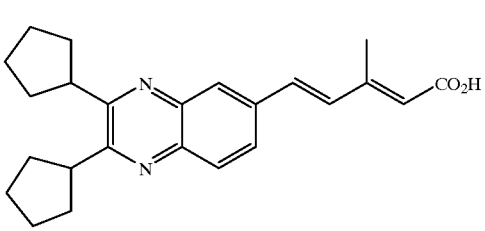

$^1$H-NMR(400 MHz, DMSO-$d_6$) δ:
1.64–1.74(m, 4H), 1.75–1.88(m, 4H), 1.88–1.95(m, 4H), 1.99–2.09(m, 2H), 2.34(s, 3H), 3.64–3.73(m, 2H), 6.04 (s, 1H), 7.23(d, J=16.0 Hz, 1H), 7.30(d, J=16.4 Hz, 1H), 7.90(d, J=8.8 Hz, 1H), 7.99(dd, J=1.6, 8.8 Hz, 1H), 8.10(d, J=1.6 Hz, 1H).

Example 95

(E,E)-5-[6-(2,3-Dicyclohexylquinoxalinyl)]-3-methyl-2,4-pentadienoic acid

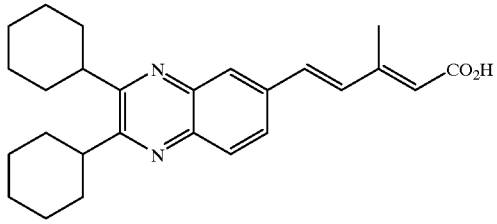

¹H-NMR(400 MHz, DMSO-d₆) δ:
1.23–1.36(m, 2H), 1.38–1.52(m, 4H), 1.60–1.89(m, 12H), 2.34(s, 3H), 3.07–3.18(m, 2H), 6.04(s, 1H), 7.21(d, J=16.1 Hz, 1H), 7.30(d, J=16.1 Hz, 1H), 7.90(d, J=8.6 Hz, 1H), 7.99(dd, J=1.3, 8.6 Hz, 1H), 8.11(d, J=1.3 Hz, 1H).

Example 96

(E,E)-5-[6-[2,3-Di(2-furyl)quinoxalinyl]]-3-methyl-2,4-pentadienoic acid

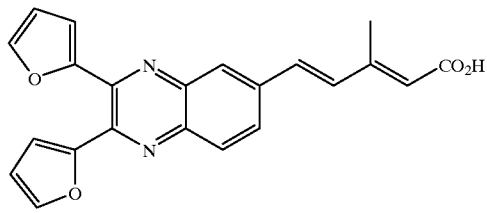

¹H-NMR(400 MHz, DMSO-d₆) δ:
2.16(s, 3H), 5.85(s, 1H), 6.68–6.78(m, 4H), 7.32(d, J=15.0 Hz, 1H), 7.91(bs, 2H), 8.01–8.04(m, 1H), 8.10(d, J=8.6 Hz, 1H), 8.14(bs, 1H), 8.53(d, J=15.0 Hz, 1H).

Example 97

(E,E)-5-[9-(2,2,6,6-Tetramethylthiepa[4,5-b]quinoxalinyl)]-3-methyl-2,4-pentadienoic acid

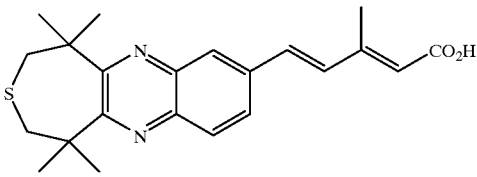

¹H-NMR(400 MHz, CDCl₃) δ:
1.61(s, 12H), 2.47(s, 3H), 2.92(s, 4H), 6.02(s, 1H), 7.01(d, J=16.2 Hz, 1H), 7.16(d, J=16.2 Hz, 1H), 7.78–7.83(m, 1H), 7.91(d, J=8.8 Hz, 1H), 7.98(bs, 1H).

Example 98

(E,E)-5-[2-(3,6,6,9,9-Pentamethylcyclo-hexa[g]quinoxalinyl)]-3-methyl-2,4-pentadienoic acid

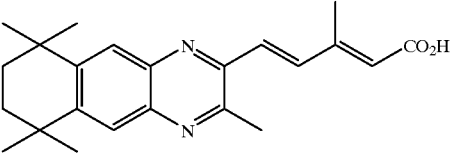

¹H-NMR(400 MHz, DMSO-d₆) δ:
1.35(s, 12H), 1.72(s, 4H), 2.39(s, 3H), 2.76(s, 3H), 6.13(s, 1H), 7.34(d, J=15.0 Hz, 1H), 7.60(d, J=15.0 Hz, 1H), 7.89(s, 1H), 7.94(s, 1H).

Preparative Example 1

1,4-Dimethyl-1,2,3,4-tetrahydrocuinoline-6-carbaldehyde

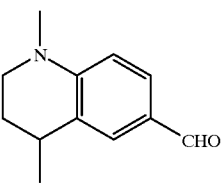

The title compound was prepared from 1,4-dimethyl-1,2,3,4-tetrahydroquinoline in a similar manner to that described in Step 2 of Example 1.

¹H-NMR(400 MHz, CDCl₃) δ:
1.30(d, J=7.2 Hz, 3H), 1.66–1.74(m, 1H), 1.95–2.03(m, 1H), 2.86–2.94(m, 1H), 3.02(s, 3H), 3.33–3.46(m, 2H), 6.57(d, J=9.2 Hz, 1H), 7.55–7.58(m, 2H), 9.68(s, 1H).

Preparative Example 2

1-(1,4-Dimethyl-1,2,3,4-tetrahydroquinolin-6-yl)ethanone

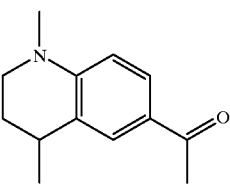

In a similar manner to that described in Steps 3 and 4 of Example 1, the title compound was prepared from 1,4-dimethyl-1,2,3,4-tetrahydroquinoline-6-carbaldehyde prepared in Preparative Example 1.

¹H-NMR(400 MHz, CDCl3) δ:
1.29(d, J=6.8 Hz, 3H), 1.66–1.74(m, 1H), 1.95–2.03(m, 1H), 2.49(s, 3H), 2.86–2.96(m, 1H), 2.99(s, 3H), 3.28–3.43(m, 2H), 6.51(d, J=8.8 Hz, 1H), 7.60–7.72(m, 2H).

Example 99
Ethyl (E)-3-(1,4-dimethyl-1,2,3,4-tetrahydroquinolin-6-yl)-2-butenoate

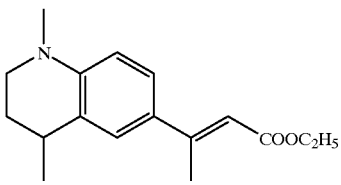

In a similar manner to that described in Step 5 of Example 1, the title compound was prepared from 1-(1,4-dimethyl-1,2,3,4-tetrahydroquinolin-6-yl)ethanone prepared in Preparative Example 2.

$^1$H-NMR(400 MHz, CDCl$_3$) δ:
1.29(t, J=7.2 Hz, 3H), 1.32(d, J=6.8 Hz, 3H), 1.66–1.74 (m, 1H), 1.98–2.06(m, 1H), 2.56(d, J=1.2 Hz, 3H), 2.86–2.96(m, 1H), 2.94(s, 3H), 3.20–3.36(m, 2H), 4.19 (q, J=7.2 Hz, 2H), 6.10(q, J=1.2 Hz, 1H), 6.54(d, J=8.8 Hz, 1H), 7.26(d, J=2.0Hz, 1H), 7.30(dd, J-2.0, 8.4 Hz, 1H).

Preparative Example 3
(E)-3-(1,4-Dimethyl-1,2,3,4-tetrahydroquinolin-6-yl)-2-butenal

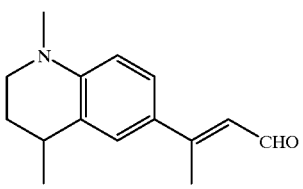

In a similar manner to that described in Steps 1 and 2 of Example 2, the title compound was prepared from ethyl (E)-3-(1,4-dimethyl-1,2,3,4-tetrahydro-auinolin-6-yl)-2-butenoate prepared in Example 99.

$^1$H-NMR(400 MHz, CDCl$_3$) δ:
1.29(d, J=6.8 Hz, 3H), 1.68–1.76(m, 1H), 1.98–2.04(m, 1H), 2.52(d, J=1.2 Hz, 3H), 2.86–2.94(m, 1H), 2.97(s, 3H), 3.24–3.40(m, 2H), 6.43(dd, J=1.2, 8.0 Hz, 1H), 6.56(d, J=8.8 Hz, 1H), 7.26–7.35(m, 1H), 7.38–7.41(m, 1H), 10.11(d, J=8.0 Hz, 1H).

Example 100
Methyl (E,E,E)-7-(1,4-dimethyl-1,2,3,4-tetrahydro-quinolin-6-yl)-3-methyl-octa-2,4,6-trienoate

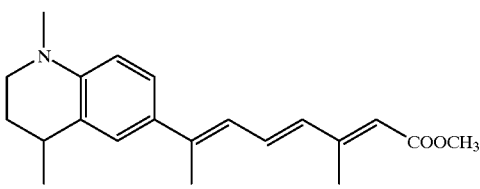

In a similar manner to that described in Step 3 of Example 2, the title compound was prepared from (E)-3-(1,4-dimethyl-1,2,3,4-tetrahydroquinolin-6-yl)-2-butenal prepared in Preparative Example 3.

$^1$H-NMR(400 MHz, CDCl$_3$) δ:
1.30(d, J=7.2 Hz, 3H), 1.66–1.75(m, 1H), 1.98–2.06(m, 1H), 2.22(d, J=1.2 Hz, 3H), 2.39(d, J=1.2 Hz, 3H), 2.86–2.96(m, 1H), 2.93(s, 3H), 3.18–3.34(m, 2H), 3.71 (s, 3H), 5.77(bs, 1H), 6.34(d, J=14.8 Hz, 1H), 6.51–6.57(m, 2H), 7.06(dd, J=11.2, 15.2 Hz, 1H), 7.23–7.27(m, 2H).

Example 101
(E,E,E)-7-(1,4-Dimethyl-1,2,3,4-tetrahydroquinolin-6-yl)-3-methyl-octa-2,4,6-trienoic acid

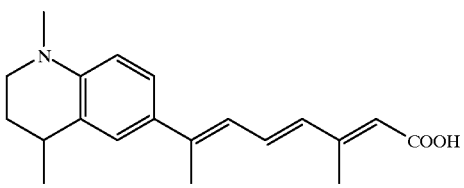

In a similar manner to that described in Step 4 of Example 2, the title compound was prepared from methyl (E,E,E)-7-(1,4-dimethyl-1,2,3,4-tetrahydro-quinolin-6-yl)-3-methyl-octa-2,4,6-trienoate prepared in Example 100.

$^1$H-NMR(400 MHz, CDCl$_3$) δ:
1.30(d, J=7.2 Hz, 3H), 1.65–1.77(m, 1H), 1.96–2.10(m, 1H), 2.22(s, 3H), 2.38(bs, 3H), 2.88–3.00(m, 1H), 2.93(s, 3H), 3.15–3.35(m, 2H), 5.80(bs, 1H), 6.36(d, J=14.8 Hz, 1H), 6.45–6.62(m, 2H), 7.08(dd, J=10.8, 26.0 Hz, 1H), 7.20–7.32(m, 2H).

Preparative Example 4
1,4,4-Trimethyl-1,2,3,4-tetrahydroquinoline-6-carbaldehyde

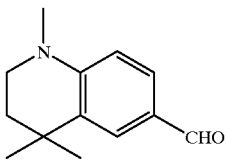

The title compound was prepared from 1,4,4-trimethyl-1,2,3,4-tetrahydroquinoline in a similar manner to that described in Step 2 of Example 1.

$^1$H-NMR(400 MHz, CDCl$_3$) δ:
1.30(s, 6H), 1.74(t, J=6.4 Hz, 2H), 3.03(s, 3H), 3.40(t, J=6.0 Hz, 2H), 6.57(d, J=8.4 Hz, 1H), 7.56(dd, J=2.0, 8.8 Hz, 1H), 7.70(d, J=2.0 Hz, 1H), 9.68(s, 1H).

Example 102
Ethyl (E)-3-(1,4,4-trimethyl-1,2,3,4-tetrahydro-quinolin-6-yl)-2-butenoate

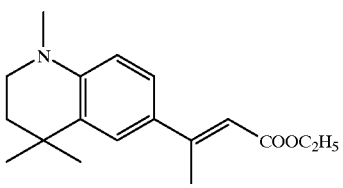

In a similar manner to that described in Steps 3, 4 and 5 of Example 1, the title compound was prepared from 1,4, 4-trimethyl-1,2,3,4-tetrahydroquinoline-6-carbaldehyde prepared in Preparative Example 4.

$^1$H-NMR(400 MHz, CDCl$_3$) δ:
1.30(s, 6H), 1.32(t, J=7.2 Hz, 3H), 1.76(t, J=6.0 Hz, 2H), 2.57(d, J=1.2 Hz, 3H), 2.94(s, 3H), 3.29(t, J=6.0 Hz,

2H), 4.20(q, J=6.8 Hz, 2H), 6.09(q, J=1.2 Hz, 1H), 6.54(d, J=8.8 Hz, 1H), 7.29(dd, J=2.4, 8.4 Hz, 1H), 7.39(d, J=2.4 Hz, 1H).

Preparative Example 5
(E)-3-(1,4,4-Trimethyl-1,2,3,4-tetrahydroquinolin-6-yl)-2-butenal

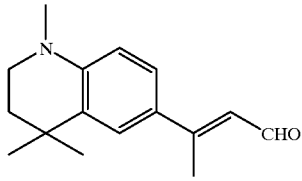

In a similar manner to that described in Steps 1 and 2 of Example 2, the title compound was prepared from ethyl (E)-3-(1,4,4-trimethyl-1,2,3,4-tetrahydroquinolin-6-yl)-2-butenoate prepared in Example 102.
$^1$H-NMR(400 MHz, CDCl$_3$) δ:
1.30(s, 6H), 1.76(t, J=6.0 Hz, 2H), 2.53(d, J=0.8 Hz, 3H), 2.98(s, 3H), 3.33(t, J=6.0 Hz, 2H), 6.43(bd, J=9.2 Hz, 1H), 7.36–7.40(m, 1H), 7.49(d, J=2.4 Hz, 1H), 10.12(d, J=9.2 Hz, 1H).

Example 103
Methyl (E,E,E)-7-(1,4,4-trimethyl-1,2,3,4-tetrahydroquinolin-6-yl)-3-methyl-octa-2,4,6-trienoate

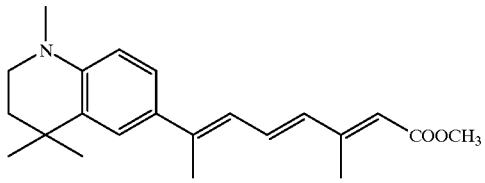

In a similar manner to that described in Step 3 of Example 2, the title compound was prepared from (E)-3-(1,4,4-trimethyl-1,2,3,4-tetrahydroquinolin-6-yl)-2-butenal prepared in Preparative Example 5. $^1$H-NMR(400 MHz, CDCl$_3$) δ:
1.31(s, 6H), 1.77(t, J=6.0 Hz, 2H), 2.22(d, J=1.2 Hz, 3H), 2.39(d, J=1.2 Hz, 3H), 2.93(s, 3H), 3.27(t, J=6.0 Hz, 2H), 3.71(s, 3H), 5.78(s, 1H), 6.34(d, J=15.2 Hz, 1H), 6.51–6.56(m, 2H), 7.06(dd, J=10.8, 14.4 Hz, 1H), 7.25 (dd, J=2.4, 6.0 Hz, 1H), 7.37(d, J=2.4 Hz, 1H).

Example 104
(E,E,E)-7-(1,4,4-Trimethyl-1,2,3,4-tetrahydroquinolin-6-yl)-3-methyl-octa-2,4,6-trienoic acid

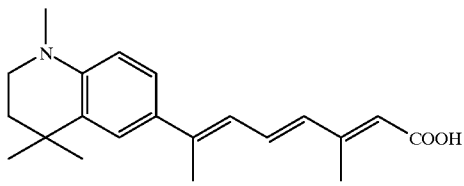

In a similar manner to that described in Step 4 in Example 2, the title compound was prepared from methyl (E,E,E)-7-(1,4,4-trimethyl-1,2,3,4-tetrahydroquinolin-6-yl)-3-methyl-octa-2,4,6-trienoate prepared in Example 103.

$^1$H-NMR(400 MHz, CDCl$_3$) δ:
1.32(s, 6H), 1.77(t, J=6.0 Hz, 2H), 2.23(bs, 3H), 2.39(bs, 3H), 2.94(s, 3H), 3.27(t, J=6.0 Hz, 2H), 5.80(s, 1H), 6.37(d, J=15.2 Hz, 1H), 6.51–6.57(m, 2H), 7.11(dd, J=11.2, 14.8 Hz, 1H), 7.24–7.27(m, 1H), 7.38 (d, J=2.4 Hz, 1H).

Preparative Example 6

1,5,5-Trimethyl-2,3,4,5-tetrahydro-iH-benzazepine-7-carbaldehyde

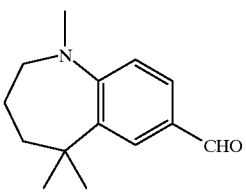

The title compound was prepared from 1,5,5-trimethyl-2,3,4,5-tetrahydro-1H-benzazepine in a similar manner to that described in Step 2 of Example 1.

$^1$H-NMR(400 MHz, CDCl$_3$) δ:
1.39(s, 6H), 1.66(t, J=6.4 Hz, 2H), 1.78–1.86(m, 2H), 2.97(s, 3H), 3.05(t, J=5.6 Hz, 2H), 6.95(d, J=8.4 Hz, 1H), 7.61(dd, J=2.0, 8.4 Hz, 1H), 7.83(d, J=1.6 Hz, 1H).

Preparative Example 7

1-(1,5,5-Trimethyl-2,3,4,5-tetrahydro-1H-benzazepin-7-yl)ethanone

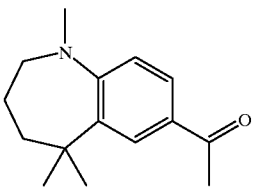

In a similar manner to that described in Steps 3 and 4 of Example 1, the title compound was prepared from 1,5,5-trimethyl-2,3,4,5-tetrahydro-1H-benzazepine-7-carbaldehyde prepared in Preparative Example 6

$^1$H-NMR(400 MHz, CDCl$_3$) δ:
1.39(s, 6H), 1.64(t, J=6.0 Hz, 2H), 1.77–1.84(m, 2H), 2.54(s, 3H), 2.94(s, 3H), 2.99(t, J=6.0 HZ, 2H), 6.90(d, J=8.4 Hz, 1H), 7.72(dd, J=2.0, 8.4 Hz, 1H), 7.97(d, J=2.4 Hz, 1H).

Example 105
Ethyl (E)-3-(1,5,5-trimethyl-2,3,4,5-tetrahydro-1H-benzazepin-7-yl)-2-butenoate

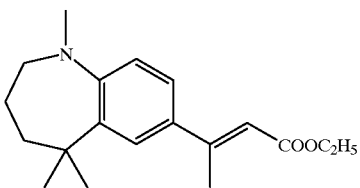

In a similar manner to that described in Step 5 of Example 1, the title compound was prepared from 1-(1,5,5-trimethyl-2,3,4,5-tetrahydro-1H-benzazepin-7-yl)ethanone prepared in Preparative Example 7.

$^1$H-NMR(400 MHz, CDCl$_3$) δ:

1.32(t, J=7.2 Hz, 3H), 1.39(s, 6H), 1.60–1.66(m, 2H), 1.75–1.85(m, 2H), 2.58(d, J=1.2 Hz, 3H), 2.85–2.94(m, 5H), 4.21(q, J=7.2 Hz, 2H), 6.10(q, J=1.2 Hz, 1H), 6.91(d, J=8.8 Hz, 1H), 7.30(dd, J=2.4, 8.4 Hz, 1H), 7.47(d, J=2.4 Hz, 1H).

Preparative Example 8
(E)-3-(1,5,5-Trimethyl-2,3,4,5-tetrahydro-1H-benzazepin-7-yl)-2-butenal

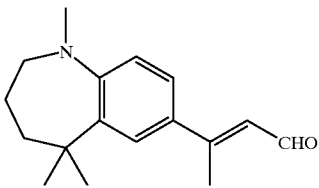

In a similar manner to that described in Steps 1 and 2 of Example 2, the title compound was prepared from ethyl (E)-3-(1,5,5-trimethyl-2,3,4,5-tetrahydro-1H-benzazepin-7-yl)-2-butenoate prepared in Example 105.

$^1$H-NMR(400 MHz, CDCl$_3$) δ:

1.38(s, 6H), 1.62–1.66(m, 2H), 1.77–1.84(m, 2H), 2.55(d, J=0.8 Hz, 3H), 2.90–2.97(m, 5H), 6.43(dq, J=1.2, 8.0 Hz, 1H), 6.93(d, J=8.4 Hz, 1H), 7.36–7.40(m, 1H), 7.56(d, J=2.4 Hz, 1H), 10.15(d, J=8.0 Hz, 1H).

Example 106
Methyl (E,E,E)-7-(1,5,5-trimethyl-2,3,4,5-tetrahydro-1H-benzazepin-7-yl)-3-methyl-octa-2,4,6-trienoate

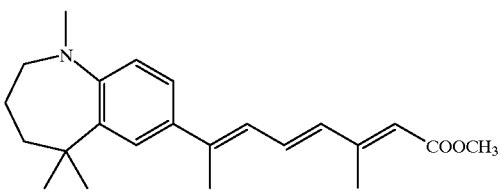

In a similar manner to that described in Step 3 of Example 2, the title compound was prepared from (E)-3-(1,5,5-trimethyl-2,3,4,5-tetrahydro-1H-benzazepin-7-yl)-2-butenal prepared in Preparative Example 8.

$^1$H-NMR (400 MHz, CDCl$_3$) δ:

1.40(s, 6H), 1.60–1.65(m, 2H), 1.26–1.84(m, 2H), 2.24(d, J=1.2 Hz, 3H), 2.39(d, J=0.8 Hz, 3H), 2.87–2.90(m, 5H), 3.72(s, 3H), 5.80(s, 1H), 6.36(d, J=14.8 Hz, 1H), 6.54(bd, J=10.8 Hz, 1H), 6.92(d, J=8.8 Hz, 1H), 7.05(dd, J=15.2, 11.2 Hz, 1H), 7.25–7.29(m, 1H), 7.46(d, J=2.4 Hz, 1H).

Example 107
(E,E,E)-7-(1,5,5-Trimethyl-2,3,4,5-tetrahydro-1H-benzazepin-7-yl)-3-methyl-octa-2,4,6-trienoic acid

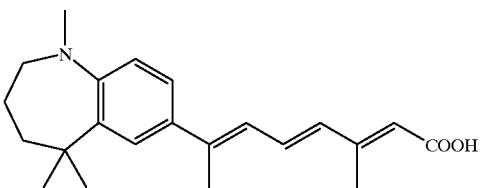

In a similar manner to that described in Step 4 of Example 2, the title compound was prepared from methyl (E,E,E)-7-(1,5,5-trimethyl-2,3,4,5-tetrahydro-1H-benzazepin-7-yl)-3-methyl-octa-2,4,6-trienoate prepared in Example 106.

$^1$H-NMR(400 MHz, CDCl$_3$) δ:

1.41(s, 6H), 1.60–1.67(m, 2H), 1.75–1.85(m, 2H), 2.26 (bs, 3H), 2.40(bs, 3H), 2.85–2.95(m, 5H), 5.82(s, 1H), 6.39(d, J=15.2 Hz, 1H), 6.56(bd, 11.2 Hz, 1H), 6.92(d, J=8.4 Hz, 1H), 7.10(dd, J=11.2, 15.2 Hz, 1H), 7.29(dd, J=2.0, 8.4 Hz, 1H), 7.47(d, J=2.0 Hz, 1H).

Preparative Example 9
(E/Z)-3-[1-(1-Methylethyl)-1,2,3,4-tetrahydroquinolin-6-yl]cinnamaldehyde

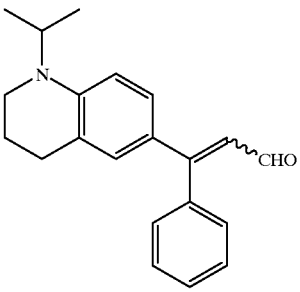

The same procedure as that described in Example 1 and Steps 1 and 2 of Example 2 was repeated except that phenyl Grignard reagent (phenylmagnesium bromide) was used in Step 3 of Example 1 instead of the methyl Grignard reagent (methylmagnesium bromide). The title compound was obtained as an isomer mixture (isomers ① and ②).

$^1$H-NMR(400 MHz, CDCl$_3$) δ:

1.20(d, J=6.8 Hz, 6H, (①)), 1.23(d, J=6.8 Hz, 6H, (②)), 1.84–1.94(m, 2H, (①+②), 2.68(t. J=6.4 Hz, 2H, ①), 2.69–2.78(m, 2H, (②)), 3.23(t, J=6.0 Hz, 2H, ①), 3.24–3.27(m, 2H, (②)), 4.11–4.21(m, 1H, ①+②), 6.55(d, J=8.4 Hz, 1H, (①)), 6.60(d, J=9.6 Hz, 1H, (②)), 7.01–7.07(m, 2H, ①+②), 7.30–7.32(m, 2H, (①+②)), 7.41–7.44 (m, 4H, ①+②), 9.31(d, J=8.4 Hz, 1H, ①), 9.62 (d, J=8.0 Hz, 1H, ②).

(identified based on the $^1$H-NMR peaks assignable to the isomer ① or ②)

Example 108

(E,E,E/Z)-7-[1-(1-Methylethyl)-1,2,3,4-tetrahydroquinolin-6-yl]-7-phenyl-3-methyl-hepta-2,4,6-trienoic acid

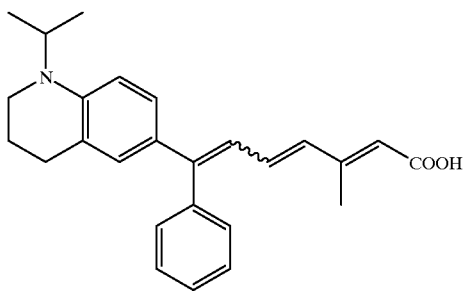

(E/Z)-3-[1-(1-Methylethyl)-1,2,3,4-tetrahydroquinolin-6-yl)cinnamaldehyde prepared in Preparative Example 9 was treated in a similar manner to that described in Steps 3 and 4 of Example 2 to give the title compound as an isomer mixture (isomers ① and ②).

$^1$H-NMR(400 MHz, CDCl$_3$) δ:

1.18(d, J=6.8 Hz, 6H, ①), 1.23(d, J=6.8 Hz, 6H, 1.84–1.98(m, 2H, ①+②), 2.13(bs, 3H, ①, 2.26(bs, 3H, ②), 2.62–2.78(m, 2H, ①+②), 3.16–3.25(m, 2H, ①+②), 4.06–4.20(m, 1H, ①+②), 5.75(s, 1H, ①), 5.80(s, 1H, ②), 6.36–6.39(m, 1H, ①+②), 6.57–6.59 (m, 1H, ①+②), 6.62–6.68(m, 5H, ①+②), 6.92–7.00 (m, 4H, ①+②).

(identified based on the $^1$H-NMR peaks assignable to the isomer ① or ②)

Preparative Example 10

1-(1-Methylethyl)-2-methyl-indoline-5-carbaldehyde

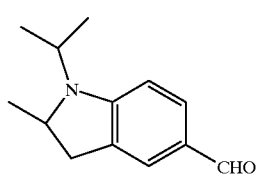

The title compound was prepared from 1-(1-methylethyl)-2-methyl-indoline in a similar manner to that described in Step 2 of Example 1.

$^1$H-NMR(400 MHz, CDCl$_3$) δ:

1.28(d, J=6.4 Hz, 3H), 1.29(d, J=6.8 Hz, 3H), 1.35(d, J=7.2 Hz, 3H), 2.59(dd, J=5.2, 16.0 Hz, 1H), 3.25(dd, J=10.0, 16.4 Hz, 1H9, 3.77(hept., J=6.8 Hz, 1H), 4.05–4.10(m, 1H), 6.37(d, J=8.4 Hz, 1H), 7.50–7.52(m, 2H), 9.61(s, 1H).

Preparative Example 11

(E)-3-[1-(1-Methylethyl)-2-methyl-indol-5-yl]-2-fluoro-2-butenal

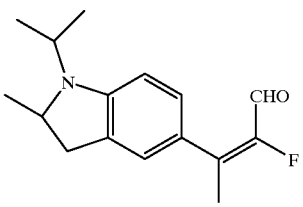

The title compound was prepared from 1-(1-methylethyl)-2-methylindole in a similar manner to that described in Steps 1 to 4 of Example 1 and Steps 1 to 3 of Example 5.

$^1$H-NMR(400 MHz, CDCl$_3$) δ:

1.63(d, J=7.2 Hz, 6H), 2.34(d, J=4.0 Hz, 3H), 2.46(d, J=0.8 Hz, 3H), 4.68(hept., J=6.8 Hz, 1H), 6.24(q, J=0.8 Hz, 1H), 7.04(dd, J=1.6, 8.4 Hz, 1H), 7.45–7.49(m, 2H), 9.32(d, J=19.6 Hz, 1H).

Example 109

Methyl (E,E,E)-7-[1-(1-methylethyl)-2-methyl-indol-5-yl]-6-fluoro-3-methyl-octa-2,4,6-trienoate

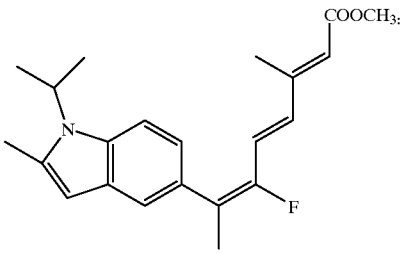

In a similar manner to that described in Step 3 of Example 2, the title compound was prepared from (E)-3-[1-(1-methylethyl)-2-methyl-indol-5-yl]-2-fluoro-2-butenal prepared in Preparative Example 11.

$^1$H-NMR(400 MHz, CDCl$_3$) δ:

1.63(d, J=7.2 Hz, 6H), 2.13(s, 3H), 2.20(d, J=4.0 Hz, 3H), 2.46(s, 3H), 3.69(s, 3H), 4.67(hept., J=7.2 Hz, 1H), 5.84 (s, 1H), 6.21(s, 1H), 6.52(d, J=15.2 Hz, 1H), 6.63(dd, J=16.0, 25.6 Hz, 1H), 6.98(dd, J=1.6, 8.4 Hz, 1H), 7.38(d, J=1.6 Hz, 1H), 7.44(d, J=8.8 Hz, 1H).

Example 110

(E,E,E)-7-[1-(1-Methylethyl)-2-methyl-indol-5-yl]-6-fluoro-3-methyl-octa-2,4,6-trienoic acid

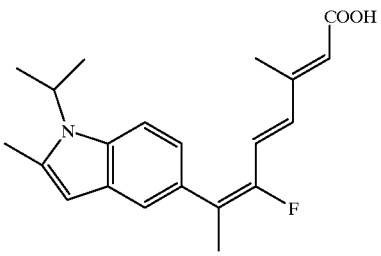

In a similar manner to that described in Step 4 of Example 2, the title compound was prepared from methyl (E,E,E)-7-[1-(1-methylethyl)-2-methyl-indol-5-yl]-6-fluoro-3-methyl-octa-2,4,6-trienoate prepared in Example 109.

¹H-NMR(400 MHz, CDCl₃) δ:
1.63(d, J=7.2 Hz, 6H), 2.14(s, 3H), 2.21(d, J=3.2 Hz, 3H), 2.46(s, 3H), 4.66(hept., J=7.2 Hz, 1H), 5.86(bs, 1H), 6.21(bs, 1H), 6.55(d, J=15.6 Hz, 1H), 6.66(dd, J=15.6, 25.6 Hz, 1H), 6.97–7.00(m, 1H), 7.38–7.46(m, 2H).

Preparative Example 12
1-(1-Methylethyl)-2,3-dimethyl-indoline-5-carbaldehyde

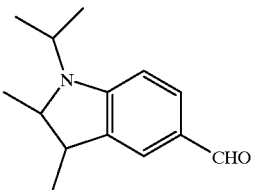

The title compound was prepared from 1-(1-methylethyl)-2,3-dimethyl-indoline in a similar manner to that described in Step 2 of Example 1.
¹H-NMR(400 MHz, CDCl₃) δ:
1.10(d, J=6.4 Hz, 3H), 1.26(d, J=6.8 Hz, 3H), 1.29(d, J=6.8 Hz, 3H), 1.38(d, J=6.8 Hz, 3H), 3.37(hept., J=7.2 Hz, 1H), 3.75–3.82(m, 1H), 4.00–4.07(m, 1H), 6.37(d, J=8.4 Hz, 1H), 7.48–7.52(m, 2H), 9.62(s, 1H).

Preparative Example 13
1-[1-(1-Methylethyl)-2,3-dimethyl-indol-5-yl]ethanone

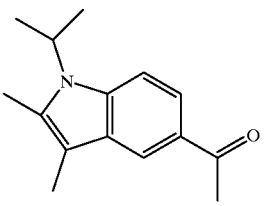

In a similar manner to that described in Steps 3 and 4 of Example 1, the title compound was prepared from 1-(1-methylethyl)-2,3-dimethyl-indoline-5-carbaldehyde prepared in Preparative Example 12.
¹H-NMR(400 MHz, CDCl₃) δ:
1.61(d, J=7.2 Hz, 6H) 2.28(s, 3H), 2.38(s, 3H), 2.67(s, 3H), 4.67(hept., J=6.8 Hz, 1H), 7.43(d, J=8.8 Hz, 1H), 7.77(dd, J=2.0, 8.8 Hz, 1H), 8.16(d, J=2.0 Hz, 1H).

Example 111
Ethyl (E)-3-[1-(1-methylethyl)-2,3-dimethyl-indol-5-yl]-2-fluoro-2-butenoate

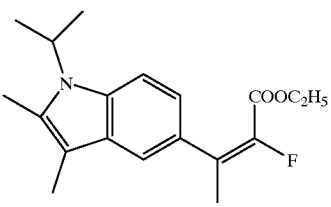

In a similar manner to that described in Step 1 of Example 5, the title compound was prepared from 1-[1-(1-methylethyl)-2,3-dimethyl-indol-5-yl]ethanone prepared in Preparative Example 13.
¹H-NMR(400 MHz, CDCl₃) δ:
1.00(t, J=6.8 Hz, 3H), 1.59(d, J=6.8 Hz, 6H), 2.21(s, 6H), 2.35(s, 3H), 4.05(q, J=7.2 Hz, 2H), 4.64(hept., J=6.8 Hz, 1H), 6.92(dd, J=1.6, 8.4 Hz, 1H), 7.25–7.29(m, 1H), 7.37(d, J=8.4 Hz, 1H).

Preparative Example 14

(E)-3-[1-(1-Methylethyl)-2,3-dimethylindol-5-yl]-2-fluoro-2-butenal

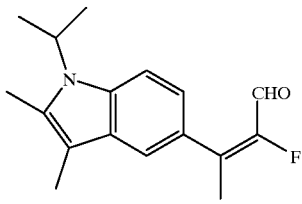

In a similar manner to that described in Steps 1 and 2 of Example 2, the title compound was prepared from ethyl (E)-3-[1-(1-methylethyl)-2,3-dimethyl-indol-5-yl]-2-fluoro-2-butenoate prepared in Example 111.

¹H-NMR(400 MHz, CDCl₃) δ:
1.61(d, J=6.8 Hz, 6H), 2.23(s, 3H), 2.36(s, 3H), 2.37(s, 3H), 4.67(hept., J=6.8 Hz, 1H), 7.04(dd, J=2.0, 8.4 Hz, 1H), 7.41–7.46(m, 2H), 9.32(d, J=19.6 Hz, 1H).

Example 112

Methyl (E,E,E)-7-[1-(1-methylethyl)-2,3-dimethyl-indol-5-yl]-6-fluoro-3-methyl-octa-2,4,6-trienoate

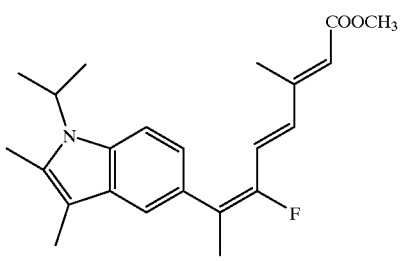

In a similar manner to that described in Step 3 of Example 2, the title compound was prepared from (E)-3-[1-(1-methylethyl)-2,3-dimethyl-indol-5-yl]-2-fluoro-2-butenal prepared in Preparative Example 14.

¹H-NMR(400 MHz, CDCl₃) δ:
1.62(d, J=7.2 Hz, 6H), 2.13(s, 3H), 2.22(s, 6H), 2.38(s, 3H), 3.69(s, 3H), 4.66(hept., J=7.2 Hz, 1H), 5.84(s, 1H), 6.53(d, J=15.6 Hz, 1H), 6.66(dd, J=15.6, 26.4 Hz, 1H), 6.98(dd, J=1.6, 8.4 Hz, 1H), 7.35(d, J=2.0Hz, 1H), 7.41(d, J=8.4 Hz, 1H).

Example 113
(E,E,E)-7-[1-(1-Methylethyl)-2,3-dimethyl-indol-5-yl]-6-fluoro-3-methyl-octa-2,4,6-trienoic acid

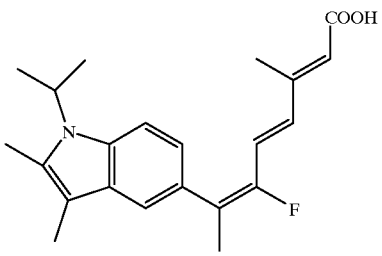

In a similar manner to that described in Step 4 of Example 2, the title compound was prepared from methyl (E,E,E)-7-[1-(1-methylethyl)-2,3-dimethyl-indol-5-yl]-6-fluoro-3-methyl-octa-2 4,6-trienoate prepared in Example 112.
$^1$H-NMR(400 MHz, CDCl$_3$) δ:
1.62(d, J=7.2 Hz, 6H), 2.14(s, 3H), 2.22(s, 6H), 2.38(s, 3H), 4.66(hept., J=7.2 Hz, 1H), 5.86(s, 1H), 6.56(d, J=15.6 Hz, 1H), 6.70(dd, J=15.6, 26.0 Hz, 1H), 6.99 (dd, J=1.6, 8.4 Hz, 1H), 7.35(d, J=1.6 Hz, 1H), 7.42(d, J=8.4 Hz, 1H).

Preparative Example 15
1,2,3-Trimethyl-indole-5-carbaldehyde

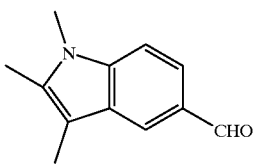

1,2,3-Trimethylindoline (21.5 g) was formylated in a similar manner to that described in Step 2 of Example 1 to obtain 20.1 g of 1,2,3-trimethylindoline-5-carbaldehyde. The obtained aldehyde (7.5 g) was dissolved in 200 ml of 1,4-dioxane, followed by the addition of 18 g of DDQ. The obtained mixture was heated under reflux for 2.5 hours, followed by the addition of 100 ml of toluene. Insolubles were filtered out and the organic phase was concentrated in a vacuum. The obtained residue was purified by flash column chromatography to give 900 mg of the title compound.
$^1$H-NMR(400 MHz, CDCL$_3$) δ:
2.29(s, 3H), 2.37(s, 3H), 3.69(s, 3H), 7.30(d, J=8.4 Hz, 1H), 7.71(dd, J=0.8, 8.4 Hz, 1H), 8.03(d, J=0.8 Hz, 1H), 10.02(s, 1H).

Preparative Example 16
1-(1,2,3-Trimethyl-indol-5-yl)ethanone

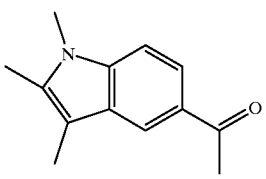

In a similar manner to that described in Steps 3 and 4 of Example 1, the title compound was prepared from 1,2,3-trimethyl-indole-5-carbaldehyde prepared in Preparative Example 15.
$^1$H-NMR(400 MHz, CDCl$_3$) δ:
2.29(s, 3H), 2.36(s, 3H), 2.67(s, 3H), 3.67(s, 3H), 7.23(d, J=8.8 Hz, 1H), 7.82(dd, J=1.6, 8.8 Hz, 1H), 8.16(d, J=1.6 Hz, 1H).

Preparative Example 17
(E)-3-(1,2,3-Trimethyl-indol-5-yl)-2-butenal

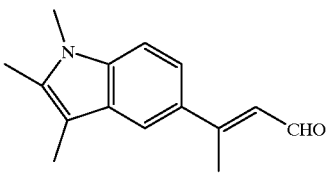

In a similar manner to that described in Step 5 of Example 1 and Steps 1 and 2 of Example 2, the title compound was prepared from 1-(1,2,3-trimethyl-indol-5-yl)ethanone prepared in Preparative Example 16.
$^1$H-NMR(400 MHz, CDCl$_3$) δ:
2.27(s, 3H), 2.36(s, 3H), 2.67(d, J=1.2 Hz, 3H), 3.66(s, 3H), 6.54(dq, J=1.2, 8.0 Hz, 1H), 7.23(d, J=8.4 Hz, 1H), 7.41(dd, J=2.0, 8.8 Hz, 1H), 7.74(d, J=1.6 Hz, 1H), 10.18(d, J=8.4 Hz, 1H).

Example 114
Methyl (E,E,E)-7-(1,2,3-trimethyl-indol-5-yl)-3-methyl-octa-2,4,6-trienoate

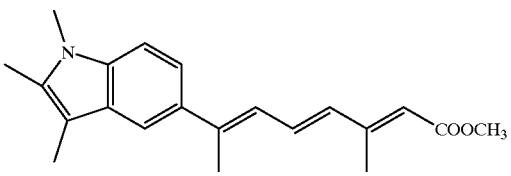

In a similar manner to that described in Step 3 of Example 2, the title compound was prepared from (E)-3-(1,2,3-trimethyl-indol-5-yl)-2-butenal prepared in Preparative Example 17.
$^1$H-NMR(400 MHz, CDCl$_3$) δ:
2.27(s, 3H), 2.34(s, 3H), 2.36(d, J=1.2 Hz, 3H), 2.41(d, J=0.8 Hz, 3H), 3.65(s, 3H), 3.72(s, 3H), 5.80(s, 1H), 6.39(d, J=14.8 Hz, 1H), 6.65(dd, J=2.0, 11.2 Hz, 1H), 7.11(dd, J=11.2, 14.8 Hz, 1H), 7.19(d, J=8.8 Hz, 1H), 7.33(dd, J=2.0, 8.8 Hz, 1H), 7.59(d, J=1.2 Hz, 1H).

Example 115
(E,E,E)-7-(1,2,3-Trimethyl-indol-5-yl)-3-methyl-octa-2,4,6-trienoic acid

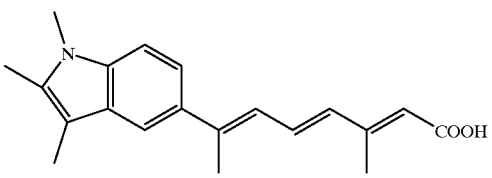

In a similar manner to that described in Step 4 of Example 2, the title compound was prepared from methyl (E,E,E)-7-(1,2,3-trimethyl-indol-5-yl)-3-methyl-octa-2,4,6-trienoate prepared in Example 114.
$^1$H-NMR(400 MHz, CDCl$_3$) δ:

2.27(s, 3H), 2.35(s, 3H), 2.37(s, 3H), 2.42(s, 3H), 3.65(s, 3H), 5.83(bs, 1H), 6.41(d, J=14.8 Hz, 1H), 6.67(bd, J=11.2 Hz, 1H), 7.10–7.20(m, 2H), 7.34(dd, J=1.6, 8.4 Hz, 1H), 7.60(d, J=1.2 Hz, 1H).

Preparative Example 17
1,2,3,3-Tetramethyl-indoline-5-carbaldehyde

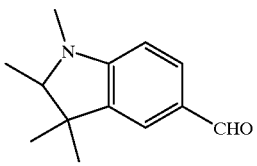

The title compound was prepared from 1,2,3,3-tetramethyl-indoline in a similar manner to that described in Step 2 of Example 1.
$^1$H-NMR(400 MHz, CDCl$_3$) δ:
  1.06(s, 3H), 1.18(d, J=6.4 Hz, 3H), 1.29(s, 3H), 2.81(s, 3H), 3.22(a, J=6.4 Hz, 1H), 6.42(d, J=8.0 Hz, 1H), 7.53–7.58(m, 2H), 9.68(s, 1H).

Preparative Example 18
1-(1,2,3,4-Tetramethyl-indolin-5-yl)ethanone

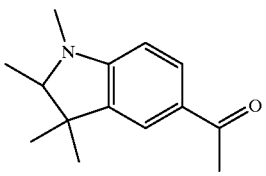

In a similar manner to that described in Steps 3 and 4 of Example 1, the title compound was prepared from 1, 2,3,3-tetramethyl-indoline-5-carbaldehyde prepared in Preparative Example 17.
$^1$H-NMR(400 MHz, CDCl$_3$) δ:
  1.05(s, 3H), 1.19(d, J=6.4 Hz, 3H), 1.30(s, 3H), 2.51(s, 3H), 2.79(s, 3H), 3.14(q, J=6.4 Hz, 1H), 6.39(d, J=8.0Hz, 1H), 7.65(d, J=1.6 Hz, 1H), 7.76(dd, J=1.6, 8.0 Hz, 1H).

Example 116
Ethyl (E)-3-(1,2,3,3-tetramethyl-indolin-5-yl)-2-butenoate

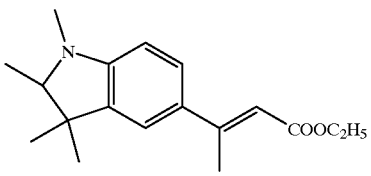

In a similar manner to that described in Step 5 of Example 1, the title compound was prepared from 1-(1,2,3,4-tetramethyl-indolin-5-yl)ethanone prepared in Preparative Example 18.
$^1$H-NMR(400 MHz, CDCl$_3$) δ:
  1.03(s, 3H), 1.19(d, J=6.4 Hz, 3H), 1.30(s, 3H), 1.32(t, J=7.2 Hz, 3H), 2.57(d, J=8.0 Hz, 3H), 2.73(s, 3H), 2.99(q, J=6.4 Hz, 1H), 4.20(q, J=7.2 Hz, 2H), 6.10(q, J=1.0 Hz, 1H), 6.45(d, J=8.4 Hz, 1H), 7.20(d, J=2.0 Hz, 1H), 7.31(dd, J=2.0, 8.4 Hz, 1H).

Preparative Example 19
(E)-3-(1,2,3,3-Tetramethyl-indolin-5-yl)-2-butenal

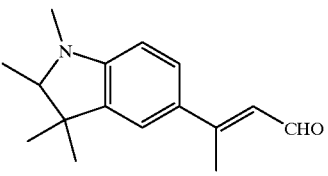

In a similar manner to that described in Steps 1 and 2 of Example 2, the title compound was prepared from ethyl (E)-3-(1,2,3,3-tetramethyl-indolin-5-yl)-2-butenoate prepared in Example 116. $^1$H-NMR(400 MHz, CDCl$_3$) δ:
  1.04(s, 3H), 1.19(d, J=6.4 Hz, 3H), 1.30(s, 3H), 2.53(d, J=0.8 Hz, 3H), 2.76(s, 3H), 3.07(q, J=6.4 Hz, 1H), 6.43(dq, J=1.0, 8.4 Hz, 1H), 6.46(d, J=8.0 Hz, 1H), 7.28(d, J=2.0 Hz, 1H), 7.41(dd, J=2.0, 8.4 Hz, 1H), 10.12(d, J=8.4 Hz, 1H).

Example 117
Methyl (E,E,E)-7-(1,2,3,3-tetramethyl-indolin-5-yl)-3-methyl-octa-2,4,6-trienoate

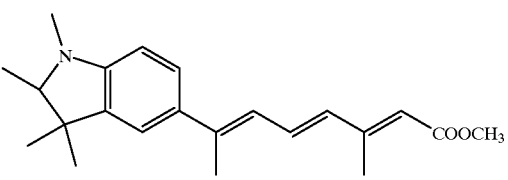

In a similar manner to that described in Step 3 of Example 2, the title compound was prepared from (E)-3-(1,2,3,3-tetramethyl-indolin-5-yl)-2-butenal prepared in Preparative Example 19.
$^1$H-NMR(400 MHz, CDCl$_3$) δ:
  1.04(s, 3H), 1.19(d, J=6.4 Hz, 3H), 1.31(s, 3H), 2.23(d, J=1.2 Hz, 3H), 2.39(d, J=1.2 Hz, 3H), 2.72(s, 3H), 2.94(q, J=6.4 Hz, 1H), 3.71(s, 3H), 5.78(bs, 1H), 6.35 (d, J=14.8 Hz, 1H), 6.46(d, J=8.0Hz, 1H), 6.54(d, J=10.4 Hz, 1H), 7.06(dd, J=11.6, 15.6 Hz, 1H), 7.19(d, J=2.0 Hz, 1H), 7.26(dd, J=2.0, 8.0 Hz, 1H).

Example 118
(E,E,E)-7-(1,2,3,3-Tetramethyl-indolin-5-yl)-3-methyl-octa-2,4,6-trienoic acid

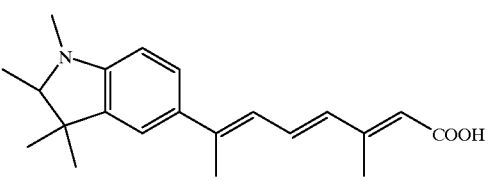

In a similar manner to that described in Step 4 of Example 2, the title compound was prepared from methyl (E,E,E)-7-(1,2,3,3-tetramethyl-indolin-5-yl)-3-methyl-octa-2,4,6-trienoate prepared in Example 117.
$^1$H-NMR(400 MHz, CDCl$_3$) δ:
  1.04(s, 3H), 1.19(d, J=6.4 Hz, 3H), 1.31(s, 3H), 2.24(s, 3H), 2.40(d, J=1.2 Hz, 3H), 2.73(s, 3H), 2.95(q, J=6.4 Hz, 1H), 5.81(s, 1H), 6.38(d, J=15.2 Hz, 1H), 6.47(d, J=8.4 Hz, 1H), 6.56(bd, J=10.8 Hz, 1H), 7.07–7.14(m, 1H), 7.19(d, J=1.6 Hz, 1H), 7.25–7.29(m, 1H).

Example 119
Ethyl (E)-3-(1,2,3,4-tetramethyl-indolin-5-yl)-2-fluoro-2-butenoate

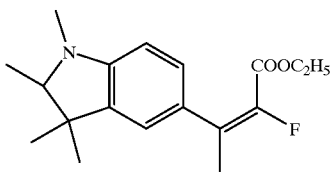

In a similar manner to that described in Step 1 of Example 5, the title compound was prepared from 1-(1,2,3,4-tetramethyl-indolin-5-yl)ethanone prepared in Preparative Example 18.

$^1$H-NMR(400 MHz, CDCl$_3$) δ:
1.01(s, 3H), 1.04(t, J=7.2 Hz, 3H), 1.18(d, J=6.8 Hz, 3H), 1.26(s, 3H), 2.13(d, J=4.8 Hz, 3H), 2.70(s, 3H), 2.92(q, J=6.8 Hz, 1H), 4.02–4.08(m, 2H), 6.44(d, J=8.0 Hz, 1H), 6.82(d, J=2.0 Hz, 1H), 6.92(dd, J=2.0, 8.0 Hz, 1H).

Preparative Example 20
(E)-3-(1,2,3,3-Tetramethyl-indolin-5-yl)-2-fluoro-2-butenal

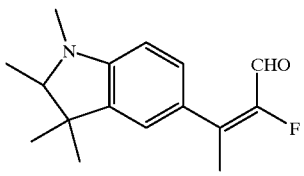

In a similar manner to that described in Steps 1 and 2 of Example 2, the title compound was prepared from ethyl (E)-3-(1,2,3,4-tetramethyl-indolin-5-yl)-2-fluoro-2-butenoate prepared in Example 119.

$^1$H-NMR(400 MHz, CDCl$_3$) δ:
1.04(s, 3H), 1.20(d, J=6.8 Hz, 3H), 1.29(s, 3H), 2.27(d, J=4.0 Hz, 3H), 2.74(s, 3H), 3.03(q, J=6.8 Hz, 1H), 6.45(d, J=8.0 Hz, 1H), 6.94(d, J=1.6 Hz, 1H), 7.05(dd, J=2.0, 8.0 Hz, 1H), 9.30(d, J=19.6 Hz, 1H).

Example 120
Methyl (E,E,E)-7-(1,2,3,4-tetramethyl-indolin-5-yl)-6-fluoro-3-methyl-octa-2,4,6-trienoate

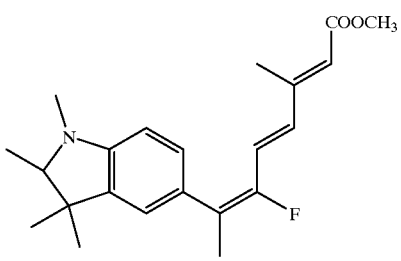

In a similar manner to that described in Step 3 of Example 2, the title compound was prepared from (E)-3-(1,2,3,3-tetramethyl-indolin-5-yl)-2-fluoro-2-butenal prepared in Preparative Example 20.

$^1$H-NMR(400 MHz, CDCl$_3$) δ:
1.03(s, 3H), 1.20(d, J=6.4 Hz, 3H), 1.28(s, 3H), 2.14(d, J=3.6 Hz, 3H), 2.18(d, J=1.2 Hz, 3H), 2.73(s, 3H), 2.96(q, J=6.4 Hz, 1H), 3.70(s, 3H), 5.84(s, 1H), 6.48(d, J=8.0 Hz, 1H), 6.50(d, J=13.6 Hz, 1H), 6.62(dd, J=16.0, 26.0 Hz, 1H), 6.89(d, J=2.0Hz, 1H), 7.00(dd, J=2.0, 8.0 Hz, 1H).

Example 121
(E,E,E)-7-(1,2,3,3-Tetramethyl-indolin-5-yl)-6-fluoro-3-methyl-octa-2,4,6-trienoic acid

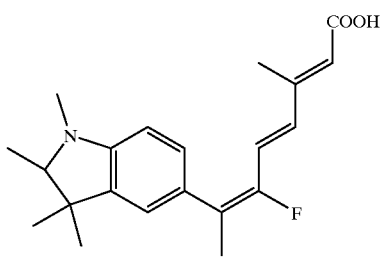

In a similar manner to that described in Step 4 of Example 2, the title compound was prepared from methyl (E,E,E)-7-(1,2,3,4-tetramethyl-indolin-5-yl)-6-fluoro-3-methyl-octa-2,4,6-trienoate prepared in Example 120.

$^1$H-NMR(400 MHz, CDCl$_3$) δ:
1.03(s, 3H), 1.20(d, J=6.4 Hz, 3H), 1.29(s, 3H), 2.15(bs, 3H), 2.19(s, 3H), 2.73(s, 3H), 2.92–3.00(m, 1H), 5.87 (s, 1H), 6.48(d, J=8.0 Hz, 1H), 6.53(d, J=15.2 Hz, 1H), 6.66(dd, J=15.6, 26.0 Hz, 1H), 6.89(bs, 1H), 7.00(bd, J=8.4 Hz, 1H).

Preparative Example 21
(E)-3-(2-Methoxy-6-isopropoxy-4-pyridyl)-2-butenal

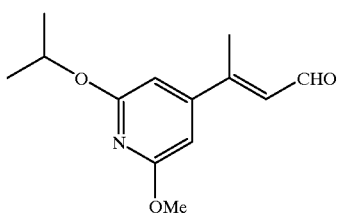

2-Hydroxy-6-methoxy-4-carbomethoxy-pyridine was isopropylated into 2-methoxy-6-isopropoxy-4-carbomethoxy-pyridine in a similar manner to that described in Step 1 of Example 1. The pyridine derivative thus obtained was converted into an aldehyde in a similar manner to that described in Step 2 of Example 1. This aldehyde was treated in a similar manner to that described in Steps 3 to 5 of Example 1 and Steps 1 and 2 of Example 2 to give the title compound.

$^1$H-NMR(CDCl$_3$, 400 MHz) δ:
1.36(d, J=6.2 Hz, 6H), 2.48(s, 3H), 3.91(s, 3H), 5.26 (Hept., J=6.2 Hz, 1H), 6.27–6.35(m, 3H), 10.14–10.19 (m, 1H).

Example 122
(E,E,E)-7-(2-Methoxy-6-isopropoxy-4-pyridyl)-3-methyl-octa-2,4,6-trienoic acid

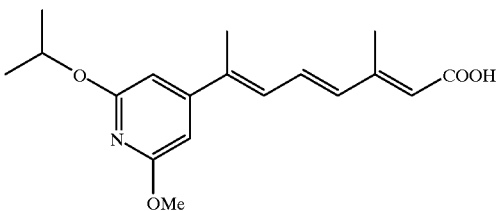

In a similar manner to that described in Steps 3 and 4 of Example 2, the title compound was prepared from (E)-3-(2-methoxy-6-isopropoxy-4-pyridyl)-2-butenal prepared in Preparative Example 21.

$^1$H-NMR(CDCl$_3$, 400 MHz) δ:

1.35(d, 6H, J=6.2 Hz), 2.18(s, 3H), 2.38(s, 3H), 3.90(s, 3H), 5.26(hept., J=6.21 Hz, 1H), S.86(s, 1H), 6.34(s, 2H), 6.42(d, J=15.2 Hz, 1H), 6.62–6.67(m, 1H), 7.01 (dd, J=11.2, 15.2 Hz, 1H).

pale-yellow solid

Preparative Example 22
5,8-Dimethyl-2-(2-furyl)-5,6,7,8-tetrahydroquinoline

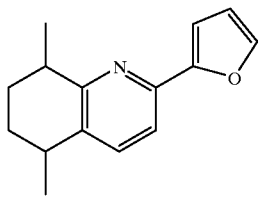

The title compound was prepared according to the method of F. Krohnke et al. (Synthesis, 1976, 1–24).

$^1$H-NMR(400 MHz, CDCl$_3$)

1.27, 1.29(2×d, J=7.0 Hz, 3H), 1.38, 1.40(2×d, J=7.0 Hz, 3H), 1.43–1.76(m, 2H), 1.83–2.08(m, 2H), 2.85–3.04 (m, 2H), 6.49(s, 1H), 6.98(s, 1H), 7.40–7.51(m, 2H).

Preparative Example 23
5,8-Dimethyl-2-carbomethoxy-5,6,7,8-tetrahydroquinoline

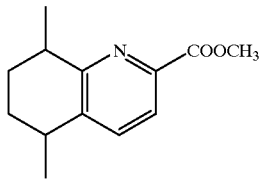

5,8-Dimethyl-2-(2-furyl)-5,6,7,8-tetrahydroquinoline (3 g) was dissolved in 100 ml of methanol. Ozone generated from oxygen at −78° C. was introduced into the obtained solution for 10 minutes. The resulting system was saturated with nitrogen gas, followed by the addition of 7 ml of dimethyl sulfide. The temperature of the mixture was raised to room temperature and the resulting reaction mixture was concentrated to give about 3 g of a crude product. This crude product containing a carboxylic acid was dissolved in 10 ml of DMF, followed by the addition of 1 ml of methyl iodide and 3.6 g of K$_2$CO$_3$. The obtained mixture was stirred at room temperature for one hour, followed by the addition of 30 ml of water. The obtained mixture was extracted with ethyl acetate (50 ml×2) and the organic phase was washed with a saturated aqueous solution of common salt, dried over MgSO$_4$ and concentrated. The obtained mixture was purified by column chromatography to give 1.6 g of the objective compound.

$^1$H-NMR(400 MHz, CDCl$_3$)

1.28, 1.30(2×d, J=7.0 Hz, 3H), 1.36, 1.40(2×d, J=7.0 Hz, 3H), 1.42–1.79(m, 2H), 1.84–2.18(m, 2H), 2.91–3.16 (m, 2H), 3.97(s, 3H), 7.57, 7.59(2×d, J=7.5 Hz, 1H), 7.88, 7.89(2×d, J=7.5 Hz, 1H).

Preparative Example 24
5,8-Dimethyl-5,6,7,8-tetrahydroquinoline-2-carbaldehyde

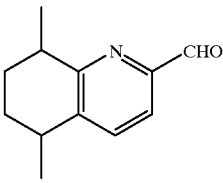

In a similar manner to that described in Steps 1 and 2 of Example 2, the title compound was prepared from 5,8-dimethyl-2-carbomethoxy-5,6,7,8-tetrahydroquinoline prepared in Preparative Example 23.

$^1$H-NMR(400 MHz, CDCl$_3$)

1.31, 1.33(2×d, J=7.1 Hz, 3H), 1.40, 1.44(2×d, J=7.1 Hz, 3H), 1.45–1.79(m, 2H), 1.86–2.20(m, 2H), 2.94–3.12 (m, 2H), 7.64(d, J=7.9 Hz, 1H), 7.73(d, J=7.9 Hz, 1H).

Example 123
Ethyl (E)-3-(5,8-dimethyl-5,6,7,8-tetrahydroquinolin-2-yl)-2-butenoate

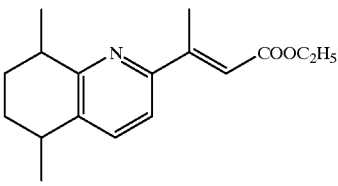

In a similar manner to that described in Steps 3 to 5 of Example 1, the title compound was prepared from 5,8-dimethyl-5,6,7,8-tetrahydroauinoline-2-carbaldehyde prepared in Preparative Example 24.

$^1$H-NMR(400 MHz, CDCl$_3$)

1.27, 1.28(2×d, J=7.6 Hz, 3H), 1.32(t, J=7.0 Hz, 3H), 1.42–1.75(m, 2H), 1.83–2.16(m, 2H), 2.60(s, 3H), 2.88–3.01(m, 2H), 4.22(q, J=7.0 Hz, 2H), 6.74(s, 1H), 7.31(d, J=7.7 Hz, 1H), 7.47, 7.49(2×d, J=7.7 Hz, 1H).

Example 124
Methyl (E,E,E)-7-(5,8-dimethyl-5,6,7,8-tetrahydroquinolin-2-yl)-3-methyl-octa-2,4,6-trienoate

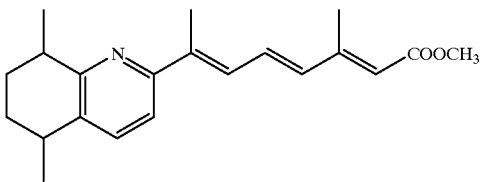

In a similar manner to that described in Steps 1 to 3 of Example 2, the title compound was prepared from ethyl (E)-3-(5,8-dimethyl-5,6,7,8-tetrahydroquinolin-2-yl)-2-butenoate prepared in Example 123.
$^1$H-NMR(400 MHz, CDCl$_3$)
1.27, 1.28(2×d, J=6.8 Hz, 3H), 1.39, 1.42(2×d, J=6.8 Hz, 3H), 1.42–1.75(m, 2H), 1.84–2.15(m, 2H), 2.29(s, 3H), 2.39(s, 3H), 2.86–3.01(m, 2H), 3.72(s, 3H), 5.83(s, 1H), 6.48(d, J=15.6 Hz, 1H), 7.08(dd, J=11.6, 15.0 Hz, 1H), 7.21(d, J=11.6 Hz, 1H), 7.25(d, J=8.0 Hz, 1H), 7.43, 7.45(2×d, J=8.0 Hz, 1H).

Example 125
(E,E,E)-7-(5,8-Dimethyl-5,6,7,8-tetrahydroquinolin-2-yl)-3-methyl-octa-2,4,6-trienoic acid

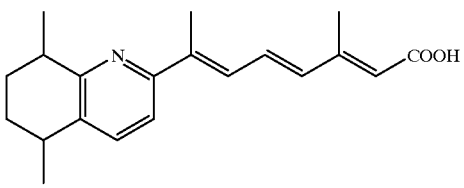

In a similar manner to that described in Step 4 of Example 2, the title compound was prepared from methyl (E,E,E)-7-(5,8-dimethyl-5,6,7,8-tetrahydroquinolin-2-yl)-3-methyl-octa-2,4,6-trienoate prepared in Example 124.
$^1$H-NMR(400 MHz, CDCl$_3$)
1.27, 1.28(2×d, J=6.8 Hz, 3H), 1.40, 1.43(2×d, J=6.8 Hz, 3H), 1.44–1.76(m, 2H), 1.84–2.16(m, 2H), 2.30(s, 3H), 2.40(s, 3H), 2.86–3.02(m, 2H), 5.86(s, 1H), 6.50(d, J=14.8 Hz, 1H), 7.11(dd, J=11.6, 14.8 Hz, 1H), 7.20–7.29(m, 2H), 7.46(m, 1H).

Preparative Example 25
5-Carbethoxy-3-(2,6-dimethylphenyl)isoxazole

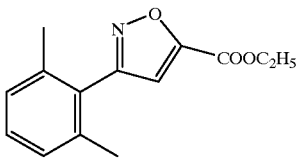

4.66 g of hydroxylamine hydrochloride and 13 g of sodium acetate were added to 70 ml of a methanolic solution of 4.5 g of 2,6-dimethylbenzaldehyde. The obtained mixture was heated at 60° C. for 4 hours and distilled to remove the solvent. Water was added to the residue, followed by the extraction with ethyl acetate. The organic phase was washed with a saturated aqueous solution of common salt, dried over magnesium sulfate and concentrated in a vacuum to give 4.8 g of a crude oxime having the following structure as a pale-yellow oil:

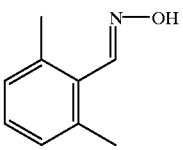

$^1$H-NMR(400 MHz, CDCl$_3$) δ:
2.41(6H, s), 7.06(d, J=8.0 Hz, 2H), 7.16(dd, J=8.0, 8.0 Hz, 1H), 7.95(bs, 1H), 8.43(s, 1H).
3.77 g of ethyl propionate and 56 ml of a 6% aqueous solution of sodium hypochlorite were added to 120 ml of 4.8 g of the above crude oxime in methylene chloride, followed by the stirring for one hour. The organic phase was washed with a saturated aqueous solution of sodium hydrogencarbonate, dried over magnesium sulfate and concentrated in a vacuum. The residue was purified by silica gel column chromatography (5% ethyl acetate/hexane) to give 6.9 g of the title compound as a pale-yellow oil.
$^1$H-NMR(400 MHz, CDCl$_3$) δ:
1.10(t, J=6.0 Hz, 3H), 2.14(s, 3H), 4.48(q, J=6.0 Hz, 2H), 6.91(s, 1H), 7.10(d, J=7.6 Hz, 1H), 7.12(d, J=7.6 Hz, 1H), 7.23(bs, 1H).

Preparative Example 26
3-(2,6-Dimethylphenyl)isoxazole-5-carbaldehyde

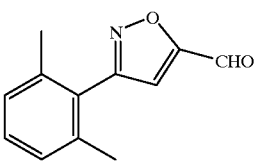

In a similar manner to that described in Steps 1 and 2 of Example 2, the title compound was prepared from 5-carbethoxy-3-(2,6-dimethylphenyl)isoxazole prepared in Preparative Example 25.
$^1$H-NMR(400 MHz, CDCl$_3$) δ:
2.28(6H, s), 6.96(1H, s), 7.15(d, J=8.4 Hz, 2H), 7.29(t, J=8.4 Hz, 1H), 10.07(1H, s).

Preparative Example 27
1-[3-(2,6-Dimethylphenyl)isoxazol-5-yl]-ethanone

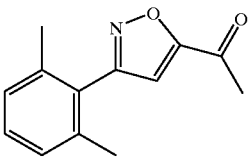

In a similar manner to that described in Steps 3 and 4 of Example 1, the title compound was prepared from 3-(2,6-dimethylphenyl)isoxazole-5-carbaldehyde prepared in Preparative Example 26.
$^1$H-NMR(400 MHz, CDCl$_3$) δ:
2.18(s, 6H), 2.70(s, 3H), 6.88(d, J=0.8 Hz, 1H), 7.14(d, J=7.4 Hz, 2H), 7.26(t, J=7.4 Hz, 1H).

Preparative Example 28

(E)-3-[3-(2,6-Dimethylphenyl)isoxazol-5-yl]-2-butenal

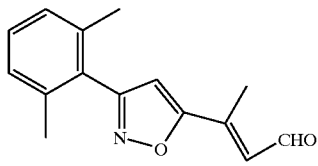

In a similar manner to that described in Step 5 of Example 1 and Steps 1 and 2 of Example 2, the title compound was prepared from 1-[3-(2,6-dimethylphenyl)-isoxazol-5-yl]-ethanone prepared in Preparative Example 27.

$^1$H-NMR(400 MHz, CDCl$_3$) δ:
2.18(s, 6H), 2.57(s, 3H), 6.55(s, 1H), 6.74(dd, J=7.6, 1.6 Hz, 1H), 7.12(d, J=7.6 Hz, 2H), 7.25(t, J=7.6 Hz, 1H), 10.22(d, J=7.6 Hz, 1H).

Example 126

(E,E,E)-7-[3-(2,6-Dimethylphenyl)isoxazol-5-yl]-3-methyl-octa-2,4,6-trienoic acid

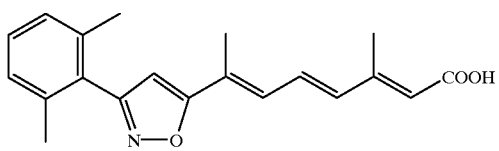

In a similar manner to that described in Steps 3 and 4 of Example 2, the title compound was prepared from (E)-3-[3-(2,6-dimethylphenyl)isoxazol-5-yl]-2-butenal prepared in Preparative Example 28.

$^1$H-NMR(400 MHz, DMSO-d$_6$) δ:
2.10(s, 6H), 2.21(s, 3H), 2.32(s, 3H), 5.88(br.s, 1H), 6.62–6.83(m, 2H), 7.04(d, J=9.6 Hz, 1H), 7.14(d, J=7.2 Hz, 2H), 7.25(t, J=7.2 Hz, 1H).

Preparative Example 29

(Z)-3-[3-(2,6-Dimethylphenyl)isoxazol-5-yl]-2-fluoro-2-butenal

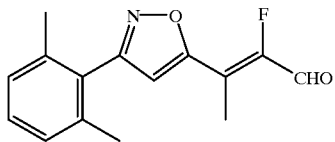

In a similar manner to that described in Steps 1 and 2 of Example 6, the title compound was prepared from 1-[3-(2,6-dimethylphenyl)isoxazol-5-yl]-ethanone prepared in Preparative Example 27.

$^1$H-NMR(400 MHz, CDCl$_3$) δ:
2.19(s, 6H), 2.62(d, J=4.0 Hz, 3H), 6.82(d, J=3.6 Hz, 1H), 7.13(d, J=8.0 Hz, 2H), 7.26(t, J=8.0 Hz, 1H), 9.96(d, J=18.0 Hz, 1H).

Example 127

(E,E,Z)-7-[3-(2,6-Dimethylphenyl)isoxazol-5-yl]-6-fluoro-3-methyl-octa-2,4,6-trienoic acid

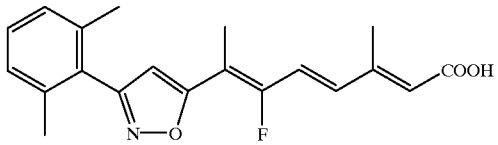

In a similar manner to that described in Steps 3 and 4 of Example 2, the title compound was prepared from (Z)-3-[3-(2,6-dimethylphenyl)isoxazol-5-yl]-2-fluoro-2-butenal prepared in Preparative Example 29.

$^1$H-NMR(400 MHz, DMSO-d$_6$) δ:
2.10(s, 6H), 2.23(s, 3H), 2.32(s, 3H), 6.07(bs, 1H), 6.79–6.90(m, 2H), 7.02(d, J=16.4 Hz, 1H), 7.15(d, J=7.2 Hz, 2H), 7.26(t, J=7.2 Hz, 1H).

Preparative Example 30

(E)-3-[3-(2,6-Dimethylphenyl)isoxazol-5-yl]-2-fluoro-2-butenal

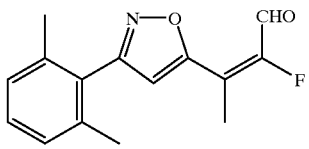

In a similar manner to that described in Steps 1 to 3 of Example 5, the title compound was prepared from 1-[3-(2,6-dimethylphenyl)isoxazol-5-yl]-ethanone prepared in Preparative Example 27.

$^1$H-NMR(400 MHz, CDCl$_3$) δ:
2.20(s, 6H), 2.33(d, J=4.0 Hz, 3H), 6.50(s, 1H), 7.14(d, J=7.2 Hz, 2H), 7.27(t, J=7.2 Hz, 1H), 10.18(d, J=20 Hz, 1H).

Example 128

(E,E,E)-7-[3-(2,6-Dimethylphenyl)isoxazol-5-yl]-6-fluoro-3-methyl-octa-2,4,6-trienoic acid

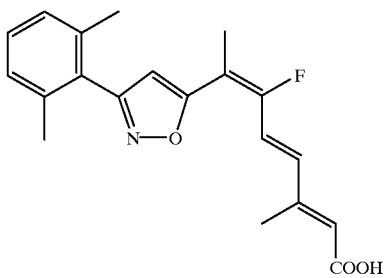

In a similar manner to that described in Steps 3 and 4 of Example 2, the title compound was prepared from (E)-3-[3-(2,6-dimethylphenyl)isoxazol-5-yl]-2-fluoro-2-butenal prepared in Preparative Example 30. $^1$H-NMR(400 MHz, DMSO-d$_6$) δ:
2.14(s, 6H), 2.25(s, 3H), 2.48(s, 3H), 6.08(s, 1H), 6.80–6.94(m, 3H), 7.15(s, 1H), 7.16(d, J=7.6 Hz, 2H), 7.20–7.29(m, 3H).

Preparative Example 31

5-Isopropyl-1-t-butylpyrazole-3-carbaldehyde

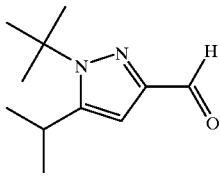

Step 1

6.3 g of metallic sodium was added to 100 ml of toluene. The obtained mixture was vigorously stirred at 110° C. for 30 minutes to prepare a dispersion of sodium in toluene. A liquid mixture comprising 26 g of methyl methoxyacetate and 39 g of 3-methyl-butyl-2-one was dropped into the above dispersion with the bulk temperature being kept at 55 to 60° C. The obtained mixture was further stirred at 60° C. for 3 hours and cooled to 0° C., followed by the addition of 10 ml of ethanol and 50 ml of 10% hydrochloric acid. The obtained mixture was extracted with ethyl acetate. The organic phase was washed with a saturated aqueous solution of common salt, dried over magnesium sulfate and concentrated in a vacuum to give 40 g of a crude diketone having the following structure:

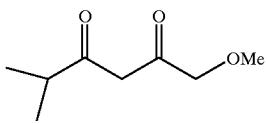

$^1$H-NMR(400 MHz, CDCl$_3$) δ:
1.16(d, J=6.0 Hz, 6H), 3.43(s, 3H), 4.00(s, 2H), 5.80(s, 1H).

Step 2

9.46 g of t-butylhydrazine hydrochloride was added to 100 ml of an ethanolic solution of 10 g of the above diketone. The obtained mixture was heated under reflux for 2 hours and distilled to remove the solvent. Water was added to the residue, followed by the extraction with ethyl acetate. The organic phase was washed with a saturated aqueous solution of common salt, dried over magnesium sulfate and concentrated in a vacuum to give 8.1 g of a pyrazole having the following structure as a pale-yellow oil:

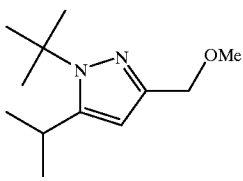

$^1$H-NMR(400 MHz, CDCl$_3$) δ:
1.24(d, J=6.0 Hz, 6H), 1.62(s, 9H), 3.28–3.36(m, 1H), 3.40(s, 3H), 4.28(s, 2H), 6.14(s, 1H).

Step 3

42.3 ml of a 1.0M solution of boron tribromide in methylene chloride was dropped into 230 ml of a solution of 8.1 g of the above pyrazole in methylene chloride at 0° C. After the completion of the dropping, the obtained mixture was further stirred at 0° C. for 30 minutes and poured into 200 ml of 10% aqueous ammonia, followed by the extraction with ethyl acetate. The organic phase was washed with a saturated aqueous solution of common salt, dried over magnesium sulfate and concentrated in a vacuum to give 9.3 g of a crude bromide.

Water (90 ml) and sodium carbonate (7.3 g) were added to 90 ml of a solution of 9.3 g of the above bromide in 1,4-dioxane. The obtained mixture was heated under reflux for 1.5 hours and distilled to remove the 1,4-dioxane, followed by the extraction with ethyl acetate. The organic phase was washed with a saturated aqueous solution of common salt, dried over magnesium sulfate and concentrated in a vacuum to give 6.7 g of a crude alcohol as a yellow oil.

Manganese dioxide (35 g) was added to 150 ml of a solution of 6.7 g of the crude alcohol in methylene chloride. The obtained mixture was stirred at room temperature for 15 hours and filtered through Celite. The filtrate was distilled to remove the solvent. The obtained residue was purified by silica gel column chromatography (5% ethyl acetate/hexane) to give 4.7 g of the title compound as a pale-yellow oil.

$^1$H-NMR(400 MHz, CDCl$_3$) δ:
1.28(d, J=6.0 Hz, 6H), 1.68(s, 9H), 3.32–3.40(m, 1H), 6.66(s, 1H), 9.88(s, 1H).

Preparative Example 32

1-(5-Isopropyl-1-t-butylpyrazol-3-yl)ethanone

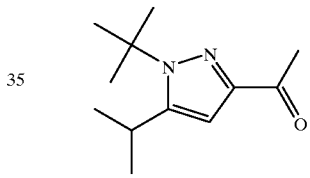

In a similar manner to that described in Steps 3 and 4 of Example 1, the title compound was prepared from 5-isopropyl-1-t-butylpyrazole-3-carbaldehyde prepared in Preparative Example 31.

$^1$H-NMR(400 MHz, CDCl$_3$) δ:
1.26(d, J=6.0 Hz, 6H), 1.66(s, 9H), 2.52(s, 3H), 3.32–3.40 (m, 1H), 6.44(s, 1H)

Preparative Example 33

(E)-3-(5-Isopropyl-1-t-butylpyrazol-3-yl)-2-butenal

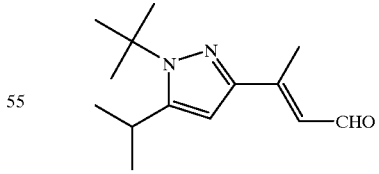

In a similar manner to that described in Step 5 of Example 1 and Steps 1 and 2 of Example 2, the title compound was prepared from 1-(5-isopropyl-1-t-butylpyrazol-3-yl) ethanone prepared in Preparative Example 32.

$^1$H-NMR(400 MHz, CDCl$_3$) δ:
1.26(d, J=6.0 Hz, 6H), 1.66(s, 9H), 2.54(d, J=1.2 Hz, 3H), 3.32–3.40(m, 1H), 6.43(s, 1H), 6.52(dd, J=1.2, 8.4 Hz, 1H), 10.16(d, J=8.4 Hz, 1H).

Example 129
(E,E,E)-7-(5-Isopropyl-1-t-butylpyrazol-3-yl)-3-methyl-octa-2,4,6-trienoic acid

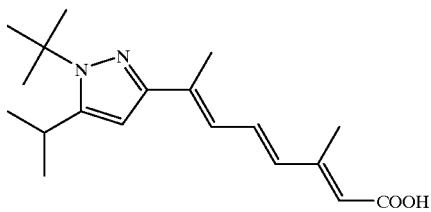

In a similar manner to that described in Steps 3 and 4 of Example 2, the title compound was prepared from (E)-3-(5-isopropyl-1-t-butylpyrazol-3-yl)-2-butenal prepared in Preparative Example 33.

$^1$H-NMR(400 MHz, DMSO-d$_6$) δ:
1.21(d, J=6.8 Hz, 6H), 1.57(s, 9H), 2.13(s, 3H), 2.27(s, 3H), 5.75(s, 1H), 6.41(d, J=15.2 Hz, 1H), 6.47(s, 1H), 6.71(d, J=11.6 Hz, 1H), 7.02(dd, J=11.6, 15.2 Hz, 1H).

Preparative Example 34
(E)-2-Fluoro-3-(5-isopropyl-1-t-butylpyrazol-3-yl)-2-butenal

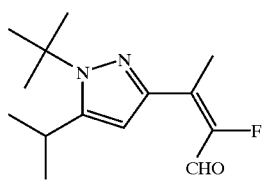

In a similar manner to that described in Steps 1 to 3 of Example 5, the title compound was prepared from 1-(5-isopropyl-1-t-butylpyrazol-3-yl) ethanone prepared in Preparative Example 32.

$^1$H-NMR(400 MHz, CDCl$_3$) δ:
1.29(d, J=7.2 Hz, 6H), 1.64(s, 9H), 2.22(d, J=4.0 Hz, 3H), 3.32–3.40(m, 1H), 6.28(s, 1H), 10.08(d, J=20 Hz, 1H).

Example 130
(E,E,E)-6-Fluoro-7-(5-isopropyl-1-butylpyrazol-3-yl)-3-methyl-octa-2,4,6-trienoic acid

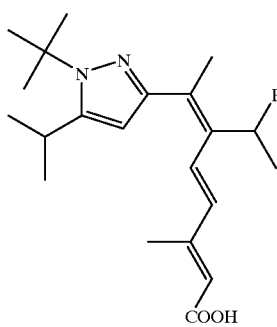

In a similar manner to that described in Steps 3 and 4 of Example 2, the title compound was prepared from (E)-2-fluoro-3-(5-isopropyl-1-t-butylpyrazol-3-yl)-2-butenal prepared in Preparative Example 34.

$^1$H-NMR(400 MHz, DMSO-d$_6$) δ:
1.22(d, J=6.8 Hz, 6H), 1.60(s, 9H), 2.04(s, 3H), 2.22(s, 3H), 3.32–3.42(m, 1H), 5.92(s, 1H), 6.41(s, 1H), 6.58(d, J=16.0 Hz, 1H), 7.82(dd, J=16.0, 30.0 Hz, 1H).

Preparative Example 35
1-(2,5-Dimethylphenyl)-5-methylpyrazole-3-carbaldehyde

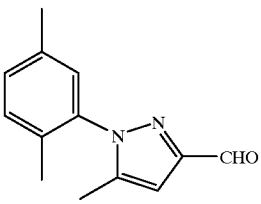

The title compound was prepared in a similar manner to that described in Preparative Example 31.

$^1$H-NMR(400 MHz, CDCl$_3$) δ:
2.02(s, 3H), 2.14(s, 3H), 2.18(s, 3H), 6.71(s, 1H), 7.08(s, 1H), 7.24(br.s, 2H)

Preparative Example 36
(E)-3-[1-(2,5-Dimethylphenyl)-5-methylpyrazol-3-yl]-2-butenal

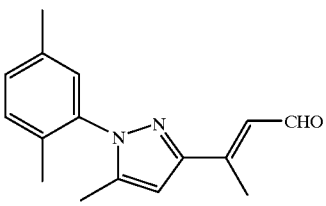

In a similar manner to that described in Steps 2 to 5 of Example 1 and Steps 1 and 2 of Example 2, the title compound was prepared from 1-(2,5-dimethyl-phenyl)-5-methylpyrazole-3-carbaldehyde prepared in Preparative Example 35.

$^1$H-NMR(400 MHz, CDCl$_3$) δ:
2.02(s, 3H), 2.14(s, 3H), 2.36(s, 3H), 2.58(d, J=1.2 Hz, 1H), 6.48(s, 1H), 6.54(dd, J=1.2, 8.0 Hz, 1H), 7.06(s, 1H), 7.18(d, J=8.0 Hz, 1H), 7.21(d, J=8.0 Hz, 1H), 10.20(d, J=8.0 Hz, 1H).

Example 131
(E,E,E)-7-[1-(2,5-Dimethylphenyl)-5-methylpyrazol-3-yl]-3-methyl-octa-2,4,6-trienoic acid

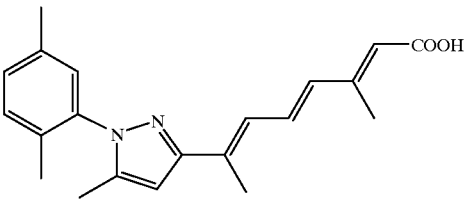

In a similar manner to that described in Steps 3 and 4 of Example 2, the title compound was prepared from (E)-3-[1-(2,5-dimethylphenyl)-5-methylpyrazol-3-yl]-2-butenal prepared in Preparative Example 36.

$^1$H-NMR(400 MHz, DMSO-d$_6$) δ:
1.91(s, 3H), 2.03(s, 3H), 2.15(s, 3H), 2.28(s, 3H), 2.48(s, 3H), 5.78(s, 1H), 6.47(d, J=15.2 Hz, 1H), 6.52(s, 1H), 6.81(d, J=11.6 Hz, 1H), 7.07(dd, J=11.6, 15.2 Hz, 1H), 7.09(s, 1H), 7.21(d, J=8 Hz, 1H), 7.26(d, J=8 Hz, 1H).

Preparative Example 37

5-Isopropyl-1-(2,2,2-trifluoroethyl)pyrazole-3-carbaldehyde

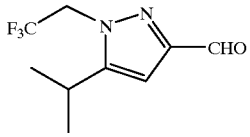

The title compound was prepared in a similar manner to that described in Preparative Example 31.

$^1$H-NMR(400 MHz, CDCl$_3$) δ:

1.28(d, J=6.0 Hz, 6H), 2.92–3.04(m, 1H), 4.76(dd, J=8.0, 16.4 Hz, 2H), 6.66(1H, s), 9.94(s, 1H).

Preparative Example 38

1-[5-Isopropyl-1-(2,2,2-trifluoroethyl)pyrazol-3-yl]ethanone

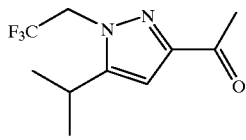

In a similar manner to that described in Steps 3 and 4 of Example 1, the title compound was prepared from 5-isopropyl-1-(2,2,2-trifluoroethyl)pyrazole-3-carbaldehyde prepared in Preparative Example 37.

$^1$H-NMR(400 MHz, CDCl$_3$) δ:

1.28(d, J=6 Hz, 6H), 2.54(s, 3H), 2.90–3.00(m, 1H), 4.71(dd, J=8.0, 16.4 Hz, 2H), 6.63(s, 1H).

Preparative Example 39

(E)-3-[5-Isopropyl-1-(2,2,2-trifluoroethyl)pyrazol-3-yl]-2-butenal

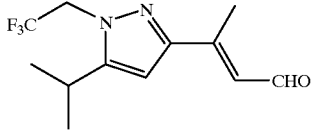

In a similar manner to that described in Step 5 of Example 1 and Steps 1 and 2 of Example 2, the title compound was prepared from 1-[5-isopropyl-1-(2,2,2-trifluoroethyl)pyrazol-3-yl]ethanone prepared in Preparative Example 38.

$^1$H-NMR(400 MHz, CDCl$_3$) δ:

1.28(d, J=6 Hz, 6H), 2.54(s, 3H), 2.90–3.00(m, 1H), 4.67(dd, J=8.0, 16.4 Hz, 2H), 6.39(s, 1H), 6.50(dd, J=1.6, 8.0 Hz, 2H), 10.20(d, J=8.0 Hz, 1H).

Example 132

(E,E,E)-7-[5-Isopropyl-1-(2,2,2-trifluoroethyl)pyrazol-3-yl]-3-methyl-octa-2,4,6-trienoic acid

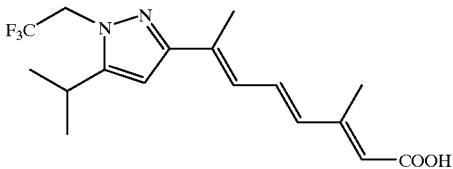

In a similar manner to that described in Steps 3 and 4 of Example 2, the title compound was prepared from (E)-3-[5-isopropyl-1-(2,2,2-trifluoroethyl)-pyrazol-3-yl]-2-butenal prepared in Preparative Example 39.

$^1$H-NMR(400 MHz, DMSO-d$_6$) δ:

1.28(d, J=6 Hz, 6H), 2.12(s, 3H), 2.28(s, 3H), 3.00–3.12 (m, 1H), 5.05(dd, J=8.0, 16.4 Hz, 2H), 5.78(s, 1H), 6.33(s, 1H), 6.47(d, J=15.2 Hz, 1H), 6.80(d, J=10.8 Hz, 1H), 7.03(dd, J=10.8, 15.2 Hz, 1H).

Pharmacological Experimental Examples will be described to illustrate the effects of the present invention.

Receptor binding assay using nuclear extract fraction of cells bearing RXR a genes transferred thereto.

A human RXR α gene was transferred into BHK (baby hamster kidney) cells to prepare cells constantly expressing RXR α proteins. The specific binding of 9-cis retinoic acid for RXR was determined by the use of a nuclear extract fraction of the cells, and the ability of each compound to bind RXR was determined by measuring the inhibition against the specific binding.

The nuclear extract fraction was prepared as follows.

The above BHK cells (5×10$^8$) into which an RXR α gene had been transferred were suspended in 15 ml of solution A (sodium phosphate (pH7.4): 5 mM, monothioglycerol: 10 mM, glycerol: 10% (v/v), phenylmethylsulfonyl fluoride (PMSF): 1 mM, aprotinin: 10 μg/ml, and leupeptin: 25 μg/ml). The obtained suspension was homogenized by the use of a homogenizer and centrifuged to remove the resulting supernatant. The sediment thus formed was suspended in 15 ml of solution B (Tris-HCl (pH8.5): 10 mM, monothioglycerol: 10 mM, glycerol: 10% (v/v), PMSF: 1 mM, aprotinin: 10 μg/ml, leupeptin: 25 μg/ml, and KCl:0.4 M). The obtained suspension was allowed to stand at 4° C. for one hour, and subjected to ultracentrifugation (100,000×g, 4° C., 1 hr). The obtained supernatant was stored as the nuclear extract fraction in a frozen state at −80° C. until the use (METHODS IN ENZYMOLOGY, 189, 248).

The receptor binding assay was conducted as follows.

180 μl of the above fraction and 10 μl of a dilution of 9-cis retinoic acid or a test compound were added to each well of a 96-well plate made of polypropylene, followed by the addition of 10 μl of 10nM $^3$H-9-cis retinoic acid. The resulting plate was allowed to stand at 4° C. for 16 hours. A solution containing 3% of charcoal and 0.3% of dextran was added to the resulting reaction mixture. The mixture thus obtained was centrifuged to remove free $^3$H-9-cis retinoic acid. The radioactivity of the resulting supernatant was determined by the use of a scintillation counter. The specific binding of $^3$H-9-cis retinoic acid for RXR was determined by assuming the radioactivity found when 200 times as much 9-cis retinoic acid was added to be the non-specific binding and subtracting it from the radioactivity determined above. The compounds of the present invention inhibited the binding of $^3$H-9-cis retinoic acid dependently on the concentration. The 50% inhibitory concentration of each test compound was calculated and the relative activities were calculated by assuming the inhibitory concentration of 9-cis retinoic acid to be 1.0. The results are given in Table 1.

TABLE 10

| Ex. No. | Results of RXR α binding assay (relative IC$_{50}$) |
| --- | --- |
| control (9-cis Retinoic Acid) | 1.0 |
| 2 | 15.8 |
| 5 | 4.7 |
| 6 | 7.1 |
| 9 | 1.3 |
| 12 | 1.8 |
| 15 | 1.8 |
| 18 | 5.6 |
| 21 | 0.8 |
| 36 | 1.5 |
| 42 | 1.1 |
| 45 | 1.7 |
| 54 | 1.7 |
| 57 | 14.0 |
| 60 | 3.0 |

Method for experiment on RXR α transcription system

The method for determining the activity of novel retinoid compounds of accelerating transcription through retinoid X receptor α (RXR α) will now be described.

Human RXR α expression vectors and PLAP vectors (i.e., vectors containing integrated thereinto a secretor alkaline phosphatase (PLAP) gene of which the expression is inhibited by the competent sequence of the RXR α in the presence of a ligand were temporarily transferred into COS-7 (African green monkey kidney cells) and the PLAP activity was determined by the chemiluminescence method. This PLAP gene is an artificial mutant deficient in membrane-binding site, so that it is secreted into a cell-culturing medium when expressed.

COS-7 cells (1.0×10$^6$) were scattered on a 60-mm culture dish. One day after, human RXR α expression vectors and PLAP vectors were transferred into the cells each in an amount of 10 μg by the DEAE-dextran method. Another day after, the resulting cells were torn off by trypsinization and put on a 96-well culture plate in an amount of 2×10$^4$ per unit well. Four hours after, the cells were put on 100 μl of a medium containing retinoid compounds in a concentration of 0 to 1 μM. Sampling was conducted after 44 hours and the obtained samples were treated at 65° C. for 10 minutes to eliminate the non-specific activity. Sumilight (a product of Sumitomo Metal Industries, Ltd.) was used as the substrate of the chemiluminescence reaction. 30 minutes after the initiation of the reaction, the intensity of luminescence was determined. The results are given in FIG. 1. The plots are each given in terms of the average of five samples.

It is apparent from the above results that the compounds of the present invention exhibit agonism for RXR receptors. Therefore, the compounds are expected to be useful as preventive and therapeutic agents for autoimmune diseases, immunosuppression in organ transplantation or malignant neoplasm to give drugs efficacious against the following various diseases:

various cornification anomalies, psoriasis, acne, leukoplakia, and xeroderma pigmentosum;

various alopeciae such as alopecia areata, seborrheic alopecia and cachectic alopecia;

postmenopausal osteoporosis, senile osteoporosis, idiopathic osteoporosis, diabetic osteopenia, rheumatoid osteopenia, renal osteomalacia and ectopic hyperostosis;

osteoarthritis and shoulder periarthritis;

rheumatoid arthritis, multiple sclerosis (MS), systemic lupus erythematosus (SLE), Behcet disease, mycosis fungoides (MF), systemic scleroderma, dermatomyositis (OM), nodular arteriosclerosis (PM), thrombocytopenia and insulin dependent diabetes melitus;

immunosuppression in organ transplantation;

atopic dermatitis and asthma;

hyperthyroidism;

squamous cell carcinoma, bladder cancer, lung cancer, esophageal carcinoma, head and neck cancer, acute promyelocytic leukemia and myelocytic leukemia;

hyperkalemia; and pulmonary fibrosis, hepatic fibrosis, and hepatic cirrhosis.

The compounds of the present invention may be orally administered as preventive or therapeutic agents for these diseases in the form of tablet, powder, granule, capsule, syrup or the like, or may be parenterally administered in the form of suppository, injection, external preparation or drop.

Pharmaceutical preparations for oral or parenteral administration according to the present invention can be formulated by the use of conventional pharmaceutically acceptable carriers in a conventional manner.

Subcutaneous, intramuscular or intravenous injections or dropping injections according to the present invention can be formulated by conventional processes of adding a pH regulator, buffer, stabilizer or solubilizing agent to a base at need and, if necessary, freeze-drying the obtained mixture.

The compounds according to the second embodiment of the present invention and the preparation thereof will now be described in more detail by referring to the following Examples, though the present invention is not limited by them. Further, the preparation of starting compounds used in the Examples will be described in Referential Examples. No peak assignable to carboxyl was detected in NMR spectroscopy of some compounds. The determination of melting points was conducted by the use of a melting point apparatus for trace samples (mfd. by Yanagimoto Manufacturing Co., Ltd.)

Example 201

Preparation of 4-[5,6-dihydro-2,3-diisopropyl-9-(3-pyridylmethyl)pyrrolo[2,3-f]quinoxalin-7-yl]benzoic acid Step 1

Preparation of methyl 4-(7,8-dihydro-2,3-diisopropyl-5(2H)-quinoxalinon-6-ylidene)benzoate

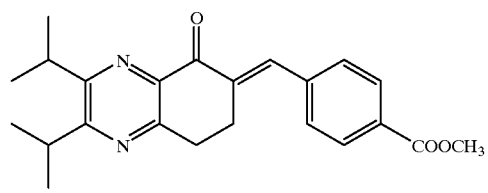

2.0 g of 5,6,7,8-tetrahydro-2,3-diisopropyl-5- quinoxalinone and 1.27 g of methyl terephthalaldehydate were dissolved in 10 ml of acetic acid, followed by the addition of 2 ml of concentrated sulfuric acid. The obtained mixture was stirred at room temperature overnight and poured into a saturated aqueous solution of sodium hydrogencarbonate. The obtained mixture was extracted with ethyl acetate. The organic phase was washed with water and a saturated aqueous solution of common salt, dried over anhydrous magnesium sulfate and concentrated in a vacuum. The residue was purified by silica gel column chromatography (developer: 20% ethyl acetate/hexane) to give 1.04 g of the title compound as a white solid.
M.p.: 100 to 102° C.
$^1$H-NMR(400 MHz, CDCl$_3$) δ:
1.31(d, J=6.8 Hz, 6H), 1.37(d, J=6.8 Hz, 6H), 3.10–3.22 (m, 4H), 3.38–3.47(m, 2H), 3.05(s, 3H), 7.50(d, J=8.2 Hz, 2H), 7.89(s, 1H), 8.09(d, J=8.2 Hz, 2H).

Step 2

Preparation of methyl 4-[1-(7,8-dihydro-2,3-diisopropyl-5(2H)-quinoxalinon-6-yl)-2,2-dimethoxyethyl]benzoate

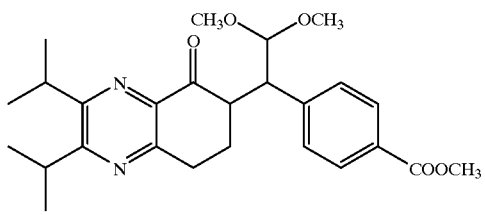

1.0 g of methyl 4-(7,8-dihydro-2,3-diisopropyl-5(2H)-quinoxalinon-6-ylidene)benzoate was dissolved in a solvent mixture comprising 12 ml of nitromethane and 4 ml of tetrahydrofuran, followed by the addition of 1 ml of a 40% methanolic solution of benzyltrimethylammonium hydroxide. The obtained mixture was stirred at room temperature overnight, followed by the addition of ethyl acetate. The organic phase was washed with dilute hydrochloric acid, water, a saturated aqueous solution of sodium hydrogencarbonate and a saturated aqueous solution of common salt successively, dried over anhydrous magnesium sulfate and concentrated in a vacuum to give 1.38 g of a brown oil.

This oil was dissolved in a solvent mixture comprising 15 ml of methylene chloride and 15 ml of tetrahydrofuran. 1.5 ml of a 28% solution of sodium methoxide was added to the solution at −35° C., followed by the stirring for 40 minutes.

This solution was dropped into a separately prepared solvent mixture comprising 4 ml of concentrated sulfuric acid and 20 ml of methanol at −35° C. The obtained mixture was stirred at room temperature for 30 minutes and poured into a saturated aqueous solution of sodium hydrogencarbonate. The obtained mixture was extracted with ethyl acetate. The organic phase was washed with water and a saturated aqueous solution of common salt, dried over anhydrous magnesium sulfate and concentrated in a vacuum to give 1.24 g of the title compound as a brown powder. This powder was used in the subsequent step without further purification.

Step 3

Preparation of 4-[5,6-dihydro-2 3-diisopropyl-9-(3-pyridylmethyl)pyrrolo[2,3-f]quinoxalin-7-yl]benzoic acid

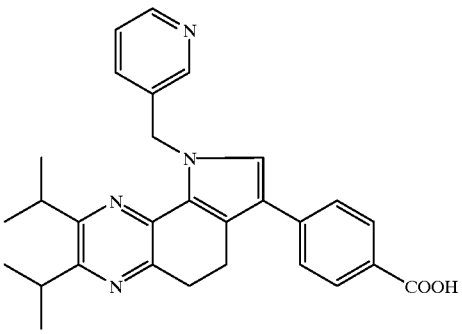

0.6 g of methyl 4-[1-(7,8-dihydro-2,3-diisopropyl-5(2H)-quinoxalinon-6-yl)-2,2-dimethoxyethyl]benzoate and 0.202 ml of 3-aminomethylpyridine were dissolved in 10 ml of acetic acid. The obtained solution was heated under reflux for one hour and cooled to room temperature by allowing to stand, followed by the addition of water. The obtained mixture was extracted with ethyl acetate. The organic phase was washed with a saturated aqueous solution of sodium hydrogen-carbonate and a saturated aqueous solution of common salt, dried over anhydrous magnesium sulfate, and concentrated in a vacuum. The obtained residue was purified by silica gel chromatography (developer: 30% ethyl acetate/hexane) to give 0.15 g of a light-brown powder.

This powder was dissolved in 15 ml of ethanol, followed by the addition of 5 ml of a 5N aqueous solution of sodium hydroxide. The obtained mixture was stirred at room temperature for 4 hours. Dilute hydrochloric acid was added to the mixture under stirring to precipitate crystals. The crystals were recovered by filtration, washed with water and dried in a vacuum to give 0.1 g of the title compound as a light-brown solid.
M.p.: 158 to 160° C.
$^1$H-NMR(400 MHz, DMSO-d$_6$) δ:
1.0l(d, J=6.6 Hz, 6H), 1.17(d, J=6.6 Hz, 6H), 3.04(s, 4H), 3.18–3.32(m, 2H), 5.90(s, 2H), 7.30(dd, J=4.6, 7.8 Hz, 1H), 7.44(d, J=7.8 Hz, 1H), 7.52(d, J=7.9 Hz, 2H), 7.54(s, 1H), 7.91(d, J=7.9 Hz, 2H), 8.38(s, 1H), 8.41(d, J=4.6 Hz, 1H).

The compound of Example 202 was prepared in a similar manner to that described in Example 201.

Example 203

Preparation of 4-[4,5-dihydro-7,8-diisopropyl-1-(3-pyridylmethyl)pyrazolo[5,4-f]quinoxalin-3-yl]benzoic acid

Step 1

Preparation of methyl 4-(7,8-dihydro-2,3-diisoproyl-5(2H)-auinoxalinon-6-yl-carbonyl)benzoate

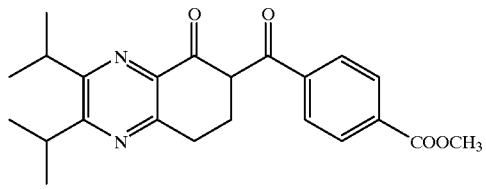

0.74 g of 5,6,7,8-tetrahydro-2,3-diisopropyl-5-quinoxaline was dissolved in 20 ml of tetrahydrofuran. 3.51 ml of a 1M tetrahydrofuran solution of lithium bistrimethylsilylamide was dropped into the solution at −78° C. The obtained mixture was stirred for 30 minutes, followed by the addition of a solution of 0.7 g of chloride of monomethyl terephthalate in 5 ml of tetrahydrofuran. The obtained mixture was stirred for one hour, followed by the addition of a saturated aqueous solution of ammonium chloride. The obtained mixture was extracted with ethyl acetate. The organic phase was washed with water and a saturated aqueous solution of common salt, dried over anhydrous magnesium sulfate and concentrated in a vacuum. The residue was purified by silica gel chromatography (developer: 10% ethyl acetate/hexane) to give 0.58 g of the title compound as a brown solid.
M.p.: 82 to 84° C.
$^1$H-NMR(400 MHz, CDCl$_3$) δ:
 1.30(d, J=6.8 Hz, 6H), 1.36(d, J=6.8 Hz, 6H), 2.82–2.87 (m, 2H), 3.00–3.04(m, 2H), 3.37–3.45(m, 2H), 3.96(s, 3H), 7.66(d, J=8.6 Hz, 2H), 8.14(d, J=8.6 Hz, 2H).

Step 2

Preparation of methvl 4-(4,5-dihydro-7,8-diisopropylpyrazolo[5 4-f]quinoxalin-3-yl)benzoate

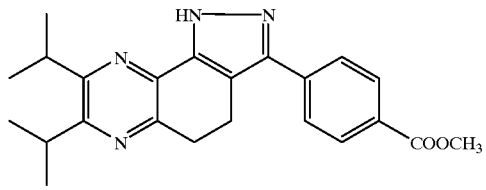

0.58 g of methyl 4-(7,8-dihydro-2,3-diisopropyl-5(2H)-quinoxaline-6-carbonyl)benzoate was dissolved in 10 ml of acetic acid, followed by the addition of 0.107 ml of hydrazine monohydrate. The obtained mixture was heated under reflux for 4 hours, cooled to room temperature by allowing to stand and, poured into a saturated aqueous solution of sodium hydrogen-carbonate. The obtained mixture was extracted with ethyl acetate. The organic phase was washed with water and a saturated aqueous solution of common salt, dried over anhydrous magnesium sulfate and concentrated in a vacuum. The obtained residue was purified by silica gel chromatography (developer: 5% ethyl acetate/hexane) to give 0.524 g of the title compound as a pale-yellow solid.
M.p.: 204 to 206° C.
$^1$-NMR(400 MHz, CDCl$_3$) δ:
 1.30(d, J=6.8 Hz, 6H), 1.32(d, J=6.8 Hz, 6H), 3.16–3.26 (m, 4H), 3.32–3.39(m, 2H), 3.95(s, 3H), 7.83(d, J=8.6 Hz, 2H), 8.12(d, J=8.6 Hz, 2H).

Step 3

Preparation of 4-[4 5-dihydro-7,8-diisopropyl-1-(3-pyridylmethyl)pyrazolo[5,4-f]quinoxalin-3-yl]benzoic acid

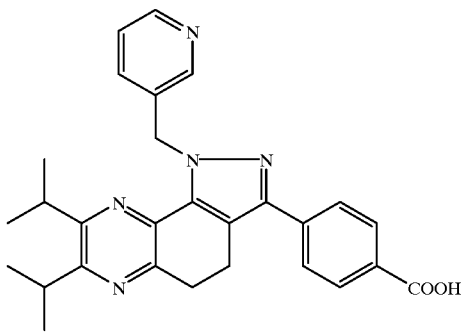

0.19 g of methyl 4-(4,5-dihydro-7,8-diisopropyl-pyrazolo[5,4-f]quinoxalin-3-yl)benzoate was dissolved in 10 ml of N,N-dimethylformamide. The obtained solution was cooled to 0° C., followed by the addition of 0.04 g of sodium hydride. The obtained mixture was stirred for 10 minutes, followed by the addition of 0.08 g of 3-picolyl chloride hydrochloride. The obtained mixture was stirred for 10 minutes, then at room temperature for 30 minutes, followed by the addition of a saturated aqueous solution of ammonium chloride. The precipitated crystals were recovered by filtration, washed with water and dried in a vacuum to give 0.144 g of a light-brown powder.

This powder was dissolved in 15 ml of ethanol, followed by the addition of 5 ml of a 5N aqueous solution of sodium hydroxide. The obtained mixture was stirred at room temperature for one hour, followed by the addition of dilute hydrochloric acid under stirring. The crystals thus precipitated were recovered by filtration, washed with water and dried in a vacuum to give 0.13 g of the title compound as a white solid.
M.p.: 279 to 281° C.
$^1$H-NMR(400 MHz, DMSO-d$_6$) δ:
 1.21(d, J=6.4 Hz, 6H), 1.29(d, J=6.4 Hz, 6H), 3.14–3.25 (m, 4H), 3.27–3.37(m, 2H), 6.16(s, 2H), 7.21–7.28(m, 1H), 7.60–7.65(m, 1H), 7.85(d, J=8.2 Hz, 2H), 8.17(d, J=8.2 Hz, 2H), 8.49–8.56(m, 1H), 8.58–8.66(m, 1H).

The compound of Example 204 was prepared in a similar manner to that described in Example 203.

| Ex. | Structural Formula | $^1$H-NMR (400MHz, DMSO-$d_6$) δ | m.p. (° C.) |
|---|---|---|---|
| 204 | 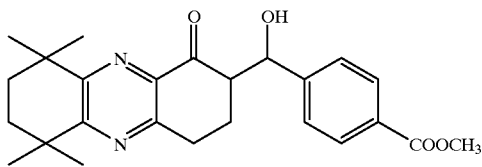 | 1.01(d, J=6.8Hz, 6H),<br>1.26(d, J=6.8Hz, 6H),<br>3.16~3.31(m, 7H),<br>6.23(s, 2H),<br>6.75(d, J=8.0Hz, 1H),<br>7.12~7.17(m, 1H),<br>7.54(ddd, J=2.1, 8.0, 8.0Hz, 1H),<br>7.88(d, J=8.6Hz, 2H),<br>8.16(d, J=8.6Hz, 2H),<br>8.59~8.63(m, 1H). | 256~258 |

Example 205

Preparation of 4-[4,5,7,8,9,10-hexahydro-7,7,10,10-tetramethyl-1-(3-pyridylmethyl)pyrrolo[2 3-a]-phenazin-3-yl]benzoic acid

Step 1

Preparation of methyl 4-[3,4,6,7,8,9-hexahydro-6,6,9,9-tetramethyl-1(2H)-phenazinon-2-yl)hydroxymethyl]benzoate

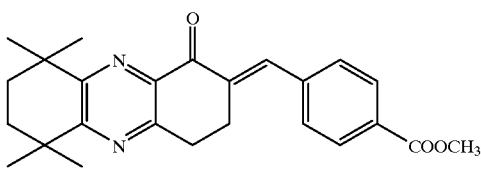

0.5 g of 1,2,3,4,6,7,8,9-octahydro-6,6,9,9-tetramethylphenazin-1-one and 0.38 g of methyl terephthalaldehydate were dissolved in 15 ml of methanol, followed by the addition of a small amount of sodium hydroxide. The obtained mixture was stirred overnight to precipitate crystals. The crystals were recovered by filtration, washed with a small amount of methanol and dried in a vacuum to give 0.53 g of the title compound as a white solid.

M.p.: 190 to 192° C.

$^1$H-NMR(400 MHz, CDCl$_3$) δ:

1.30(s, 3H), 1.32(s, 3H), 1.38(s, 6H), 1.82(s, 4H), 1.85–1.92(m, 1H), 2.12–2.23(m, 1H), 2.89– 2.92(m, 1H), 2.93–3.16(m, 3H), 3.92(s, 3H), 5.78–5.81(m, 1H), 7.48(d, J=8.0 Hz, 2H), 8.06(d, J=8.0 Hz, 2H).

Step 2

Preparation of methyl 4-(3,4,6,7,8,9-hexahydro-6,6,9,9-tetramethyl-1(2H)-phenazinon-2-ylidene)benzoate

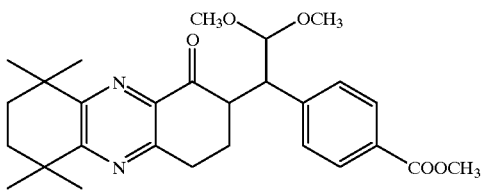

0.53 g of methyl 4-[(3,4,6,7,8,9-hexamethyl-6,6,9,9-tetramethyl-1(2H) -phenazinon-2-yl)hydroxymethyl]benzoate was dissolved in 12 ml of 1,4-dioxane, followed by the addition of 1 ml of concentrated sulfuric acid. The obtained mixture was stirred at 60° C. for 6 hours and poured into a saturated aqueous solution of sodium hydrogencarbonate. The obtained mixture was extracted with ethyl acetate. The organic phase was washed with a saturated aqueous solution of common salt, dried over anhydrous magnesium sulfate and concentrated in a vacuum. The residue was washed with hexane, followed by the recovery of crystals by filtration. The crystals were dried in a vacuum to give 0.36 g of the title compound as a pale-yellow solid.

M.p.: 149 to 151° C.

$^1$H-NMR(400 MHz, CDCl$_3$) δ:

1.35(s, 6H), 1.41(s, 6H), 1.84(s, 4H), 3.10–3.23(m, 2H), 3.95(s, 3H), 7.50(d, J=8.3 Hz, 2H), 3.09(d, J=8.4 Hz, 2H).

Step 3

Preparation of methyl 4-[1-(3,4,6,7,8,9-hexahydro-6,6,9,9-tetramethyl-1(2H)-phenazinon-2-yl)-2 2-dimethoxyethyl)benzoate 0.6 g of methyl 4-(3,4,6,7,8,9-hexahydro-6,6,9,9- tetramethyl-1(2H)-phenazinon-2-ylidene)benzoate was dissolved in a solvent mixture comprising 7 ml of nitromethane and 3 ml of tetrahydrofuran, followed by the addition of 0.3 ml of a 40% methanolic solution of benzyltrimethylammonium hydroxide. The obtained mixture was stirred at room temperature overnight, followed by the addition of ethyl acetate. The formed organic phase was washed with dilute hydrochloric acid, water, a saturated aqueous solution of sodium hydrogencarbonate and a saturated aqueous solution of common salt successively, dried over anhydrous magnesium sulfate, and concentrated in a vacuum to give 0.74 g of a light-brown oil.

This oil was dissolved in a solvent mixture comprising 15 ml of methylene chloride and 15 ml of tetrahydrofuran. 0.78 ml of a 28% solution of sodium methoxide was added to the solution at −35° C., followed by the stirring for 40 minutes.

This solution was dropped into a separately prepared solvent mixture comprising 2 ml of concentrated sulfuric acid and 10 ml of methanol at −35° C. The mixture was stirred at room temperature for 30 minutes and poured into a saturated aqueous solution of sodium hydrogencarbonate, followed by the extraction with ethyl acetate. The organic phase was washed with water and a saturated aqueous solution of common salt, dried over anhydrous magnesium sulfate and concentrated in a vacuum to give 0.7 g of the title compound as a brown powder. This powder was used in the subsequent step without further purification.

Step 4

Preparation of methyl 4-[4,5,7,8,9,10-hexahydro-7,7,10,10-tetramethyl-1-(3-myridylmethyl)-pyrrolo[2,3-a]phenazin-3-yl]benzoate

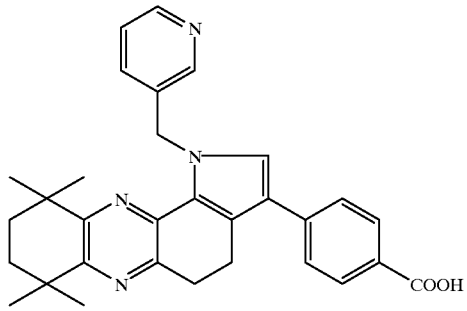

0.4 g of methyl 4-[1-(3,4,6,7,8,9-hexahydro-6,6,9,9-tetramethyl-1(2H)-phenazinon-2-yl)-2,2-dimethoxyethyl]benzoate and 0.13 ml of 3-aminomethylpyridine were dissolved in 8 ml of acetic acid. The obtained solution was heated under reflux for one hour and cooled to room temperature by allowing to stand, followed by the addition of water. The obtained mixture was extracted with ethyl acetate. The organic phase was washed with a saturated aqueous solution of sodium hydrogencarbonate and a saturated acueous solution of common salt, dried over anhydrous magnesium sulfate and concentrated in a vacuum. The obtained residue was purified by silica gel chromatography (developer: 30% ethyl acetate/hexane) to give 0.2 g of a brown powder.

This powder was dissolved in 15 ml of ethanol, followed by the addition of 5 ml of a 5N aqueous solution of sodium hydroxide. The obtained mixture was heated at 60° C. for one hour and cooled to room temperature by allowing to stand, followed by the addition of dilute hydrochloric acid under stirring. The crystals thus precipitated were recovered by filtration, washed with water and dried in a vacuum to give 0.1 g of the title compound as a pale-yellow solid.

M.p.: 245 to 247° C.

$^1$H-NMR(400 MHz, DMSO-$d_6$) δ:

1.03(s, 6H), 1.23(s, 6H), 1.67(s, 4H), 3.05(s, 4H), 5.89(s, 2H), 7.28–7.33(m, 1H), 7.40–7.44(m, 1H), 7.55(d, J=8.0 Hz, 2H), 7.57(s, 1H), 7.92(d, J=8.0 Hz, 2H), 8.34–8.37(m, 1H), 8.38–8.43(m, 1H).

In a similar manner to that described in Example 205, the compounds of Examples 206 to 212 were prepared by the use of the ketones prepared in Referential Examples 2 and 3 and 6,7,8,9-tetrahydro-9,9-dimethylothianaphtho[2,3-b]cyclohexan-1-one prepared in a similar manner to that described in Referential Example 3.

| Ex. | Structural Formula | $^1$H-NMR (400MHz, DMSO-$d_6$) δ | m.p. (° C.) |
|---|---|---|---|
| 206 | | 0.93(s, 6H), 1.21(s, 6H), 1.64(s, 4H), 3.05(s, 4H), 5.85(s, 2H), 6.96~7.00(m, 2H), 7.53~7.56(m, 3H), 7.94(d, J=8.4Hz, 2H), 8.42~8.48(m, 2H). | 238~240 |

-continued

| Ex. | Structural Formula | ¹H-NMR (400MHz, DMSO-d$_6$) δ | m.p. (° C.) |
|---|---|---|---|
| 207 | | 0.89(s, 6H), 1.20(s, 6H), 1.62(s, 4H), 3.01~3.11(m, 4H), 5.88(s, 2H), 6.65(d, J=7.7Hz, 1H), 7.18~7.22(m, 1H), 7.56(s, 1H), 7.57(d, J=8.2Hz, 2H), 7.62~7.65(m, 1H), 7.94(d, J=8.2Hz, 2H), 8.50~8.52(m, 1H). | 282~284 |
| 208 | | 1.06(s, 6H), 1.23(s, 6H), 1.67(s, 4H), 3.04(s, 4H), 7.06~7.11(m, 2H), 7.16~7.21(m, 1H), 7.24~7.30(m, 2H), 7.51(s, 1H), 7.55(d, J=8.2Hz, 2H), 7.92(d, J=8.2Hz, 2H). | 273~275 |
| 209 | | 1.37(s, 6H), 1.44(brs, 2H), 1.88(brs, 2H), 2.50~2.65(m, 4H), 2.78(t, J=7.3Hz, 2H), 5.45(s, 2H), 7.10~7.14(m, 1H), 7.22~7.29(m, 2H), 7.43(d, J=8.4Hz, 2H), 7.88(d, J=8.4Hz, 2H), 8.05~8.10(m, 1H), 8.35~8.40(m, 1H). | 223~224 |
| 210 | | 1.28(s, 6H), 1.38(s, 6H), 1.52(brs, 2H), 1.66(brs, 2H), 2.60(brs, 4H), 5.44(s, 2H), 7.10~7.18(m, 1H), 7.22(s, 1H), 7.24~7.31(m, 1H), 7.42(d, J=8.4Hz, 2H), 7.88(d, J=8.4Hz, 2H), 8.08(brs, 1H), 8.35~8.41(m, 1H), 12.75(brs, 1H). | 289~290 |
| 211 | | 1.32(s, 6H), 1.43(s, 6H), 1.64~1.75(m, 2H), 2.97(t, J=6.4Hz, 2H), 3.08(t, J=6.4Hz, 2H), 3.93(s, 3H), 7.43(d, J=8.4Hz, 2H), 7.80(s, 1H), 8.07(d, J=8.4Hz, 2H). | 137.5~138 |

Example 211

Preparation of 4-[4,5,7,8,9,10-hexahydro-7,7,10,10-tetramethyl-1-(3-pyridylmethyl)pyrazolo[5,4-a]-phenazin-3-yl]benzoic acid

Step 1

Preparation of methyl 4-(3,4,6,7,8,9-hexahydro-6,6,9,9-tetramethyl-1(2H)-phenazinon-2-yl-carbonyl)benzoate

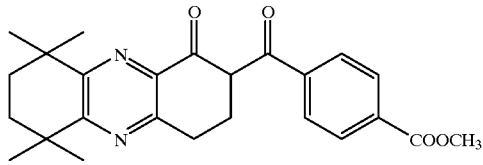

A solution of 0.2 ml of dimethyl sulfoxide in 1 ml of methylene chloride was dropped into a solution of 0.124 ml of oxalyl chloride in 10 ml of methylene chloride cooled to −60° C., followed by the stirring for 5 minutes. A solution of 0.5g of methyl 4-[(3,4,6,7,8,9-hexahydro-6,6,9,9-tetramethyl-1(2H)-phenazinon-2-yl)hydroxymethyl] benzoate in 10 ml of methylene chloride was dropped into the solution prepared above. The obtained mixture was stirred for 15 minutes, followed by the dropwise addition of 0.954 ml of triethylamine. The temperature of the reaction mixture was raised to room temperature. The resulting mixture was stirred for 30 minutes, followed by the addition of water. The obtained mixture was extracted with methylene chloride. The organic phase was washed with water and a saturated aqueous solution of common salt, dried over anhydrous magnesium sulfate and concentrated in a vacuum. The residue was purified by silica gel chromatography (developer: 5% ethyl acetate/hexane) to give 0.248 g of the title compound as a pale-yellow oil.

$^1$H-NMR(400 MHz, CDCl$_3$) δ:
1.34(s, 6H), 1.40(s, 6H), 1.83(s, 4H), 2.81–2.87(m, 2H), 2.98–3.04(m, 2H), 3.96(s, 3H), 7.67(d, J=8.6 Hz, 2H), 8.14(d, J=8.6 Hz, 2H).

Step 2

Precaration of methvl 4-(4,5,7,8,9,10-hexahydro-7,7,10,10-tetramethylpyrazolo[5,4-a]phenazin-3-yl)benzoate

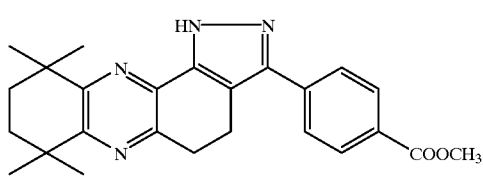

0.23 g of methyl 4-(3,4,6,7,8,9-hexahydro-6,6,9,9-tetramethyl-1(2H)-phenazinon-2-yl-carbonyl)benzoate was dissolved in 10 ml of methanol, followed by the addition of 0.04 ml of hydrazine monohydrate. The obtained mixture was heated under reflux for one hour and cooled with ice to precipitate crystals. The crystals were recovered by filtration, washed with a small amount of methanol and dried in a vacuum to give 0.16 g of the title compound as a white solid.

M.p.: 250 to 252° C.
$^1$H-NMR(400 MHz, CDCl$_3$) δ:
1.34(s, 6H), 1.36(s, 6H), 1.80(s, 4H), 3.16–3.25(m, 4H), 3.95(s, 3H), 7.83(d, J=8.6 Hz, 2H), 8.12(d, J=8.6 Hz, 2H).

Step 3

Preparation of 4-[4,5,7,8,9,10-hexahydro-7,7,10 10-tetramethyl-1-(3-pyridylmethyl)-pyrazolor[5,4-a] phenazin-3-yl]benzoic acid

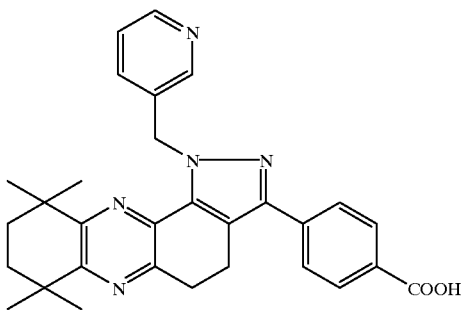

0.20 g of methyl 4-(4,5,7,8,9,10-hexahydro-7,7,10,10-tetramethylpyrazolo[5,4-a]phenazin-3-yl)benzoate was dissolved in 10 ml of N,N-dimethylformamide and the obtained solution was cooled to 0° C. 0.04 g of sodium hydride was added to the solution, followed by the stirring for 10 minutes. 0.09 g of 3-picolyl chloride hydrochloride was added to the resulting mixture, followed by the stirring for 10 minutes. The obtained mixture was further stirred at room temperature for 30 minutes, followed by the addition of a saturated aqueous solution of ammonium chloride. The obtained mixture was extracted with ethyl acetate. The organic phase was washed with water and a saturated aqueous solution of common salt, dried over anhydrous magnesium sulfate and concentrated in a vacuum. The residue was washed with hexane/diisopropyl ether and dried in a vacuum to give 0.15 g of a light-brown powder.

This powder was dissolved in 15 ml of ethanol, followed by the addition of 5 ml of a 5N aqueous solution of sodium hydroxide. The obtained mixture was stirred at room temperature for 4 hours, followed by the addition of dilute hydrochloric acid under stirring. The crystals thus precipitated were recovered by filtration, washed with water and dried in a vacuum to give 0.1 g of the title compound as a white solid.

M.p.: 265 to 267° C.
$^1$H-NMR(400 MHz, DMSO-d$_6$) δ:
1.13(s, 6H), 1.27(s, 6H), 1.73(s, 4H), 3.16(s, 4H), 6.02(s, 2H), 7.29–7.34(m, 1H), 7.50–7.55(m, 1H), 7.83(d, J=8.1Hz, 2H), 8.01(d, J=8.1 Hz, 2H), 8.42–8.46(m, 2H).

The compounds of Examples 212 and 213 were prepared in a similar manner to that described in Example 211.

| Ex. | Structural Formula | ¹H-NMR (400MHz, DMSO-d₆) δ | m.p. (° C.) |
|---|---|---|---|
| 212 | | 0.98(s, 6H), 1.24(s, 6H), 1.67(s, 4H), 3.18(s, 4H), 6.07(s, 2H), 6.77(d, J=8.0Hz, 1H), 7.20~7.25(m, 1H), 7.63~7.69(m, 1H), 7.83(d, J=8.0Hz, 2H), 8.01(d, J=8.0Hz, 2H), 8.48~8.53(m, 1H). | 280~282 |
| 213 | | 1.28(s, 6H), 1.32(s, 6H), 1.77(s, 4H), 3.10(s, 3H), 4.31(s, 3H), 7.81(d, J=7.6Hz, 2H), 8.00(d, J=7.6Hz, 2H). | 300 以上 |

Example 214

Preparation of 4-[7,8,9,10-tetrahydro-7,7,10,10-tetramethyl-1-(3-pyridylmethyl)pyrrolo[2,3-a]phenazin-3-yl]benzoic acid

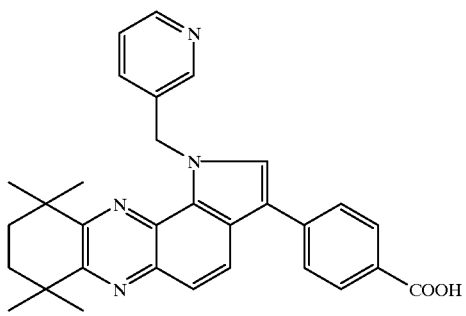

0.07 g of ethyl 4-[4,5,7,8,9,10-hexahydro-7,7,10,10-tetramethyl-1-(3-pyridylmethylpyrrolo[2,3-a]phenazin-3-yl)benzoate was dissolved in 10 ml of 1,4-dioxane, followed by the addition of 0.03 g of 2,3-dichloro-5,6-dicyano-1,4-benzoquinone. The obtained mixture was heated under reflux overnight and concentrated in a vacuum. The obtained residue was purified by silica gel chromatography (developer: 30% ethyl acetate/hexane) to give 0.05 g of a light-brown powder.

This powder was dissolved in 10 ml of ethanol, followed by the addition of 5 ml of a 5N aqueous solution of sodium hydroxide. The obtained mixture was stirred under heating at 60° C. for one hour and cooled by allowing to stand. Dilute hydrochloric acid was added to the resulting reaction mixture under stirring to precipitate crystals. The crystals were recovered by filtration, washed with water and dried in a vacuum to give 0.03 g of the title compound as a pale-yellow solid.
M.p.: 286 to 288° C.
¹H-NMR(400 MHz, DMSO-d₆) δ:
  1.16(s, 6H), 1.36(s, 6H), 1.82(s, 4H), 6.31(s, 2H), 7.22–7.28(m, 1H), 7.34–7.39(m, 1H), 7.68(d, J=8.8 Hz, 1H), 7.85(d, J=8.2 Hz, 2H), 8.03(d, J=8.2 Hz, 2H), 8.15(s, 1H), 8.27(d, J=8.8 Hz, 1H), 8.36–8.44(m, 2H).

Referential Example 1

Preparation of 5,6,7,8-tetrahydro-2,3-diisopropyl-8-quinoxalinone

Step 1

Preparation of 5,6,7,8-tetrahydro-2 3-diisopropylquinoxaline

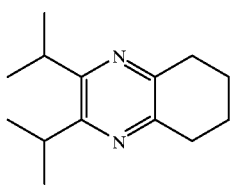

8.7 g of 2,5-dimethyl-3,4-hexanedione and 11.2 ml of 1,2-cyclohexanediamine were dissolved in 20 ml of acetic acid. The obtained solution was heated under reflux for 30 hours, cooled by allowing to stand, and poured into water, followed by the extraction with ethyl acetate. The organic phase was washed with a saturated aqueous solution of sodium hydrogencarbonate and a saturated aqueous solution of common salt, dried over anhydrous magnesium sulfate, and concentrated in a vacuum. The obtained residue was purified by silica gel chromatography (developer: 5% ethyl acetate/hexane) to give 6.8 g of the title compound as a colorless oil.
¹H-NMR(400 MHz, CDCl₃) δ:
  1.25(d, J=6.8 Hz, 12H), 1.84–1.92(m, 4H), 2.83–2.90(m, 4H), 3.23–3.34(m, 2H).

Step 2

Preparation of 5 6,7,8-tetrahydro-2,3-diisopropyl-8-quinoxalinone

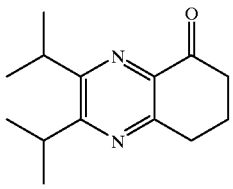

1.5 g of 5,6,7,8-tetrahydro-2,3-diisopropyl-quinoxaline was dissolved in 10 ml of acetic acid, followed by the dropwise addition of a solution of 1.0 g of chromic acid anhydride in acetic acid (6 ml) /water (1 ml). The obtained mixture was stirred at 80° C. for 2 hours, cooled by allowing to stand, and poured into water, followed by the extraction with ethyl acetate. The organic phase was washed with a saturated aqueous solution of sodium hydrogencarbonate and a saturated aqueous solution of common salt, dried over anhydrous magnesium sulfate, and concentrated in a vacuum. The obtained residue was purified by silica gel chromatography (developer: 10% ethyl acetate/hexane) to give 0.6 g of the title compound as a brown solid.
M.p.: 92 to 94° C.
$^1$H-NMR(400 MHz, CDCl$_3$) δ:
1.28(d, J=6.8 Hz, 6H), 1.32(d, J=6.8 Hz, 6H), 2.16–2.22 (m, 4H), 2.75–2.78(m, 2H), 3.11–3.14(m, 2H), 3.33–3.43(m, 2H).

Referential Example 2

Preparation of 1,2,3,4,6,7,8,9-octahydro-6,6,9,9-tetramethylphenazin-1-one

Step 1

Preparation of 3,3,6,6-tetramethyl-1,2-cyclohexanedione

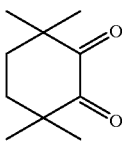

44.6 g of sodium (40% oily dispersion) was suspended in 1 l of xylene in a nitrogen atmosphere. The obtained suspension was heated to 100° C. A solution of 50 g of ethyl 2,2,5,5-tetramethylhexane-dicarboxylate in 100 ml of xylene was dropped into the suspension in 30 miniutes. The obtained mixture was stirred for 2 hours, and cooled to room temperature by allowing to stand and then using ice. 100 ml of a 50% aqueous solution of sulfuric acid was carefully dropped into the mixture, followed by the extraction with ethyl acetate. The organic phase was washed with water and a saturated aqueous solution of common salt, dried over magnesium sulfate, and concentrated in a vacuum. The obtained residue was purified by silica gel chromatography (developer: 5% ethyl acetate/hexane) to give 28 g of a pale-yellow oil.

This oil was dissolved in 70 ml of acetic acid, followed by the dropwise addition of a solution of 18 g of chromic acid anhydride in acetic acid (70 ml)/water (9 ml) at 10° C. The obtained mixture was brought to room temperature, stirred for 3 hours, and poured into 2 l of water to precipitate crystals. The crystals were recovered by filtration, washed with water and dried in a vacuum to give 19.5 g of the title compound as a yellow solid.
M.p.: 109 to 111° C.
$^1$H-NMR(400 MHz, CDCl$_3$) δ:
1.16(s, 12H), 1.87(s, 4H).

Step 2

Preparation of 1,2,3,4,6,7,8,9-octahydro-1,1,4,4-tetramethylphenazine

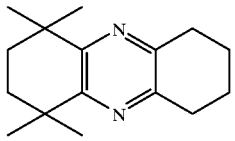

20.0 g of 3,3,6,6,-tetramethyl-1,2-cyclohexanedione and 20 ml of 1,2-cyclohexanediamine were dissolved in 20 ml of acetic acid. The obtained solution was heated under reflux for 6 hours, cooled by allowing to stand, and poured into water, followed by the extraction with ethyl acetate. The organic phase was washed with a saturated aqueous solution of sodium hydrogencarbonate and a saturated aqueous solution of common salt, dried over anhydrous magnesium sulfate, and concentrated in a vacuum. The obtained residue was purified by silica gel chromatography (developer: 5% ethyl acetate/hexane) to give 16.0 g of the title compound as a colorless oil.
$^1$H-NMR(400 MHz, CDCl$_3$) δ:
1.28(s, 12H), 1.75(s, 4H), 1.86–1.90(m, 4H), 2.83–2.88 (m, 4H).

Step 3

Preparation of 1,2,3,4,6,7,8,9-octahydro-6,6,9,9-tetramethylphenazin-1-one

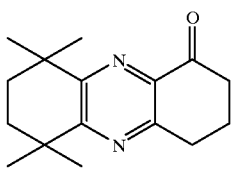

8.0 g of 1,2,3,4,6,7,8,9-octahydro-1,1,4,4-tetramethylphenazine was dissolved in 30 ml of acetic acid, followed by the dropwise addition of a solution of 4.9 g of chromic acid anhydride in acetic acid (30 ml)/water (4 ml). The obtained mixture was stirred at 80° C. for 30 minutes, cooled by allowing to stand, and poured into water, followed by the extraction with ethyl acetate. The organic phase was washed with a saturated aqueous solution of sodium hydrogencarbonate and a saturated aqueous solution of common salt, dried over anhydrous magnesium sulfate and concentrated in a vacuum. The obtained residue was purified by silica gel chromatography (developer: 20% ethyl acetate/hexane) to give 1.6 g of the title compound as a brown oil.
$^1$H-NMR(400 MHz, CDCl$_3$) δ:
1.33(s, 6H), 1.35(s, 6H), 1.81(s, 4H), 2.15–2.23(m, 2H), 2.77(dd, J=5.9, 6.9 Hz, 2H), 3.12(dd, J=5.9, 5.9 Hz, 2H).

Referential Example 3

Preparation of 6,7,8,9-tetrahydro-6,6,9,9-tetramethylthianaphtho[2,3-b]-cyclohexan-1-one

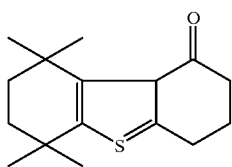

Step 1

Preparation of 2,5-dimethyl-5-(2-thienyl)-2-hexanol

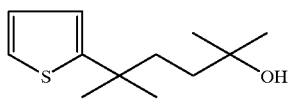

70 ml of a 3 mol/l solution of methylmagnesium bromide in diethyl ether was dropped into 200 ml of a solution of 20.4 g of ethyl 4-methyl-4-(2-thienyl)valerate in anhydrous diethyl ether under cooling with ice, followed by the stirring for 10 minutes. The obtained mixture was further stirred at room temperature for 2.5 hours. The resulting mixture was cooled with ice, and a saturated aqueous solution of ammonium chloride was carefully added to the mixture to decompose excess reagent. The organic phase was washed with a saturated aqueous solution of sodium chloride, dried over anhydrous magnesium sulfate and distilled in a vacuum to remove the solvent, thus giving 19.8 g of the title alcohol as a colorless oil.

$^1$H-NMR(400 MHz, CDCl$_3$) δ(ppm):

1.16(s, 6H), 1.30–1.38(m, 2H), 1.38(s, 6H), 1.65–1.72(m, 2H), 6.77–6.80(m, 1H), 6.88–6.92(m, 1H), 7.13(d, J=5.0 Hz, 1H)

Step 2

Preparation of 4,5,6,7-tetrahydro-4 4 7,7-tetramethylthianaphthene

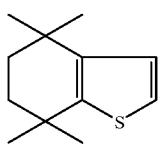

19.8 g of 2,5-dimethyl-5-(2-thienyl)-2-hexanol was added to 150 ml of a dichloromethane suspension of 16 g of aluminum chloride under cooling with ice. The obtained mixture was stirred for 30 minutes and poured onto ice-water, followed by the extraction with ethyl acetate. The organic phase was washed with water, a saturated aqueous solution of sodium hydrogencarbonate and a saturated aqueous solution of common salt successively, dried over anhydrous magnesium sulfate, and concentrated in a vacuum. The obtained residue was purified by silica gel chromatography (developer: n-hexane) to give 9.3 g of a colorless oil.

$^1$H-NMR(400 MHz, CDCl$_3$) δ(ppm):

1.23(s, 6H), 1.33(s, 6H), 1.65–1.75(m, 4H), 6.83(d, J=5.4 Hz, 1H), 7.15(d, J=5.4 Hz, 1H).

Step 3

Preparation of 6,7,8,9-tetrahydro-6,6,9,9-tetramethylthianaphtho[2,3-b]-cyclohexan-1-one

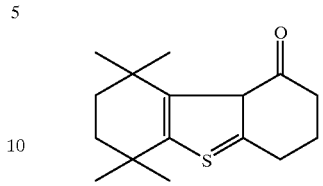

9.3 g of 4,5,6,7-tetrahydro-4,4,7,7-tetramethylthianaphthene and 9.4 g of chloride of monoethyl succinate were added to 100 ml of methylene chloride, followed by the dropwise addition of 6.7 ml of a 1M solution of stannic chloride in methylene chloride under cooling with ice. The obtained mixture was stirred at room temperature for 2.5 hours and poured onto ice-water, followed by the extraction with 200 ml of ethyl acetate. The organic phase was washed with water, a saturated aqueous solution of sodium hydrogencarbonate and a saturated aqueous solution of common salt successively, dried over anhydrous magnesium sulfate, and concentrated in a vacuum. The obtained residue was dissolved in 100 ml of ethanol, followed by the addition of 50 ml of a 5N aqueous solution of sodium hydroxide. The obtained mixture was stirred at room temperature for 2 hours and acidified with dilute hydrochloric acid, followed by the addition of ethyl acetate. The organic phase was washed with a saturated aqueous solution of common salt, dried over anhydrous magnesium sulfate, and distilled in a vacuum to remove the solvent. The obtained solid residue was washed with n-hexane to give 12.6 g of a white solid.

This solid was suspended in 150 ml of diethylene glycol, followed by the addition of 8.6 g of sodium hydroxide and 6.4 g of hydrazine monohydrate. The obtained mixture was vigorously stirred at 180° C. in a nitrogen stream for 4 hours, cooled by allowing to stand, and poured into cooled dilute hydrochloric acid, followed by the extraction with 200 ml of ethyl acetate. The organic phase was washed with a saturated aqueous solution of common salt, dried over anhydrous magnesium sulfate, and concentrated in a vacuum to give 10.4 g of a yellow oil.

100 g of polyphosphoric acid was added to this oil. The obtained mixture was stirred at 170° C. in a nitrogen stream for 2 hours, cooled by allowing to stand, and poured onto ice-water, followed by the extraction with 200 ml of ethyl acetate. The organic phase was washed with water, a saturated aqueous solution of sodium hydrogencarbonate and a saturated aqueous solution of common salt successively, dried over anhydrous magnesium sulfate, and concentrated in a vacuum. The obtained residue was purified by silica gel chromatography (developer: 2% ethyl acetate/n-hexane) to give 7.0 g of the title compound as a yellow oil.

$^1$H-NMR(400 MHz, CDCl$_3$) δ(ppm):

1.28(s, 6H), 1.36(s, 6H), 1.66(s, 4H), 2.08–2.16(m, 2H), 2.53(t, J=6.8 Hz, 2H), 2.96(t, J=6.8 Hz, 2H).

What is claimed is:

1. A mono- or polyenic carboxylic acid derivative represented by the formula (1-I) or a physiologically acceptable salt thereof:

$$Z\text{-}(CR^3=CR^2)_n\text{—}COOR^1 \qquad (1\text{-}I)$$

wherein $R^1$ is hydrogen or a carboxyl-protecting group; $R^2$ and $R^3$ are each independently hydrogen, halogen, linear lower alkyl, branched lower alkyl, linear lower alkoxy, branched lower alkoxy or aryl; n is an integer of 1 to 3 and the number of $R^{2'}$s or $R^{3'}$s may be the same or different from each other; and Z represents a group of the formula:

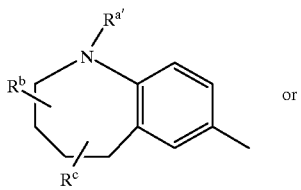

or

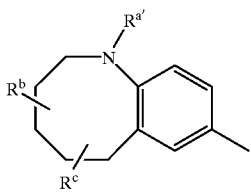

where $R^{a'}$ is hydrogen, linear or branched lower alkyl, linear or branched lower alkoxy, cycloalkyl, aryl, heteroaryl or fluoroalkyl, and $R^b$ and $R^c$ are each independently hydrogen, linear or branched lower alkyl, linear or branched lower alkoxy, cycloalkyl, aryl, heteroaryl, fluoroalkyl or halogen.

2. The mono- or polyenic carboxylic acid derivative or physiologically acceptable salts thereof according to claim 1 wherein n is 3.

3. The mono- or polyenic carboxylic acid derivative or physiologically cceptable salts thereof according to claim 1 having the formula:

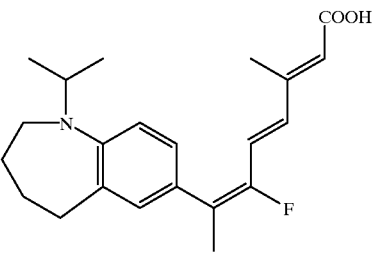

4. A pharmaceutical composition comprising a compound according to claim 1 together with a pharmaceutically acceptable diluent.

5. A method of treating autoimmune disease, malignant neoplasm or inducing immunosuppression in organ transplantation comprising administering to a patent requiring same an effective amount of a compound according to claim 1.

6. The method of claim 5 wherein the autoimmune disease is psoriasis, rheumatoid arthritis, multiple sclerosis, thrombocytopenia, insulin-dependent diabetes mellitus, atopic dermatitis or systematic lupus erythematosus.

7. The method of claim 5 wherein the malignant neoplasam is an acute promyelocytic leukemia or acute myelocytic leukima.

* * * * *